(12) United States Patent
Harrison et al.

(10) Patent No.: US 11,046,685 B2
(45) Date of Patent: Jun. 29, 2021

(54) INHIBITORS OF (α-V)(β-6) INTEGRIN

(71) Applicant: Morphic Therapeutic, Inc., Waltham, MA (US)

(72) Inventors: Bryce A. Harrison, Framingham, MA (US); Matthew G. Bursavich, Needham, MA (US); Aleksey I. Gerasyuto, Flemington, NJ (US); Kristopher N. Hahn, Medford, MA (US); Kyle D. Konze, Brooklyn, NY (US); Fu-Yang Lin, Sudbury, MA (US); Blaise S. Lippa, Newton, MA (US); Alexey A. Lugovskoy, Belmont, MA (US); Bruce N. Rogers, Belmont, MA (US); Mats A. Svensson, New York, NY (US); Dawn M. Troast, Bedford, MA (US)

(73) Assignee: Morphic Therapeutic, Inc., Waltham, MA (US)

( * ) Notice: Subject to any disclaimer, the term of this patent is extended or adjusted under 35 U.S.C. 154(b) by 0 days.

(21) Appl. No.: 16/489,646

(22) PCT Filed: Feb. 27, 2018

(86) PCT No.: PCT/US2018/019839
§ 371 (c)(1),
(2) Date: Aug. 28, 2019

(87) PCT Pub. No.: WO2018/160522
PCT Pub. Date: Sep. 7, 2018

(65) Prior Publication Data
US 2020/0002334 A1    Jan. 2, 2020

Related U.S. Application Data

(60) Provisional application No. 62/465,047, filed on Feb. 28, 2017.

(51) Int. Cl.
*C07D 471/04* (2006.01)
*A61K 31/4375* (2006.01)
*A61K 45/06* (2006.01)

(52) U.S. Cl.
CPC .......... *C07D 471/04* (2013.01); *A61K 45/06* (2013.01)

(58) Field of Classification Search
CPC .... C07D 471/04; A61K 31/4375; A61P 43/00
USPC .......................................... 546/122; 514/300
See application file for complete search history.

(56) References Cited

U.S. PATENT DOCUMENTS

| | | | |
|---|---|---|---|
| 5,952,341 A | 9/1999 | Duggan et al. | |
| 6,017,926 A | 1/2000 | Askew et al. | |
| 6,048,861 A | 4/2000 | Askew et al. | |
| 6,069,143 A | 5/2000 | Ali et al. | |
| 6,232,308 B1 | 5/2001 | Askew | |
| 6,358,970 B1 | 3/2002 | Duggan et al. | |
| 6,723,711 B2 | 4/2004 | Biediger et al. | |
| 8,716,226 B2 | 5/2014 | Ruminski et al. | |
| 9,572,801 B2 | 2/2017 | Askew et al. | |
| 10,604,520 B2 | 3/2020 | Jiang et al. | |
| 10,696,672 B2 | 6/2020 | Morgans, Jr. et al. | |
| 10,793,564 B2 | 10/2020 | Cha et al. | |
| 2001/0034445 A1 | 10/2001 | Ali et al. | |
| 2002/0010176 A1 | 1/2002 | Askew et al. | |
| 2002/0035127 A1 | 3/2002 | Head et al. | |
| 2004/0043988 A1 | 3/2004 | Khanna et al. | |
| 2008/0045521 A1 | 2/2008 | Arnould et al. | |
| 2009/0104116 A1 | 4/2009 | Zischinsky et al. | |
| 2012/0289481 A1 | 11/2012 | O'Neil et al. | |
| 2014/0038910 A1 | 2/2014 | Ruminski et al. | |
| 2014/0051715 A1 | 2/2014 | Ruminski et al. | |
| 2014/0349968 A1 | 11/2014 | O'Neil et al. | |
| 2016/0280705 A1 | 9/2016 | Anderson et al. | |
| 2017/0290817 A1 | 10/2017 | Anderson et al. | |
| 2017/0369490 A1 | 12/2017 | Askew et al. | |
| 2018/0008583 A1 | 1/2018 | Fukunaga et al. | |
| 2018/0093984 A1 | 4/2018 | Jiang et al. | |
| 2018/0244648 A1 | 8/2018 | Harrison et al. | |
| 2019/0248832 A1 | 8/2019 | Almeida et al. | |
| 2019/0276449 A1 | 9/2019 | Cha et al. | |
| 2020/0002334 A1 | 1/2020 | Harrison et al. | |
| 2020/0071322 A1 | 3/2020 | Harrison et al. | |
| 2020/0087299 A1 | 3/2020 | Brewer et al. | |
| 2020/0109141 A1 | 4/2020 | Cha et al. | |
| 2020/0157075 A1 | 5/2020 | Harrison et al. | |
| 2020/0354359 A1 | 11/2020 | Harrison et al. | |
| 2020/0385384 A1 | 12/2020 | Harrison et al. | |

FOREIGN PATENT DOCUMENTS

| | | | |
|---|---|---|---|
| EP | 0537696 A1 | 4/1993 | |
| EP | 0623615 A1 | 11/1994 | |
| EP | 2221308 A1 | 8/2010 | |
| WO | WO-1993/10091 A2 | 5/1993 | |
| WO | WO-93/14077 A1 | 7/1993 | |

(Continued)

OTHER PUBLICATIONS

Anderson et al., "The discovery of an orally bioavailable pan-#v integrin inhibitor for idiopathic pulmonary fibrosis," J. Med. Chem., Just Accepted Manuscript, (2019).

Brashear et al., "Non-Peptide $\alpha_v\beta_3$ Antagonists. Part 5: Identification of Potent RGD Mimetics Incorporating 2-Aryl β-Amino Acids as Aspartic Acid Replacements," Bioorganic & Medicinal Chemistry Letters 12: 3483-3486 (2002).

(Continued)

*Primary Examiner* — Charanjit Aulakh

(74) *Attorney, Agent, or Firm* — Foley Hoag LLP; Dana M. Gordon; Lawrence P. Tardibono

(57) ABSTRACT

Disclosed are small molecule inhibitors of αvβ6 integrin, and methods of using them to treat a number of diseases and conditions.

42 Claims, 1 Drawing Sheet

(56) References Cited

FOREIGN PATENT DOCUMENTS

| | | |
|---|---|---|
| WO | WO-97/24122 A1 | 7/1997 |
| WO | WO-97/24124 A1 | 7/1997 |
| WO | WO-97/25323 A1 | 7/1997 |
| WO | WO-97/36871 A1 | 10/1997 |
| WO | WO-98/08840 A1 | 3/1998 |
| WO | WO-98/46220 A1 | 10/1998 |
| WO | WO-1998/044797 A1 | 10/1998 |
| WO | WO-1999/026945 A1 | 6/1999 |
| WO | WO-1999/030713 A1 | 6/1999 |
| WO | WO-1999/031061 A1 | 6/1999 |
| WO | WO-1999/031099 A1 | 6/1999 |
| WO | WO-2000/006169 A1 | 2/2000 |
| WO | WO-2000/031067 A1 | 6/2000 |
| WO | WO-2000/037487 A1 | 6/2000 |
| WO | WO-2000/072801 A2 | 12/2000 |
| WO | WO-2000/073260 A1 | 12/2000 |
| WO | WO-2000/78317 A1 | 12/2000 |
| WO | WO-2001/005810 A2 | 1/2001 |
| WO | WO-2001/023357 A2 | 4/2001 |
| WO | WO-2001/044194 A2 | 6/2001 |
| WO | WO-2001/053262 A1 | 7/2001 |
| WO | WO-2001/053297 A1 | 7/2001 |
| WO | WO-2001/096334 A2 | 12/2001 |
| WO | WO-2002/16328 A1 | 2/2002 |
| WO | WO-2002/022124 A1 | 3/2002 |
| WO | WO-2002/022615 A1 | 3/2002 |
| WO | WO-2002/022616 A2 | 3/2002 |
| WO | WO-02/060438 A1 | 8/2002 |
| WO | WO-2002/074730 A1 | 9/2002 |
| WO | WO-2002/090325 A2 | 11/2002 |
| WO | WO-2003/066594 A2 | 8/2003 |
| WO | WO-2004/020435 A1 | 3/2004 |
| WO | WO-2006/024699 A1 | 3/2006 |
| WO | WO-2008/157162 A1 | 12/2008 |
| WO | WO-2014/015054 A1 | 1/2014 |
| WO | WO-2014/154725 A1 | 10/2014 |
| WO | WO-2014/154809 A1 | 10/2014 |
| WO | WO-2015/103643 A2 | 7/2015 |
| WO | WO-2015/150557 A1 | 10/2015 |
| WO | WO-2015/179823 A2 | 11/2015 |
| WO | WO-2016/022851 A1 | 2/2016 |
| WO | WO-2016/046225 A1 | 3/2016 |
| WO | WO-2016/046226 A1 | 3/2016 |
| WO | WO-2016/046230 A1 | 3/2016 |
| WO | WO-2016/046241 A1 | 3/2016 |
| WO | WO-2016/176532 A1 | 11/2016 |
| WO | WO-2017/117538 A1 | 7/2017 |
| WO | WO-2017/158072 A1 | 9/2017 |
| WO | WO-2017/162570 A1 | 9/2017 |
| WO | WO-2017/162572 A1 | 9/2017 |
| WO | WO-2018/009501 A1 | 1/2018 |
| WO | WO-2018/049068 A1 | 3/2018 |
| WO | WO-2018/085552 A1 | 5/2018 |
| WO | WO-2018/085578 A1 | 5/2018 |
| WO | WO-2018/089353 A1 | 5/2018 |
| WO | WO-2018/089355 A1 | 5/2018 |
| WO | WO-2018/089357 A1 | 5/2018 |
| WO | WO-2018/089358 A1 | 5/2018 |
| WO | WO-2018/089360 A1 | 5/2018 |
| WO | WO-2018/119087 A1 | 6/2018 |
| WO | WO-2018/132268 A1 | 7/2018 |
| WO | WO-2018/160521 A2 | 9/2018 |
| WO | WO-2018/160522 A1 | 9/2018 |
| WO | WO-2019/173653 A1 | 9/2019 |
| WO | WO-2020/006315 A1 | 1/2020 |
| WO | WO-2020/009889 A1 | 1/2020 |
| WO | WO-2020/047207 A1 | 3/2020 |
| WO | WO-2020/047208 A1 | 3/2020 |
| WO | WO-2020/047239 A1 | 3/2020 |
| WO | WO-2020/076862 A1 | 4/2020 |
| WO | WO-2020/081154 A1 | 4/2020 |
| WO | WO-2020/210404 A1 | 10/2020 |
| WO | WO-2020/047207 A8 | 12/2020 |

OTHER PUBLICATIONS

Breslin et al., "Nonpeptide $\alpha_v\beta_3$ antagonists. Part 10: In vitro and in vivo evaluation of a potent 7-methyl substituted tetrahydro-[1,8]naphthyridine derivative," Bioorganic & Medicinal Chemistry Letters, 14: 4515-4518 (2004).

Coleman et al., "Nonpeptide $\alpha_v\beta_3$ Antagonists. Part 11: Discovery and Preclinical Evaluation of Potent $\alpha_v\beta_3$ Antagonists for the Prevention and Treatment of Osteoporosis," J. Med. Chem. 47: 4829-4837 (2004).

Cui et al., "In Vitro and In Vivo Metabolism of a Potent and Selective Integrin $\alpha_v\beta_3$ Antagonist in Rats, Dogs, and Monkeys," Drug Metabolism and Disposition, 32(8): 848-861 (2004).

Duggan et al., "Nonpeptide $\alpha_v\beta_3$ Antagonists. 1. Transformation of a Potent, Integrin-Selective $\alpha_{IIb}\beta_3$ Antagonist into a Potent $\alpha_v\beta_3$ Antagonist," J. Med. Chem. 43: 3736-3745 (2000).

Goodman et al., "Nanomolar Small Molecule Inhibitors for $\alpha_v\beta_6$, $\alpha_v\beta_5$, and $\alpha_v\beta_3$ Integrins," J. Med. Chem. 45: 1045-1051 (2002).

Hall et al., "Characterisation of a novel, high affinity and selective $\alpha_v\beta_6$ integrin RGD-mimetic radioligand," Biochemical Pharmacology, 117(1): 88-96 (2016).

Hatley et al., "An αv-RGD integrin inhibitor toolbox: drug discovery insight, challenges and opportunities," Angew. Chem., 57(13): 3298-3321 (2017).

Hutchinson et al., "Nonpeptide $\alpha_v\beta_3$ Antagonists. 8. In Vitro and in Vivo Evaluation of a Potent $\alpha_v\beta_3$ Antagonist for the Prevention and Treatment of Osteoporosis," J. Med. Chem. 46: 4790-4798 (2003).

International Preliminary Report on Patentability for International Application No. PCT/EP00/06188 dated May 31, 2001.

International Preliminary Report on Patentability for International Application No. PCT/EP02/01836 dated Oct. 14, 2002.

International Preliminary Report on Patentability for International Application No. PCT/EP2003/000327 dated Dec. 3, 2003.

International Preliminary Report on Patentability for International Application No. PCT/EP2014/056167 dated Sep. 29, 2015.

International Preliminary Report on Patentability for International Application No. PCT/EP99/09842 dated Jan. 12, 2001.

International Preliminary Report on Patentability for International Application No. PCT/FI2005/050305 dated Feb. 28, 2007.

International Preliminary Report on Patentability for International Application No. PCT/GB00/02020 dated Sep. 19, 2001.

International Preliminary Report on Patentability for International Application No. PCT/GB00/04831 dated Oct. 1, 2002.

International Preliminary Report on Patentability for International Application No. PCT/US00/14901 dated Mar. 28, 2001.

International Preliminary Report on Patentability for International Application No. PCT/US00/16849 dated Jun. 29, 2001.

International Preliminary Report on Patentability for International Application No. PCT/US00/26537 dated Jan. 1, 2002.

International Preliminary Report on Patentability for International Application No. PCT/US01/01298 dated Oct. 8, 2001.

International Preliminary Report on Patentability for International Application No. PCT/US01/01953 dated Sep. 8, 2001.

International Preliminary Report on Patentability for International Application No. PCT/US01/28238 dated Jul. 31, 2002.

International Preliminary Report on Patentability for International Application No. PCT/US01/28404 dated Apr. 25, 2002.

International Preliminary Report on Patentability for International Application No. PCT/US01/42146 dated Sep. 5, 2002.

International Preliminary Report on Patentability for International Application No. PCT/US02/13457 dated Jul. 22, 2003.

Kinney el al., "Suzuki-Miyaura Approach to JNJ-26076713, an Orally Active Tetrahydroquinoline-Containing $\alpha_v\beta_3/\alpha_v\beta_5$ Integrin Antagonist. Enantioselective Synthesis and Stereochemical Studies," J. Org. Chem., 73: 2302-2310 (2008).

Macdonald et al., "Passing on the medicinal chemistry baton: training undergraduates to be industry-ready through research projects between the University of Nottingham and GlaxoSmithKline," Drug Discovery Today, 21(6): 880-887 (2016).

Peng et al., "Integrin $\alpha_v\beta_6$ Critically Regulates Hepatic Progenitor Cell Function and Promotes Ductular Reaction, Fibrosis, and Tumorigenesis," Hepatology 63(1): 217-232 (2016).

Perkins et al., "Non-peptide $\alpha_v\beta_3$ Antagonists: Identification of Potent, Chain-Shortened RGD Mimetics that Incorporate a Central

(56) References Cited

OTHER PUBLICATIONS

Pyrrolidinone Constraint," Bioorganic & Medicinal Chemistry Letters 13: 4285-4288 (2003).
Procopiou et al., "Discovery of (S)-3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic Acid, a Nonpeptidic $\alpha_v\beta_6$ Integrin Inhibitor for the Inhaled Treatment of Idiopathic Pulmonary Fibrosis," Journal of Medicinal Chemistry, 61(18): 8417-8443 (2018).
Rosenthal et al., "Evaluation of the safety, pharmacokinetics and treatment effects of an $\alpha_v\beta_3$ integrin inhibitor on bone turnover and disease activity in men with hormone-refractory prostate cancer and bone metastases," Journal of Clinical Oncology 6: 42-48 (2010).
Rubtsov et al., "RGD-based Therapy: Principles of Selectivity," Current Pharmaceutical Design, 22: 925-932 (2016).
Santulli et al., "Studies with an Orally Bioavailable $\alpha_v$ Integrin Antagonist in Animal Models of Ocular Vasculopathy: Retinal Neovascularization in Mice and Retinal Vascular Permeability in Diabetic Rats," Journal of Pharmacology and Experimental Therapeutics, 324(3): 894-901 (2008).
Tipping et al., Relative Binding Affinities of Integrin Antagonists by Equilibrium Dialysis and Liquid Chromatography-Mass Spectrometry, Medicinal Chemistry Letters, 6(2): 221-224 (2015).
Wang et al., "Non-peptide $\alpha_v\beta_3$ antagonists. Part 7: 3-Substituted tetrahydro-[1,8]naphthyridine derivatives," Bioorganic & Medicinal Chemistry Letters, 14: 1049-1052 (2004).
Whilding et al., "The integrin $\alpha_v\beta_6$: a novel target for CAR T-cell immunotherapy?," Biochem. Soc. Trans., 44: 349-355 (2016).
Whitman et al., "Nonpeptide $\alpha_v\beta_3$ antagonists. Part 9: Improved pharmacokinetic profile through the use of an aliphatic, des-amide backbone," Bioorganic & Medicinal Chemistry Letters, 14: 4411-4415 (2004).
Zhou et al., "An integrin antagonist (MK-0429) decreases proteinuria and renal fibrosis in the ZSF1 rat diabetic nephropathy model," Pharmacology Research & Perspectives, 5(5): 1-14 (2017).
Database Accession No. 1380858-49-0., Database Registry [Online] Chemical Abstracts Service: XP002799454 (2012).
Database Accession No. 1380909-02-3., Database Registry [Online] Chemical Abstracts Service: XP002799455 (2012).
Database Accession No. 1380948-25-3., Database Registry [Online] Chemical Abstracts Service: XP002799456 (2012).
Database Accession No. 1380999-27-8., Database Registry [Online] Chemical Abstracts Service: XP002799457 (2012).
Database Accession No. 1571616-43-7., Database Registry [Online] Chemical Abstracts Service: XP002799458 (2014).
Database Accession No. 1623225-85-3., Database Registry [Online] Chemical Abstracts Service: XP002799459 (2014).
Database Accession No. 1837357-51-3., Database Registry [Online] Chemical Abstracts Service: XP002799460 (2015).
Database Accession No. 1838839-35-2., Database Registry [Online] Chemical Abstracts Service: XP002799461 (2015).
Database Accession No. 1940788-29-3., Database Registry [Online] Chemical Abstracts Service: XP002799462 (2016).
Database Accession No. 2038980-05-9., Database Registry [Online] Chemical Abstracts Service: XP002799463 (2016).
Extended European Search Report for EP Application No. 18761396.3 dated Jul. 2, 2020.
Extended European Search Report for EP Application No. 20190341.6 dated Sep. 28, 2020.
Extended European Search Report for EP Application No. EP 18760393.1 dated Jul. 14, 2020.
Meissner et al., "Nonpeptide $\alpha_v\beta_3$ antagonists. Part 2: constrained glycyl amides derived from the RGD tripeptide," Bioorganic & Medicinal Chemistry Letters, 12(1): 25-29 (2002).
Bennet et al., "Cecil Textbook of Medicine," 20th Edition, 1:1004-1010 (1996).
Dermeret et al., "Another Anniversary for the War on Cancer" Bio/Technology, 12:320 (1994).
Freshney et al., "Culture of Animal Cells, A Manual of Basic Technique," 4, (1983).
International Search Report and Written Opinion for International Application No. PCT/US/18/19838 dated Aug. 8, 2018.
International Search Report and Written Opinion for International Application No. PCT/US18/19839 dated Aug. 9, 2018.
Prueksaritanont et al., "Disposition of a novel and potent $\alpha v\beta 3$ antagonist in animals, and extrapolation to man," Xenobiotica 34(1):103-115 (2004).
Prueksaritanont et al., "Renal elimination of a novel and potent $\alpha v\beta 3$ integrin antagonist in animals," Xenobiotica 34(11/12):1059-1074 (2004).
Raab-Westphal et al., "Integrins as Therapeutic Targets: Successes and Cancers, " Cancers, 9(110):1-28 (2017).
Rosenthal et al., "Evaluation of the safety, pharmacokinetics and treatment effects of an $\alpha v\beta 3$ integrin inhibitor on bone turnover and disease activity in men with hormone-refractory prostate cancer and bone metastases," Asia-Pac J Clin Oncol 6:42-48 (2010).
International Search Report for International Application No. PCT/US2019/055252 dated Jan. 23, 2020.
Written Opinion for International Application No. PCT/US2017/067622 dated Mar. 8, 2018.
Written Opinion for International Application No. PCT/US2019/021243 dated Jul. 5, 2019.
Written Opinion for International Application No. PCT/US2019/039624 dated Sep. 13, 2019.
Written Opinion for International Application No. PCT/US2019/055252 dated Jan. 23, 2020.
Extended European Search Report for EP Application No. EP 19194490 dated Dec. 10, 2019.
International Search Report and Written Opinion for International Application No. PCT/US2019/048734 dated Mar. 20, 2020.
International Search Report and Written Opinion for International Application No. PCT/US2019/048737 dated Dec. 27, 2019.
International Search Report and Written Opinion for International Application No. PCT/US2019/048738 dated Jan. 7, 2020.
International Search Report and Written Opinion for International Application No. PCT/US2019/048782 dated Dec. 27, 2019.
Invitation to Pay Additional Fees for International Application No. PCT/US2019/048737 dated Oct. 11, 2019.
Invitation to Pay Additional Fees for International Application No. PCT/US2019/048738 dated Oct. 11, 2019.
Invitation to Pay Additional Fees for International Application No. PCT/US2019/048782 dated Oct. 11, 2019.
Database Registry, Chemical Abstracts Services, CAS Registry No. 1155165-04-0 (Entered STN: Oct. 6, 2009).
Pickarski et al., "Orally active $\alpha v\beta 3$ integrin inhibitor MK-0429 reduces melanoma metastasis," Oncology Reports, 33: 2737-2745 (2015).
Search Report and Written Opinion for Singaporean Application No. 11201907820S dated Nov. 3, 2020.

| Compound | αvβ6 IC$_{50}$ | Compound | αvβ6 IC$_{50}$ | Compound | αvβ6 IC$_{50}$ |
|---|---|---|---|---|---|
| 1 | B | 8-P2 | A | 29 | A |
| 2-P1 | B | 9 | A | 30 | C |
| 2-P2 | C | 11-P1 | C | 31 | C |
| 3 | C | 11-P2 | A | 32 | C |
| 4-P1 | C | 13 | B | 39 | B |
| 4-P2 | C | 18 | B | 40 | B |
| 5 | A | 19 | A | 41 | B |
| 6 | A | 26 | A | 42 | B |
| 7 | B | 27 | C | 43 | C |
| 8-P1 | B | 28 | B | 46 | C |

Key to αvβ6 IC$_{50}$ Values

A = 0.01 μM < IC$_{50}$ < 0.1 μM

B = 0.1 μM < IC$_{50}$ < 1 μM

C = 1 μM < IC$_{50}$ < 10 μM

INHIBITORS OF (α-V)(β-6) INTEGRIN

RELATED APPLICATIONS

This application is the 35 U.S.C. 371 national phase of International Patent Application No. PCT/US2018/19839, filed Feb. 27, 2018, which claims benefit of priority to U.S. Provisional Patent Application No. 62/465,047, filed Feb. 28, 2017.

BACKGROUND OF THE INVENTION

The heterodimeric integrin family of receptors modulate cellular shape and cell adhesion to the extracellular matrix in response to extrinsic and intrinsic cues.

Integrin signaling controls cell survival, cell cycle progression, cell differentiation, and cell migration.

The integrin receptor exclusively can signal a cell bi-directionally, both "inside-out" and "outside-in." Thus, they mediate cell migration by transmitting forces from the extracellular matrix to the cytoskeleton and regulate cytoskeletal organization to achieve shape changes needed during cell migration. RGD-binding integrins can bind to and activate TGF-β, and have recently been implicated in fibrotic disease and cancer.

Integrins are expressed on the surface of most of human cells. Their pathology contributes to a diverse set of human diseases, including platelet disorders, atherosclerosis, cancer, osteoporosis, fibrosis, diabetic neuropathy of the kidney, macular degeneration and various autoimmune and chronic inflammation diseases.

The role of integrins as drug targets has long been recognized, and a total of six injectable integrin inhibitors have been approved by the Food and Drug Administration for the treatment of various therapeutic indications: inflammatory bowel disease (Entyvio®, Tysabri®), multiple sclerosis (Tysabri®), psoriasis (Raptiva®), and acute coronary syndrome (Reopro®, Aggrastat®, Integrilin®). However, there has been a notable absence of therapeutic success with orally bioavailable integrin inhibitors.

Of the 24 known integrin heterodimers, as least half have relevance in inflammation, fibrosis, oncology and vascular disease. There exists a need for new classes of integrin inhibitors.

SUMMARY OF THE INVENTION

In certain embodiments, the invention relates to a compound of Formula I:

A-B-C     (I)

wherein:
A is

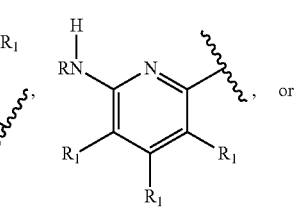

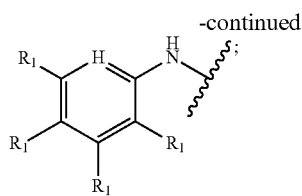

B is absent, alkylene, -alkylene-(O); -alkylene-N(R)C(O)—, -alkylene-(heterocyclyl)-C(O)—, -alkylene-C(O)N(R)—, -alkylene-C(O)—, -alkylene-N(R)—, -alkylene-N(R)C(O)N(R)—, -alkylene-N(R)SO$_2$—, -alkylene-(aryl)-, -alkylene-(heterocyclyl)-, alkylene-(heterocyclyl)-alkylene, -aryl-alkylene-N(R)C(O)—; -aryl-C(O)N(R)—, -aryl-N(R)C(O)—, -(heterocyclyl)-alkylene-, -heterocyclyl-alkylene-N(R)C(O)—; -heterocyclyl-C(O)N(R)—, —O-heterocyclyl-; -alkylene-O—; -heterocyclyl-C(O)—; cycloalkylene; or cycloalkylene-O—;
C is

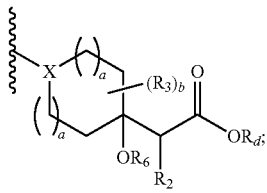

R is H, alkyl, or aryl;
R$_1$ is independently H, halide, alkoxy, CF$_3$, OH, NO$_2$, —N(H)R, or NH$_2$;
R$_2$ is H, alkyl, substituted or unsubstituted aryl, substituted or unsubstituted heteroaryl, cycloalkyl, -alkylene-alkoxy, alkoxy, —OH, -alkylene-aryl, heterocycloalkyl, —N(R)C(O)R$_4$, —N(R)SO$_2$R$_4$—, —N(R)-aryl, or —N(R)-heteroaryl;
R$_3$ is independently alkyl, halide, alkoxy, CF$_3$, OH, NO$_2$, or NH$_2$;
R$_4$ is alkyl, cycloalkyl, heterocycloalkyl, aryl, heteroaryl, -alkylene-heterocyclyl, -alkylene-N(R)C(O)R$_5$, or -alkylene-N(R)—SO$_2$Me;
R$_5$ is alkyl, or cycloalkyl;
R$_6$ is H, or alkyl;
X is C(R$_c$) or N;
R$_c$ is H, alkyl, aryl, OH, or halide;
R$_d$ is H, or (C$_1$-C$_6$)alkyl;
a is independently 0, or 1; and
b is 0, 1, 2, 3, or 4;
or a pharmaceutically acceptable salt thereof.

In certain embodiments, the invention relates to a compound selected from the group consisting of:

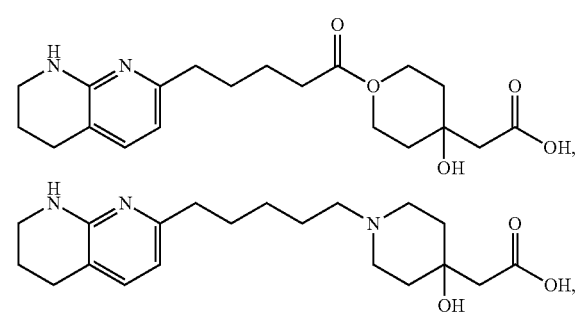

-continued
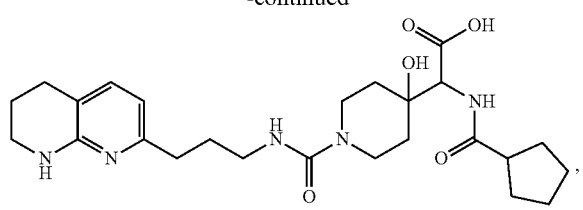
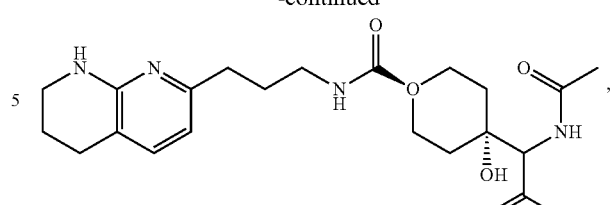
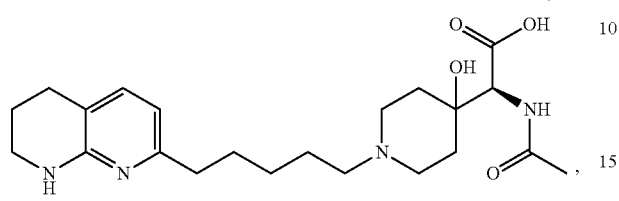
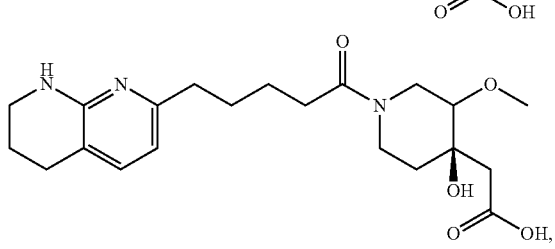
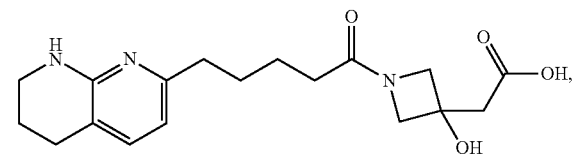
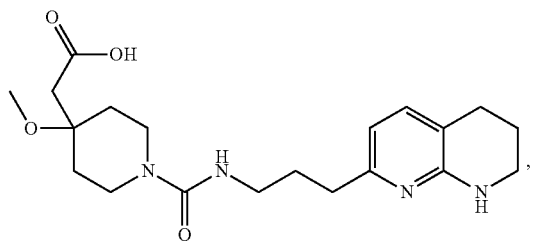
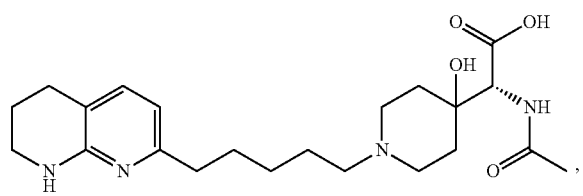
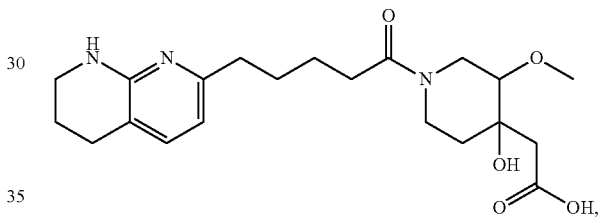
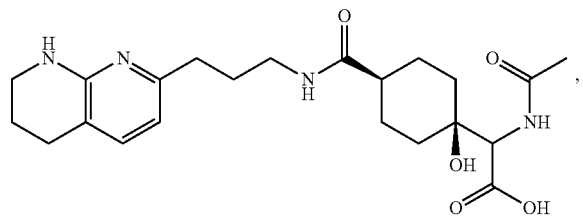
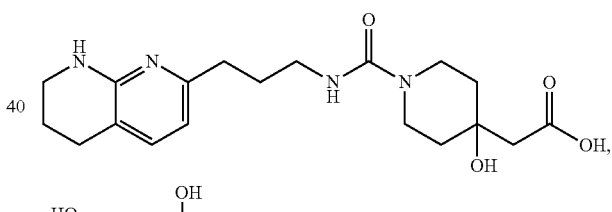
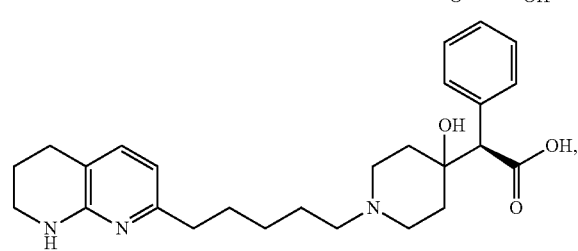
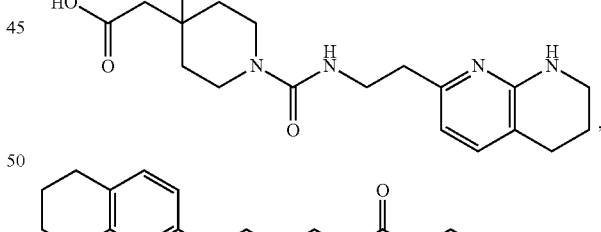
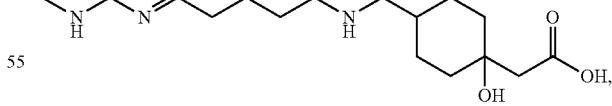
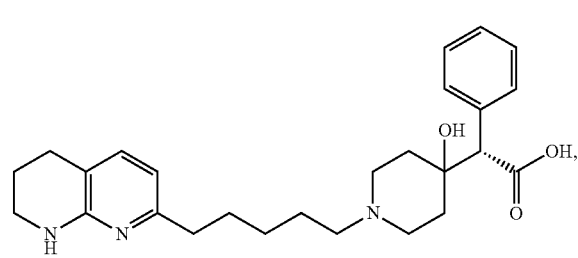
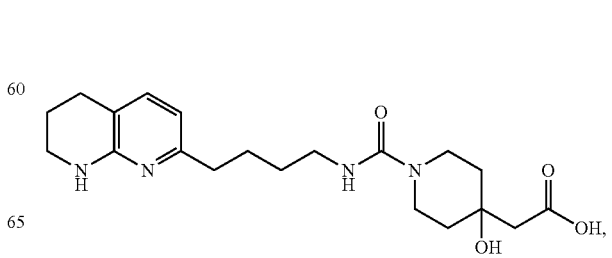

-continued
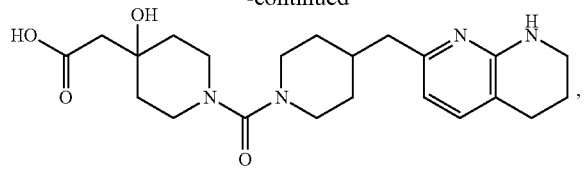
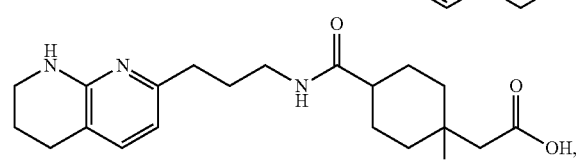
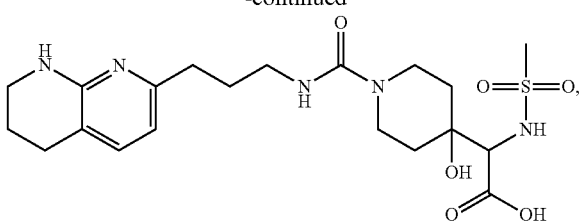
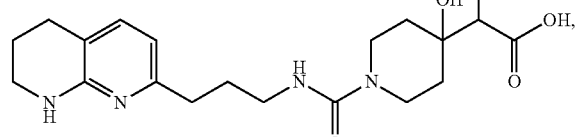
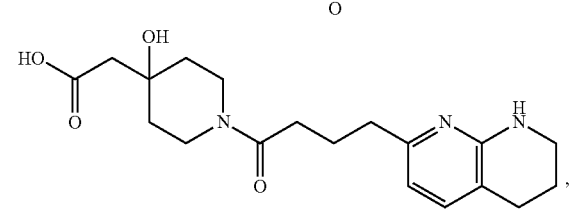
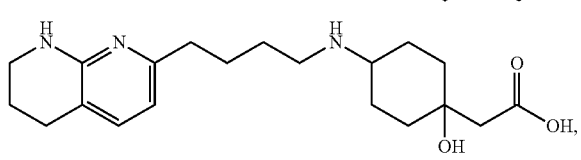
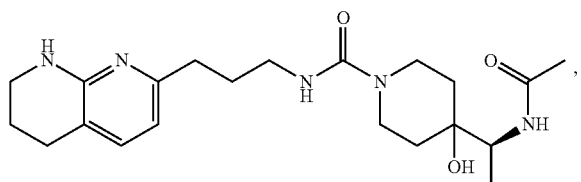
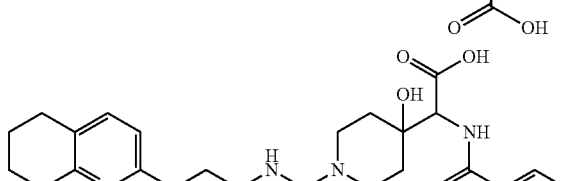
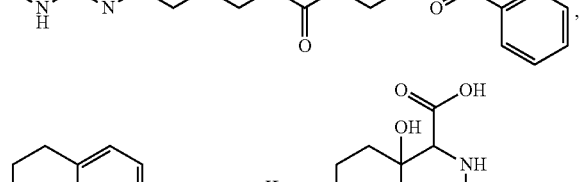
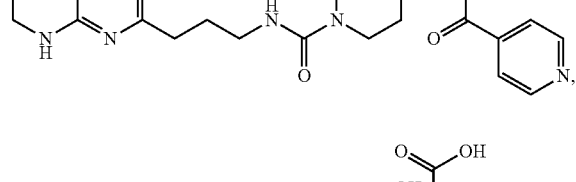
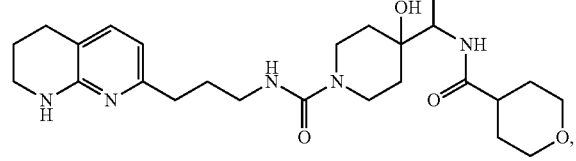

-continued
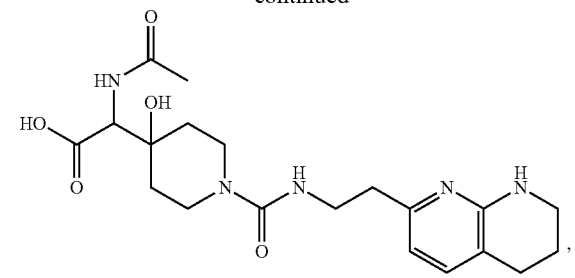
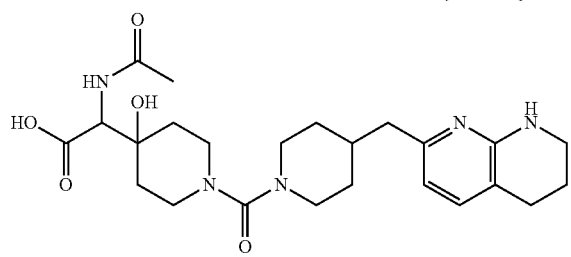
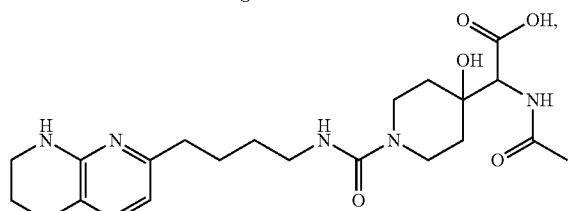
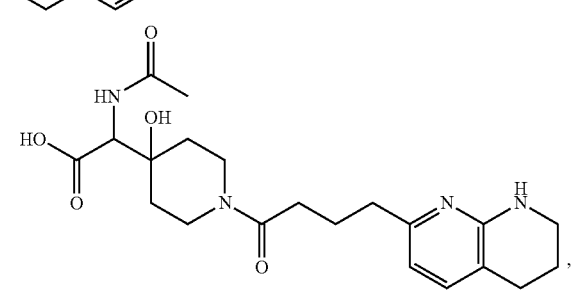
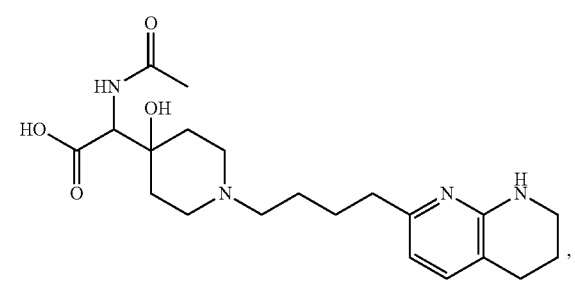
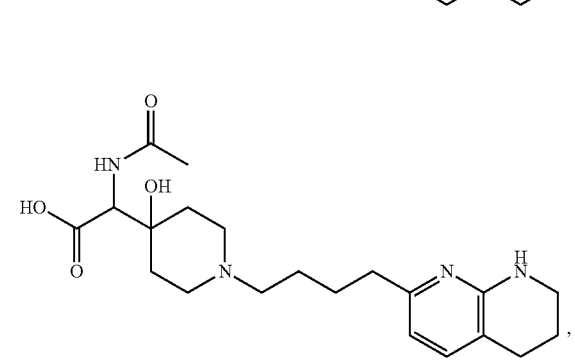
-continued
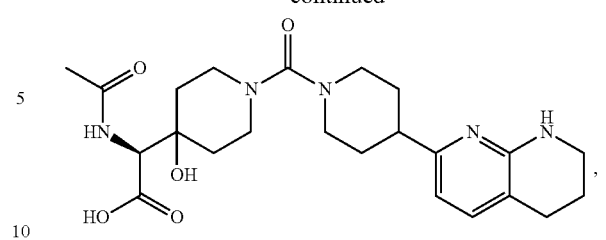
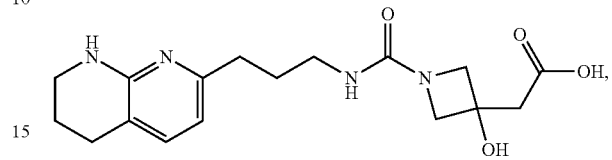
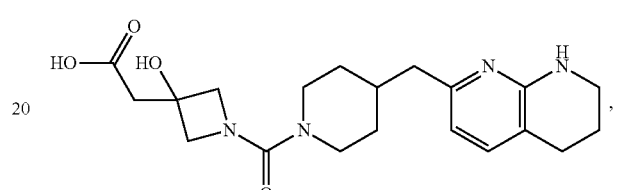
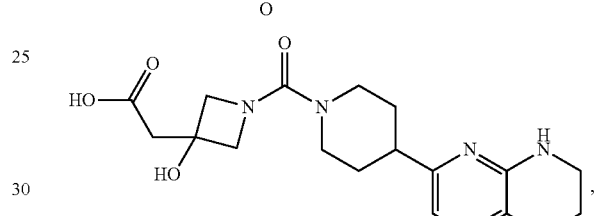
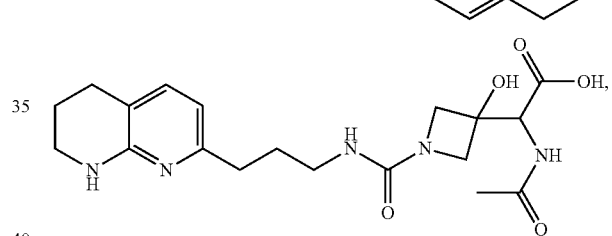
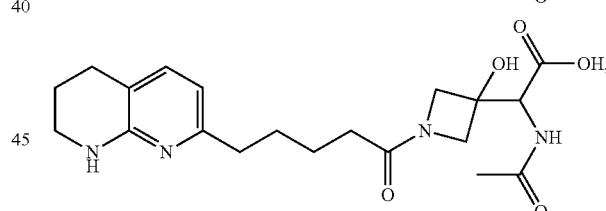
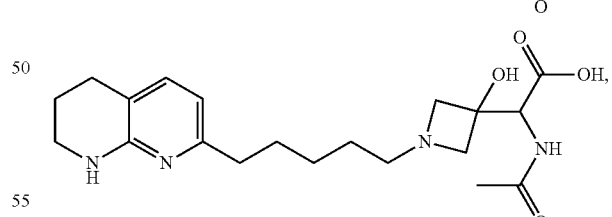
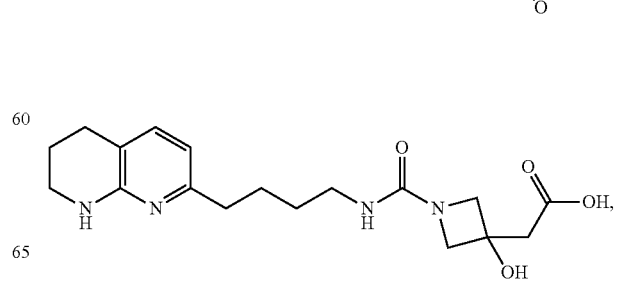

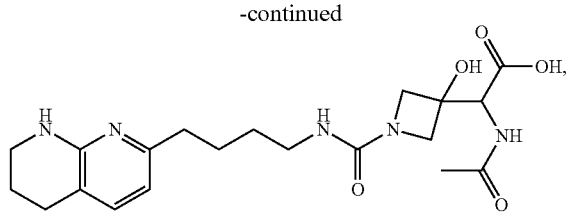
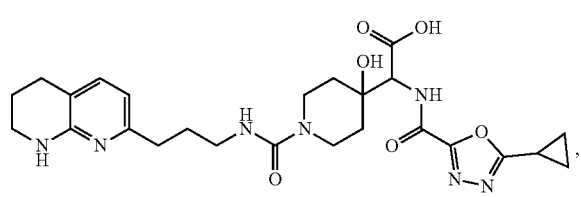
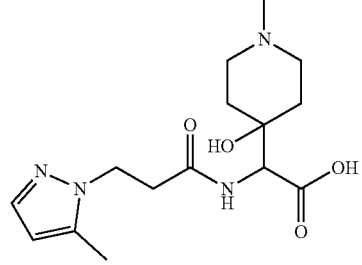
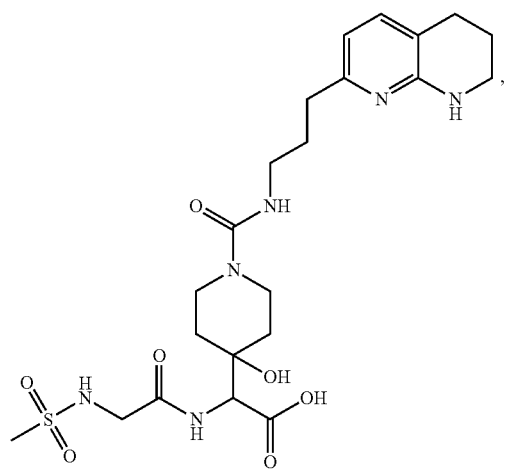
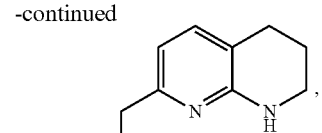
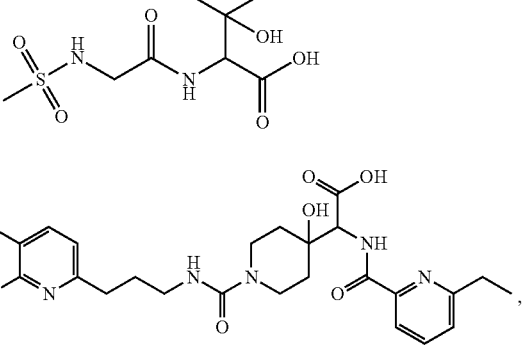
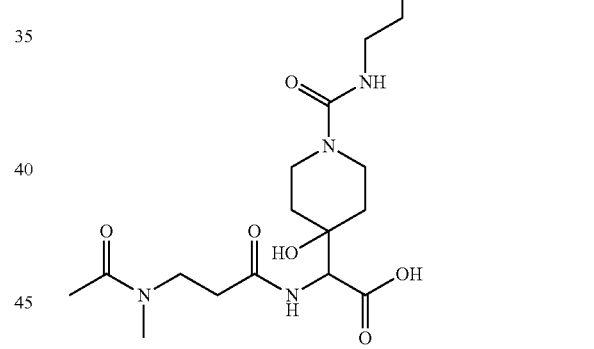
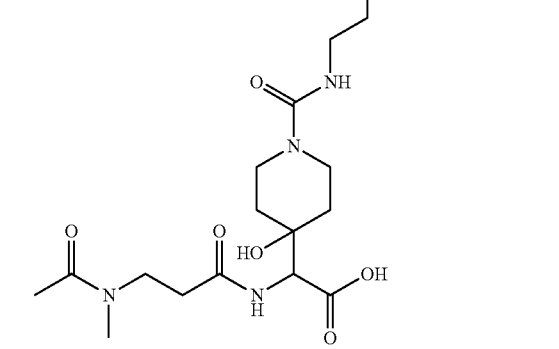
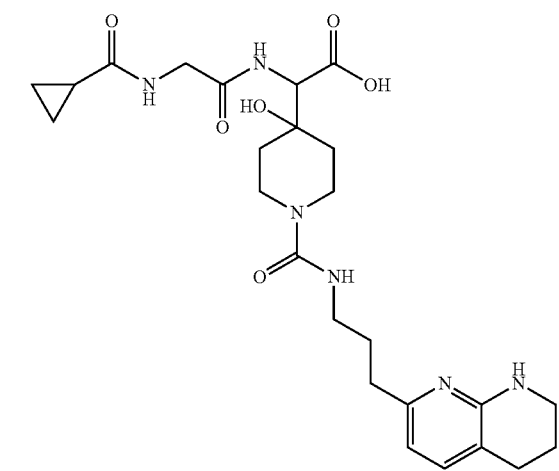

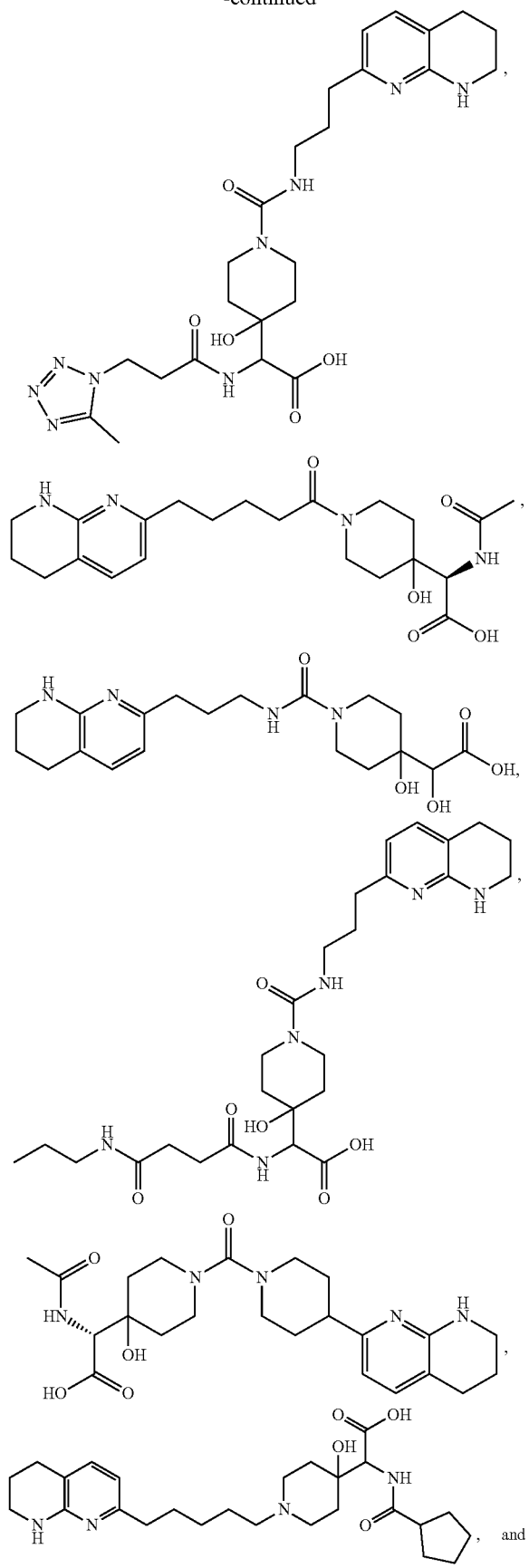

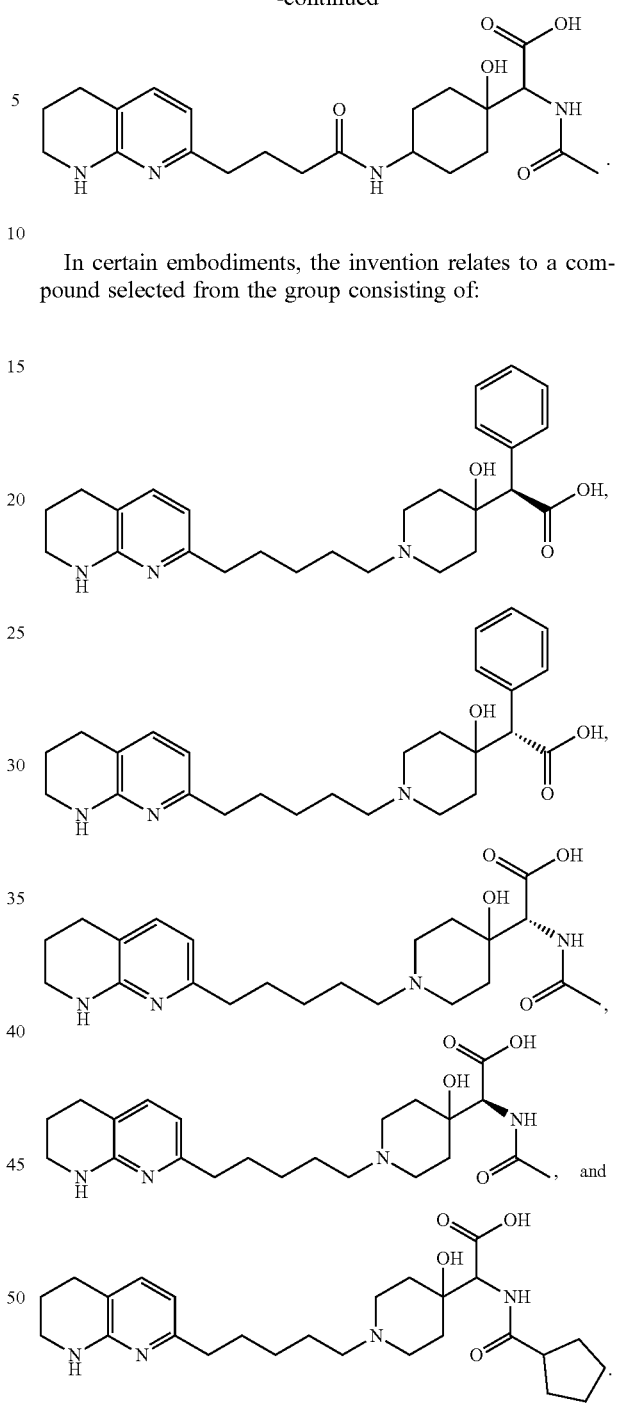

In certain embodiments, the invention relates to a compound selected from the group consisting of:

In certain embodiments, the invention relates to a method of treating a disease or a condition selected from the group consisting of idiopathic pulmonary fibrosis, diabetic nephropathy, focal segmental glomerulosclerosis, chronic kidney disease, nonalcoholic steatohepatitis, primary biliary cholangitis, primary sclerosing cholangitis, solid tumors, hematological tumors, organ transplant, Alport syndrome, interstitial lung disease, radiation-induced fibrosis, bleomycin-induced fibrosis, asbestos-induced fibrosis, flu-induced fibrosis, coagulation-induced fibrosis, vascular injury-induced fibrosis, aortic stenosis, and cardiac fibrosis, comprising the step of: administering to a subject in need thereof a therapeutically effective amount of any one of the compounds described herein.

BRIEF DESCRIPTION OF THE FIGURES

FIG. 1 depicts a table summarizing inhibition of αvβ6 integrin by example compounds in fluorescence polarization assay.

DETAILED DESCRIPTION OF THE INVENTION

In certain embodiments, the invention relates to compounds that inhibit αvβ6 integrin. In certain embodiments, the compounds are selective for αvβ6 integrin.

The compounds will be useful for the treatment of idiopathic pulmonary fibrosis, diabetic nephropathy, focal segmental glomerulosclerosis, chronic kidney disease, nonalcoholic steatohepatitis, primary biliary cholangitis, primary sclerosing cholangitis, solid tumors, hematological tumors, organ transplant, Alport syndrome, interstitial lung disease, radiation-induced fibrosis, bleomycin-induced fibrosis, asbestos-induced fibrosis, flu-induced fibrosis, coagulation-induced fibrosis, or vascular injury-induced fibrosis.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Structures depicted herein are also meant to include compounds that differ only in the presence of one or more isotopically enriched atoms. For example, compounds produced by the replacement of a hydrogen with deuterium or tritium, or of a carbon with a $^{13}$C- or $^{14}$C-enriched carbon are within the scope of this invention.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66:1-19.)

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" (or "effective amount") of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "patient" refers to a mammal in need of a particular treatment. In certain embodiments, a patient is a primate, canine, feline, or equine. In certain embodiments, a patient is a human.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Alkyl groups may be substituted or unsubstituted.

As used herein, the term "alkylene" refers to an alkyl group having the specified number of carbons, for example from 2 to 12 carbon atoms, that contains two points of attachment to the rest of the compound on its longest carbon chain. Non-limiting examples of alkylene groups include methylene —(CH$_2$)—, ethylene —(CH$_2$CH$_2$)—, n-propylene —(CH$_2$CH$_2$CH$_2$)—, isopropylene —(CH$_2$CH(CH$_3$))—, and the like. Alkylene groups can be cyclic or acyclic, branched or unbranched carbon chain moiety, and may be optionally substituted with one or more substituents.

"Cycloalkyl" means mono- or bicyclic or bridged or spirocyclic, or polycyclic saturated carbocyclic rings, each having from 3 to 12 carbon atoms. Likewise, preferred cycloalkyls have from 3-10 carbon atoms in their ring structure, and more preferably have 3-6 carbons in the ring structure. Cycloalkyl groups may be substituted or unsubstituted.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosenyl, docosenyl, tricosenyl, and tetracosenyl, in their various isomeric forms, where the unsaturated bond(s) can be located anywhere in the moiety and can have either the (Z) or the (E) configuration about the double bond(s).

"Alkynyl" refers to hydrocarbyl moieties of the scope of alkenyl, but having one or more triple bonds in the moiety.

The term "alkylthio" refers to an alkyl group, as defined above, having a sulfur moiety attached thereto. In certain embodiments, the "alkylthio" moiety is represented by one of —(S)-alkyl, —(S)-alkenyl, —(S)-alkynyl, and —(S)—(CH$_2$)$_m$—R$^1$, wherein m and R$^1$ are defined below. Representative alkylthio groups include methylthio, ethylthio, and the like.

The terms "alkoxyl" or "alkoxy" as used herein refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_{10}$, where m and R$_{10}$ are described below.

The terms "amine" and "amino" are art-recognized and refer to both unsubstituted and substituted amines, e.g., a moiety that can be represented by the formulae:

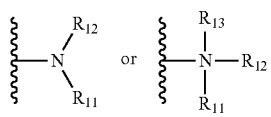

wherein R$_{11}$, R$_{12}$ and R$_{13}$ each independently represent a hydrogen, an alkyl, an alkenyl, —(CH$_2$)$_m$—R$_{10}$, or R$_{11}$ and R$_{12}$ taken together with the N atom to which they are attached complete a heterocycle having from 4 to 8 atoms in the ring structure; R$_{10}$ represents an alkenyl, aryl, cycloalkyl, a cycloalkenyl, a heterocyclyl, or a polycyclyl; and m is zero or an integer in the range of 1 to 8. In certain embodiments, only one of R$_{11}$ or R$_{12}$ can be a carbonyl, e.g., R$_{11}$, R$_{12}$, and the nitrogen together do not form an imide. In even more certain embodiments, R$_{11}$ and R$_{12}$ (and optionally R$_{13}$) each independently represent a hydrogen, an alkyl, an alkenyl, or —(CH$_2$)$_m$—R$_{10}$. Thus, the term "alkylamine" as used herein means an amine group, as defined above, having a substituted or unsubstituted alkyl attached thereto, i.e., at least one of R$_{11}$ and R$_{12}$ is an alkyl group. In certain embodiments, an amino group or an alkylamine is basic, meaning it has a conjugate acid with a pK$_a$>7.00, i.e., the protonated forms of these functional groups have pK$_a$s relative to water above about 7.00.

The term "amide", as used herein, refers to a group

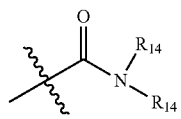

wherein each R$_{14}$ independently represent a hydrogen or hydrocarbyl group, or two R$_{14}$ are taken together with the N atom to which they are attached complete a heterocycle having from 4 to 8 atoms in the ring structure.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carbocyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 5- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic. The term "halo", "halide", or "halogen" as used herein means halogen and includes, for example, and without being limited thereto, fluoro, chloro, bromo, iodo and the like, in both radioactive and non-radioactive forms. In a preferred embodiment, halo is selected from the group consisting of fluoro, chloro and bromo.

The terms "heterocyclyl" or "heterocyclic group" refer to 3- to 12-membered ring structures, more preferably 5- to 12-membered rings, more preferably 5- to 10-membered rings, whose ring structures include one to four heteroatoms. Heterocycles can be monocyclic, bicyclic, spirocyclic, or polycyclic. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —CF$_3$, —CN, and the like.

The term "carbonyl" is art-recognized and includes such moieties as can be represented by the formula:

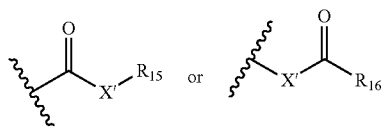

wherein X' is a bond or represents an oxygen or a sulfur, and R$_{15}$ represents a hydrogen, an alkyl, an alkenyl, —(CH$_2$)$_m$—R$_{10}$ or a pharmaceutically acceptable salt, R$_{16}$ represents a hydrogen, an alkyl, an alkenyl or —(CH$_2$)$_m$—R$_{10}$, where m and R$_{10}$ are as defined above. Where X' is an oxygen and R$_{15}$ or R$_{16}$ is not hydrogen, the formula represents an "ester." Where X' is an oxygen, and R$_{15}$ is as defined above, the moiety is referred to herein as a carboxyl group, and particularly when R$_{15}$ is a hydrogen, the formula represents a "carboxylic acid". Where X' is an oxygen, and R$_{16}$ is a hydrogen, the formula represents a "formate." In general, where the oxygen atom of the above formula is replaced by a sulfur, the formula represents a "thiocarbonyl" group. Where X' is a sulfur and R$_{15}$ or R$_{16}$ is not hydrogen, the formula represents a "thioester" group. Where X' is a sulfur and R$_{15}$ is a hydrogen, the formula represents a "thiocarboxylic acid" group. Where X' is a sulfur and R$_{16}$ is a hydrogen, the formula represents a "thioformate" group. On the other hand, where X' is a bond, and R$_{15}$ is not hydrogen, the above formula represents a "ketone" group. Where X' is a bond, and R$_{15}$ is a hydrogen, the above formula represents an "aldehyde" group.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "nitro" means —NO$_2$; the term "halogen" designates —F, —Cl, —Br, or —I; the term "sulfhydryl" means —SH; the term "hydroxyl" means —OH; the term "sulfonyl" means —SO$_2$—; the term "azido" means —N$_3$; the term "cyano" means —CN; the term "isocyanato" means —NCO; the term "thiocyanato" means —SCN; the term "isothiocyanato" means —NCS; and the term "cyanato" means —OCN.

The term "sulfamoyl" is art-recognized and includes a moiety that can be represented by the formula:

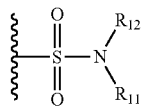

in which R$_{11}$ and R$_{12}$ are as defined above.

The term "sulfate" is art recognized and includes a moiety that can be represented by the formula:

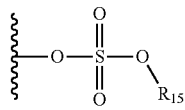

in which R$_{15}$ is as defined above.

The term "sulfonamide" is art recognized and includes a moiety that can be represented by the formula:

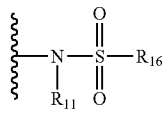

in which R$_{11}$ and R$_{16}$ are as defined above.

The term "sulfonate" is art-recognized and includes a moiety that can be represented by the formula:

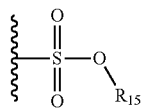

in which R$_{54}$ is an electron pair, hydrogen, alkyl, cycloalkyl, or aryl.

The terms "sulfoxido" or "sulfinyl", as used herein, refers to a moiety that can be represented by the formula:

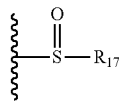

in which R$_{17}$ is selected from the group consisting of the group consisting of hydrogen, alkyl, alkenyl, alkynyl, cycloalkyl, heterocyclyl, aralkyl, or aryl.

The term "urea" is art-recognized and may be represented by the general formula

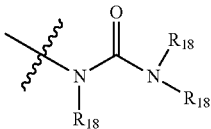

wherein each $R_{18}$ independently represents hydrogen or a hydrocarbyl, such as alkyl, or any occurrence of $R_{18}$ taken together with another and the intervening atom(s) complete a heterocycle having from 4 to 8 atoms in the ring structure.

As used herein, the definition of each expression, e.g., alkyl, m, n, etc., when it occurs more than once in any structure, is intended to be independent of its definition elsewhere in the same structure.

For purposes of this invention, the chemical elements are identified in accordance with the Periodic Table of the Elements, CAS version, Handbook of Chemistry and Physics, 67th Ed., 1986-87, inside cover.

Exemplary Compounds of the Invention

In certain embodiments, the invention relates to a compound of Formula I:

A-B-C  (I)

wherein:

A is

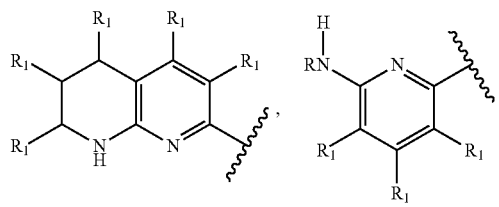

B is absent, alkylene, -alkylene-(O); -alkylene-N(R)C(O)—, -alkylene-(heterocyclyl)-C(O)—, -alkylene-C(O)N(R)—, -alkylene-C(O)—, -alkylene-N(R)—, -alkylene-N(R)C(O)N(R)—, -alkylene-N(R)SO₂—, -alkylene-(aryl)-, -alkylene-(heterocyclyl)-, alkylene-(heterocyclyl)-alkylene, -aryl-alkylene-N(R)C(O)—; -aryl-C(O)N(R)—, -aryl-N(R)C(O)—, -(heterocyclyl)-alkylene-, -heterocyclyl-alkylene-N(R)C(O)—; -heterocyclyl-C(O)N(R)—, —O-heterocyclyl-; -alkylene-O—; -heterocyclyl-C(O)—; cycloalkylene; or cycloalkylene-O—;

C is

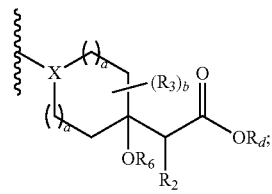

R is H, alkyl, or aryl;
$R_1$ is independently H, halide, alkoxy, $CF_3$, OH, $NO_2$, —N(H)R, or $NH_2$;
$R_2$ is H, alkyl, substituted or unsubstituted aryl, substituted or unsubstituted heteroaryl, cycloalkyl, -alkylene-alkoxy, alkoxy, —OH, -alkylene-aryl, heterocycloalkyl, —N(R)C(O)$R_4$, —N(R)SO₂$R_4$—, —N(R)-aryl, or —N(R)-heteroaryl;
$R_3$ is independently alkyl, halide, alkoxy, $CF_3$, OH, $NO_2$, or $NH_2$;
$R_4$ is alkyl, cycloalkyl, heterocycloalkyl, aryl, heteroaryl, -alkylene-heterocyclyl, -alkylene-N(R)C(O)$R_5$, or -alkylene-N(R)—SO₂Me;
$R_5$ is alkyl, or cycloalkyl;
$R_6$ is H, or alkyl;
X is C($R_c$) or N;
$R_c$ is H, alkyl, aryl, OH, or halide;
$R_d$ is H, or $(C_1-C_6)$alkyl;
a is independently 0, or 1; and
b is 0, 1, 2, 3, or 4;
or a pharmaceutically acceptable salt thereof.

In certain embodiments, the invention relates to any one of the aforementioned compounds, wherein A is

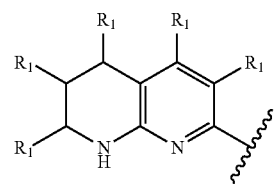

In certain embodiments, the invention relates to any one of the aforementioned compounds, wherein A is

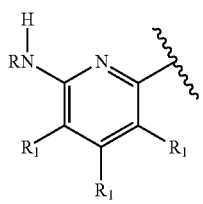

In certain embodiments, the invention relates to any one of the aforementioned compounds, wherein A is

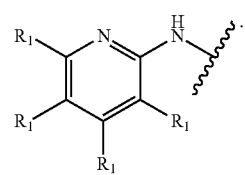

In certain embodiments, the invention relates to any one of the aforementioned compounds, wherein

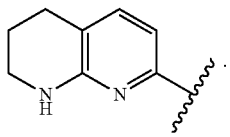 [SMILES: *c1ccc2c(n1)NCCC2]

In certain embodiments, the invention relates to any one of the aforementioned compounds, wherein $R_1$ is independently H, alkyl, halide, alkoxy, $CF_3$, OH, $NO_2$, —N(H)R, or $NH_2$. In certain embodiments, the invention relates to any one of the aforementioned compounds, wherein $R_1$ is independently halide, alkoxy, $CF_3$, OH, $NO_2$, or $NH_2$. In certain embodiments, the invention relates to any one of the aforementioned compounds, wherein $R_1$ is independently halide, OMe, OH, or $NH_2$. In certain embodiments, the invention relates to any one of the aforementioned compounds, wherein at least one instance of $R_1$ is alkyl. In certain embodiments, the invention relates to any one of the aforementioned compounds, wherein at least one instance of $R_1$ is methyl. In certain embodiments, the invention relates to any one of the aforementioned compounds, wherein at least one instance of $R_1$ is H. In certain embodiments, the invention relates to any one of the aforementioned compounds, wherein at least one instance of $R_1$ is halide. In certain embodiments, the invention relates to any one of the aforementioned compounds, wherein at least one instance $R_1$ is iodo, bromo, chloro, or fluoro. In certain embodiments, the invention relates to any one of the aforementioned compounds, wherein at least one instance of $R_1$ is iodo, bromo, chloro, or fluoro, and the other instances of $R_1$ are hydrogen. In certain embodiments, the invention relates to any one of the aforementioned compounds, wherein all instances of $R_1$ are H.

In certain embodiments, the invention relates to any one of the aforementioned compounds, wherein R is H, alkyl, or aryl. In certain embodiments, the invention relates to any one of the aforementioned compounds, wherein R is H. In certain embodiments, the invention relates to any one of the aforementioned compounds, wherein R is methyl. In certain embodiments, the invention relates to any one of the aforementioned compounds, wherein R is phenyl.

In certain embodiments, the invention relates to any one of the aforementioned compounds, wherein
B is absent, alkylene, -alkylene-(O); -alkylene-N(R)C(O)—, -alkylene-(heterocyclyl)-C(O)—, -alkylene-C(O)N(R)—, -alkylene-C(O)—, -alkylene-N(R)—, -alkylene-N(R)C(O)N(R)—, -alkylene-N(R)SO$_2$—, -alkylene-(aryl)-, -alkylene-(heterocyclyl)-, alkylene-(heterocyclyl)-alkylene, -aryl-alkylene-N(R)C(O)—; -aryl-C(O)N(R)—, -aryl-N(R)C(O)—, -(heterocyclyl)-alkylene-, -heterocyclyl-alkylene-N(R)C(O)—; -heterocyclyl-C(O)N(R)—, —O-heterocyclyl-; -alkylene-O—; -heterocyclyl-C(O)—; cycloalkylene; or cycloalkylene-O—.

In certain embodiments, the invention relates to any one of the aforementioned compounds, wherein B is absent, or represents alkylene, alkylene-N(R)—C(O)—, alkylene-N(R)—, or alkylene-C(O)—. In certain embodiments, the invention relates to any one of the aforementioned compounds, wherein B is absent, or represents $(C_1$-$C_6)$alkylene, —$(C_1$-$C_6)$alkylene-N(R)—C(O)—, —$(C_1$-$C_6)$alkylene-N(R)—, —$(C_1$-$C_6)$alkylene-O—, or —$(C_1$-$C_6)$alkylene-C(O)—.

In certain embodiments, the invention relates to any one of the aforementioned compounds, wherein B is selected from the group consisting of:

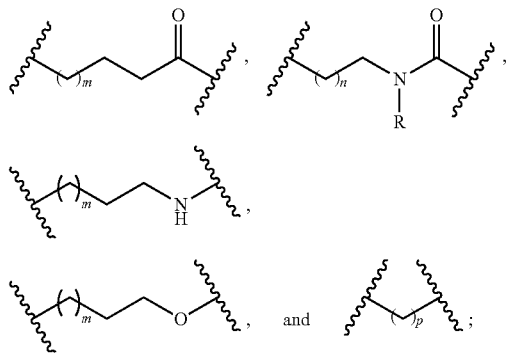

m is 0, 1, 2, or 3; n is 1, 2, or 3; and p is 1, 2, 3, 4, 5, or 6.

In certain embodiments, the invention relates to any one of the aforementioned compounds, wherein at least one instance of a is 0. In certain embodiments, the invention relates to any one of the aforementioned compounds, wherein both instances of a are 0. In certain embodiments, the invention relates to any one of the aforementioned compounds, wherein at least one instance of a is 1. In certain embodiments, the invention relates to any one of the aforementioned compounds, wherein both instances of a are 1.

In certain embodiments, the invention relates to any one of the aforementioned compounds, wherein b is 0. In certain embodiments, the invention relates to any one of the aforementioned compounds, wherein b is 1. In certain embodiments, the invention relates to any one of the aforementioned compounds, wherein b is 2. In certain embodiments, the invention relates to any one of the aforementioned compounds, wherein b is 1, or 2. In certain embodiments, the invention relates to any one of the aforementioned compounds, wherein b is at least 3.

In certain embodiments, the invention relates to any one of the aforementioned compounds, wherein both a are 0 and b is 0. In certain embodiments, the invention relates to any one of the aforementioned compounds, wherein both a are 1 and b is 0.

In certain embodiments, the invention relates to any one of the aforementioned compounds, wherein X is N.

In certain embodiments, the invention relates to any one of the aforementioned compounds, wherein C is selected from the group consisting of:

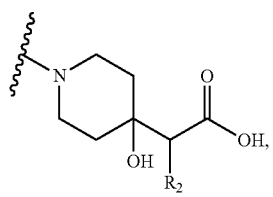

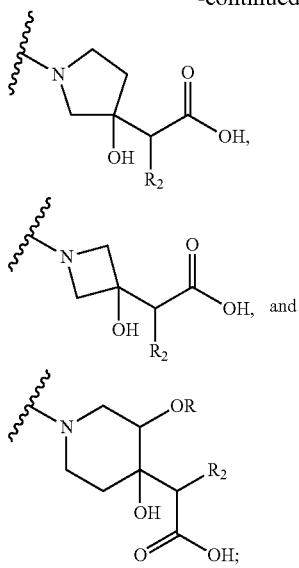

In certain embodiments, the invention relates to any one of the aforementioned compounds, wherein X is $C(R_c)$.

In certain embodiments, the invention relates to any one of the aforementioned compounds, wherein $R_c$ is H, alkyl, aryl, OH, or halide. In certain embodiments, the invention relates to any one of the aforementioned compounds, wherein $R_c$ is H.

In certain embodiments, the invention relates to any one of the aforementioned compounds, wherein $R_d$ is H. In certain embodiments, the invention relates to any one of the aforementioned compounds, wherein $R_d$ is $(C_1$-$C_6)$alkyl. In certain embodiments, the invention relates to any one of the aforementioned compounds, wherein $R_d$ is methyl. In certain embodiments, the invention relates to any one of the aforementioned compounds, wherein $R_d$ is ethyl.

In certain embodiments, the invention relates to any one of the aforementioned compounds, wherein $R_2$ is H, alkyl, substituted or unsubstituted aryl, substituted or unsubstituted heteroaryl, cycloalkyl, -alkylene-alkoxy, alkoxy, OH, -alkylene-aryl, or heterocycloalkyl. In certain embodiments, the invention relates to any one of the aforementioned compounds, wherein $R_2$ is substituted or unsubstituted phenyl.

In certain embodiments, the invention relates to any one of the aforementioned compounds, wherein $R_2$ is —N(R)C(O)$R_4$, —N(R)SO$_2$R$_4$—, —N(R)-aryl, or —N(R)-heteroaryl.

In certain embodiments, the invention relates to any one of the aforementioned compounds, wherein $R_2$ is —N(H)-2-pyridinyl, or —N(H)-2,4-pyrimidinyl. In certain embodiments, the invention relates to any one of the aforementioned compounds, wherein $R_2$ is —N(H)C(O)Me.

In certain embodiments, the invention relates to any one of the aforementioned compounds, wherein $R_2$ is H, $(C_1$-$C_4)$alkyl, cyclopropyl, CH$_2$OMe, phenyl, —CH$_2$Ph, pyridinyl, or indolyl.

In certain embodiments, the invention relates to any one of the aforementioned compounds, wherein $R_2$ is H. In certain embodiments, the invention relates to any one of the aforementioned compounds, wherein $R_2$ is Me. In certain embodiments, the invention relates to any one of the aforementioned compounds, wherein $R_2$ is unsubstituted phenyl. In certain embodiments, the invention relates to any one of the aforementioned compounds, wherein $R_2$ is substituted phenyl. In certain embodiments, the invention relates to any one of the aforementioned compounds, wherein the substituted phenyl is substituted with one or more independent instances of alkoxy, OH, halide, —N(H)C(O)alkyl, —C(O)NH$_2$, or —C(O)alkyl. In certain embodiments, the invention relates to any one of the aforementioned compounds, wherein the substituted phenyl is substituted with at least one halide. In certain embodiments, the invention relates to any one of the aforementioned compounds, wherein the halide is Cl. In certain embodiments, the invention relates to any one of the aforementioned compounds, wherein $R_2$ is unsubstituted pyridinyl. In certain embodiments, the invention relates to any one of the aforementioned compounds, wherein $R_2$ is substituted pyridinyl. In certain embodiments, the invention relates to any one of the aforementioned compounds, wherein the substituted pyridinyl is substituted with NH$_2$, or OH. In certain embodiments, the invention relates to any one of the aforementioned compounds, wherein $R_2$ is

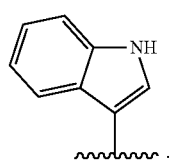 [SMILES: *c1c[nH]c2ccccc12]

In certain embodiments, the invention relates to any one of the aforementioned compounds, wherein each occurrence of $R_3$ is independently alkyl, halide, CF$_3$, alkylene-alkoxy, aryl, hydroxyl, alkoxy, NO$_2$, or NH$_2$.

In certain embodiments, the invention relates to any one of the aforementioned compounds, wherein each occurrence of $R_3$ is independently alkyl, halide, alkoxy, CF$_3$, OH, NO$_2$, or NH$_2$.

In certain embodiments, the invention relates to any one of the aforementioned compounds, wherein at least one instance of $R_3$ is alkyl. In certain embodiments, the invention relates to any one of the aforementioned compounds, wherein at least one instance of $R_3$ is methyl. In certain embodiments, the invention relates to any one of the aforementioned compounds, wherein at least one instance of $R_3$ is halide. In certain embodiments, the invention relates to any one of the aforementioned compounds, wherein at least one instance of $R_3$ is iodo, bromo, chloro, or fluoro.

In certain embodiments, the invention relates to any one of the aforementioned compounds, wherein at least one instance of $R_3$ is alkoxy. In certain embodiments, the invention relates to any one of the aforementioned compounds, wherein at least one instance of $R_3$ is MeOH. In certain embodiments, the invention relates to any one of the aforementioned compounds, wherein at least one instance of $R_3$ is NH$_2$.

In certain embodiments, the invention relates to any one of the aforementioned compounds, wherein $R_4$ is alkyl, cycloalkyl, heterocycloalkyl, aryl, heteroaryl, -alkylene-heterocyclyl, -alkylene-N(R)C(O)$R_5$, or -alkylene-N(R)—SO$_2$Me;

In certain embodiments, the invention relates to any one of the aforementioned compounds, wherein R₄ is Me,

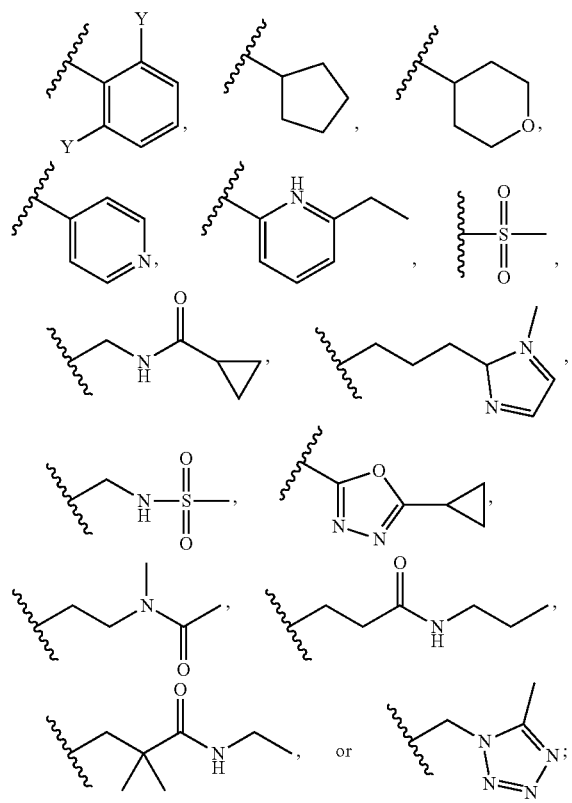

and Y is H, F, or Cl.

In certain embodiments, the invention relates to any one of the aforementioned compounds, wherein R₅ is alkyl. In certain embodiments, the invention relates to any one of the aforementioned compounds, wherein R₅ is methyl. In certain embodiments, the invention relates to any one of the aforementioned compounds, wherein R₅ is cycloalkyl. In certain embodiments, the invention relates to any one of the aforementioned compounds, wherein R₅ is cyclopropyl.

In certain embodiments, the invention relates to any one of the aforementioned compounds, wherein R₆ is alkyl. In certain embodiments, the invention relates to any one of the aforementioned compounds, wherein R₆ is methyl. In certain embodiments, the invention relates to any one of the aforementioned compounds, wherein R₆ is H.

In certain embodiments, the invention relates to any one of the aforementioned compounds, wherein the optional substituent, when present, is selected from the group consisting of alkoxy, alkyl ester, alkylcarbonyl, hydroxyalkyl, cyano, halo, amino, amido, cycloalkyl, aryl, haloalkyl, nitro, hydroxy, alkoxy, aryloxy, alkyl, alkylthio, and cyanoalkyl.

In certain embodiments, the invention relates to any one of the aforementioned compounds, wherein the compound is a pharmaceutically acceptable salt.

In certain embodiments, the invention relates to a compound selected from the group consisting of:

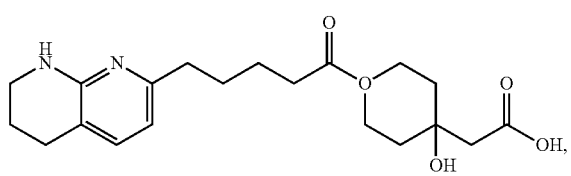

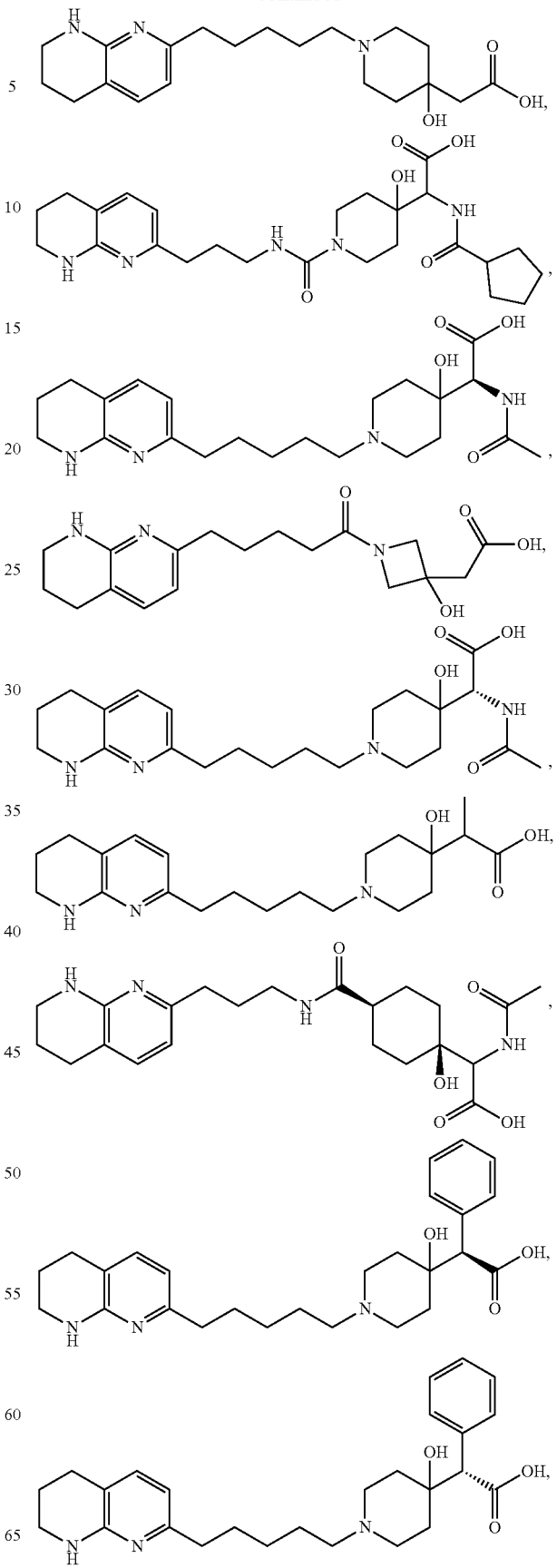

-continued
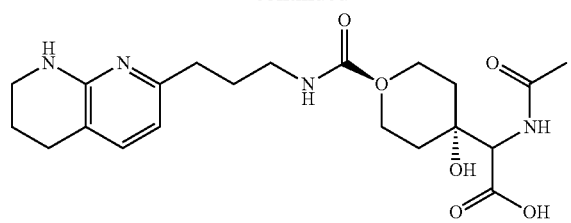
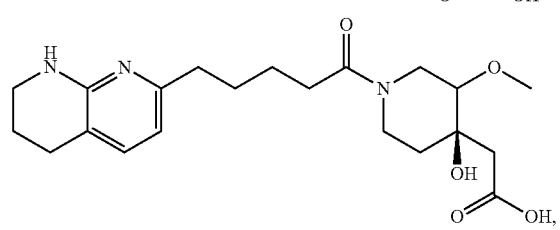
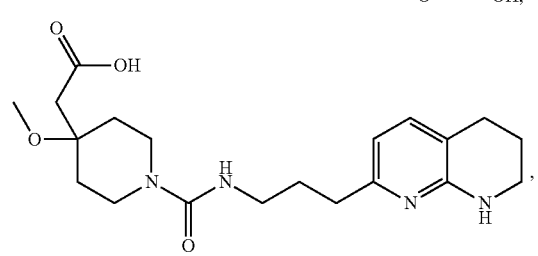
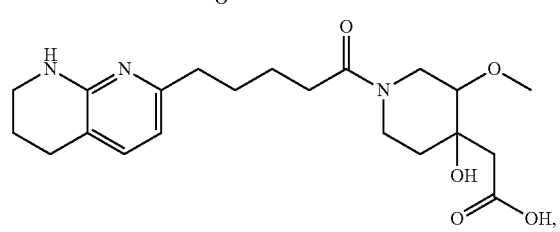
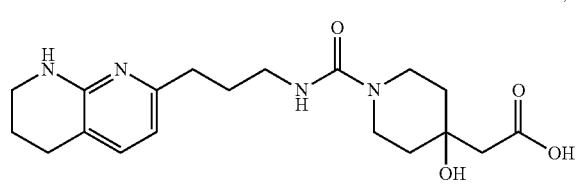
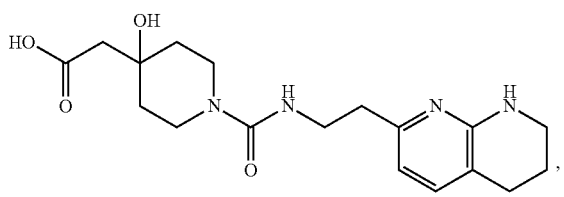
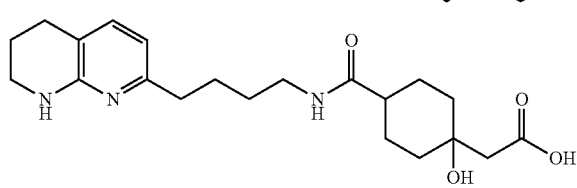
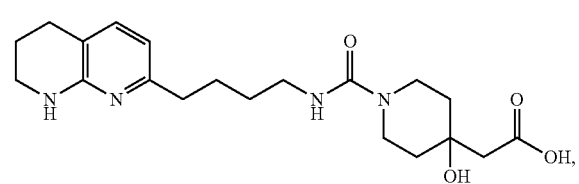
-continued
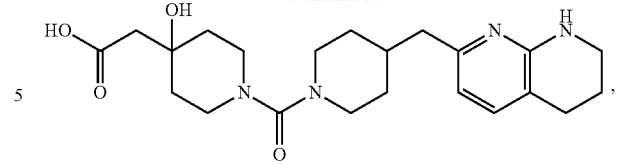
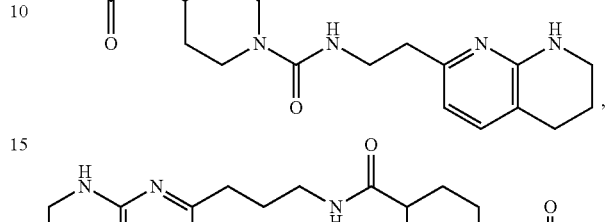
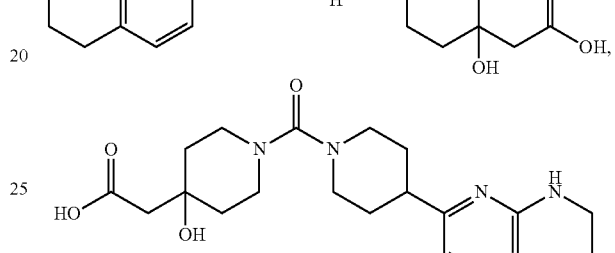
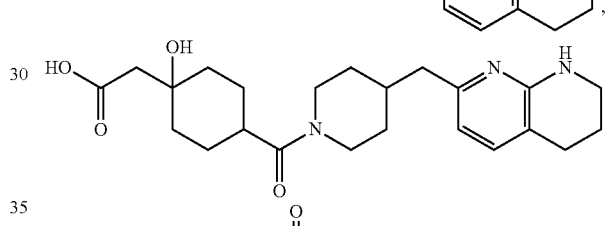
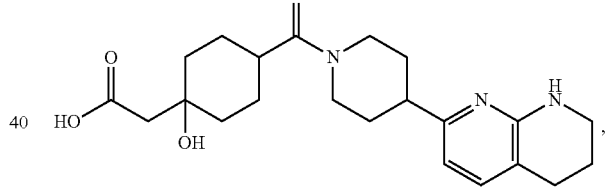
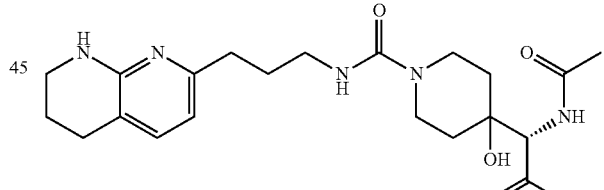
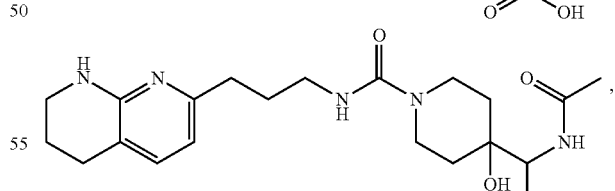
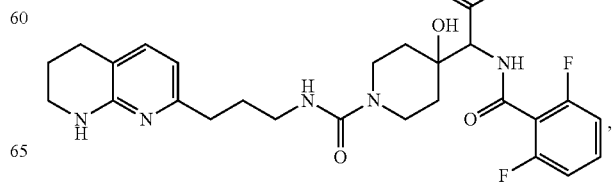

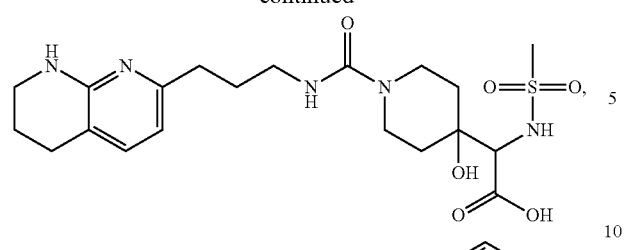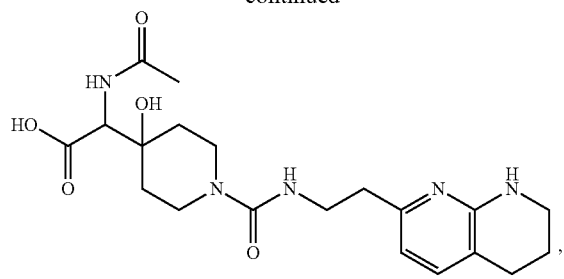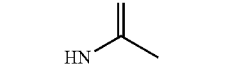

33
-continued
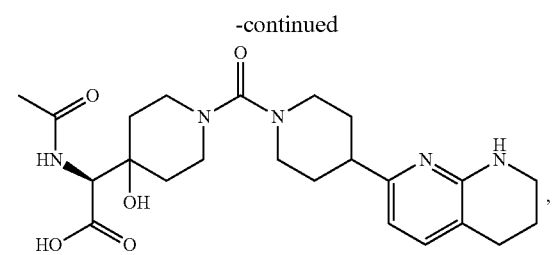
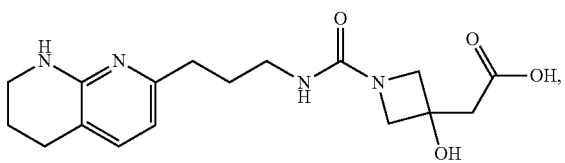
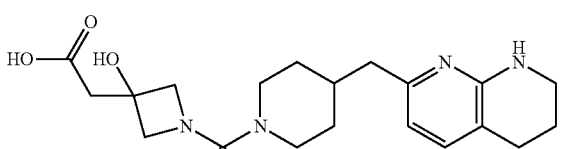
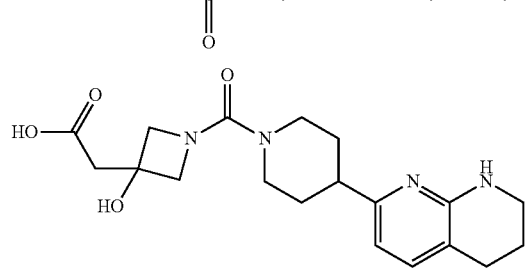
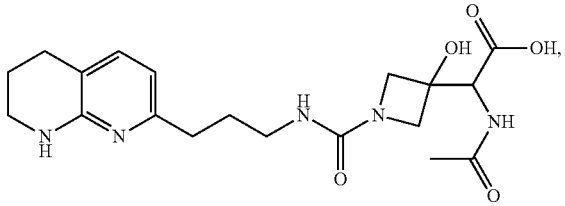
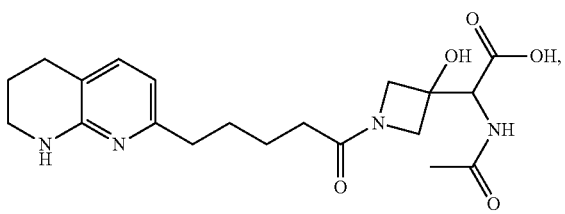
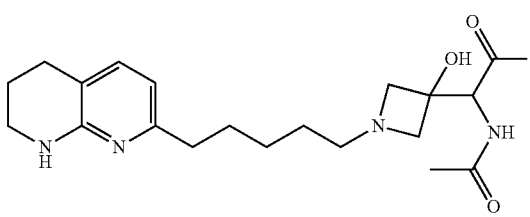
34
-continued
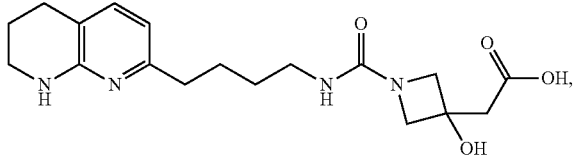
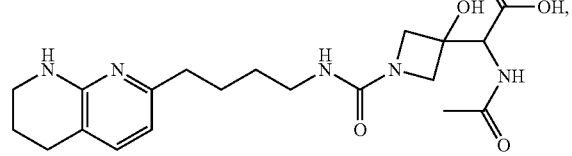
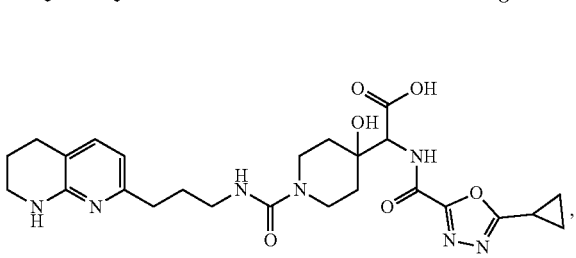
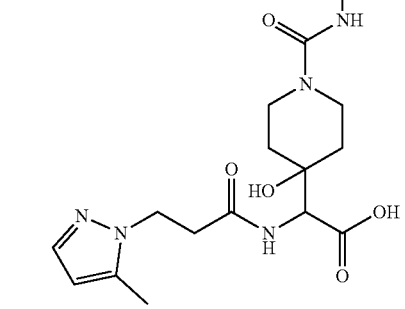
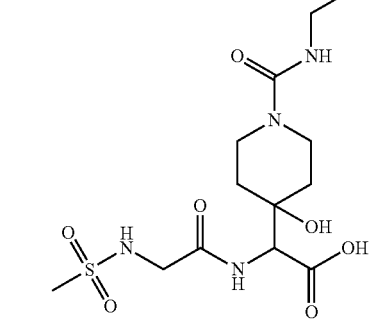

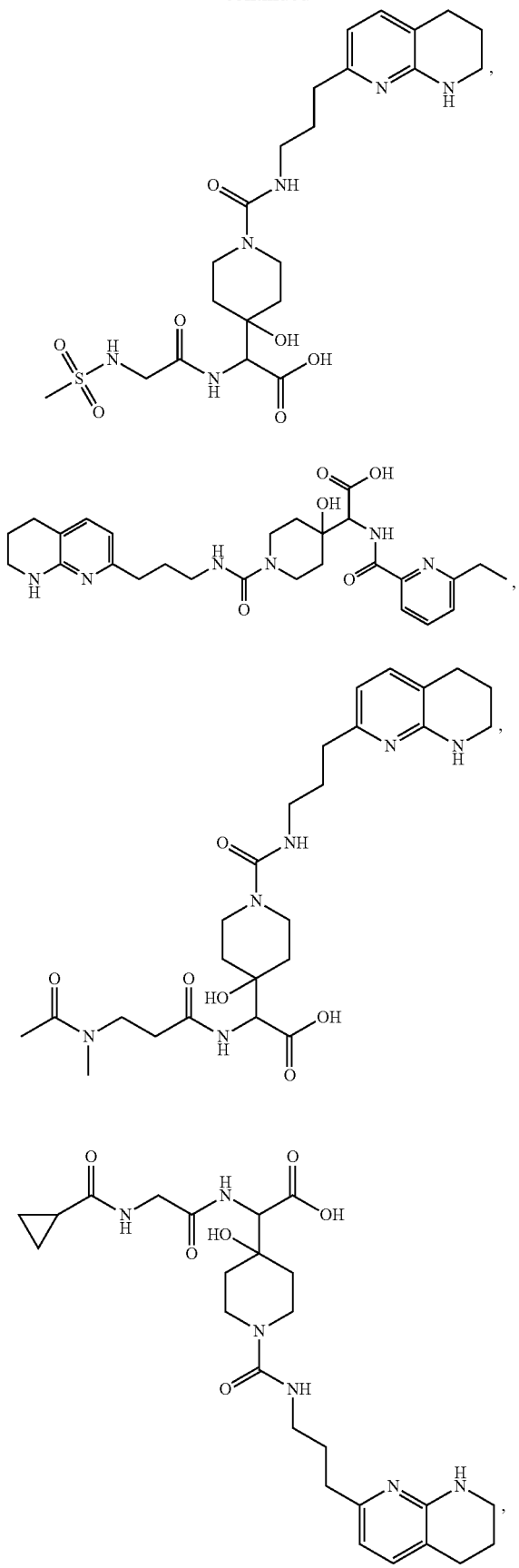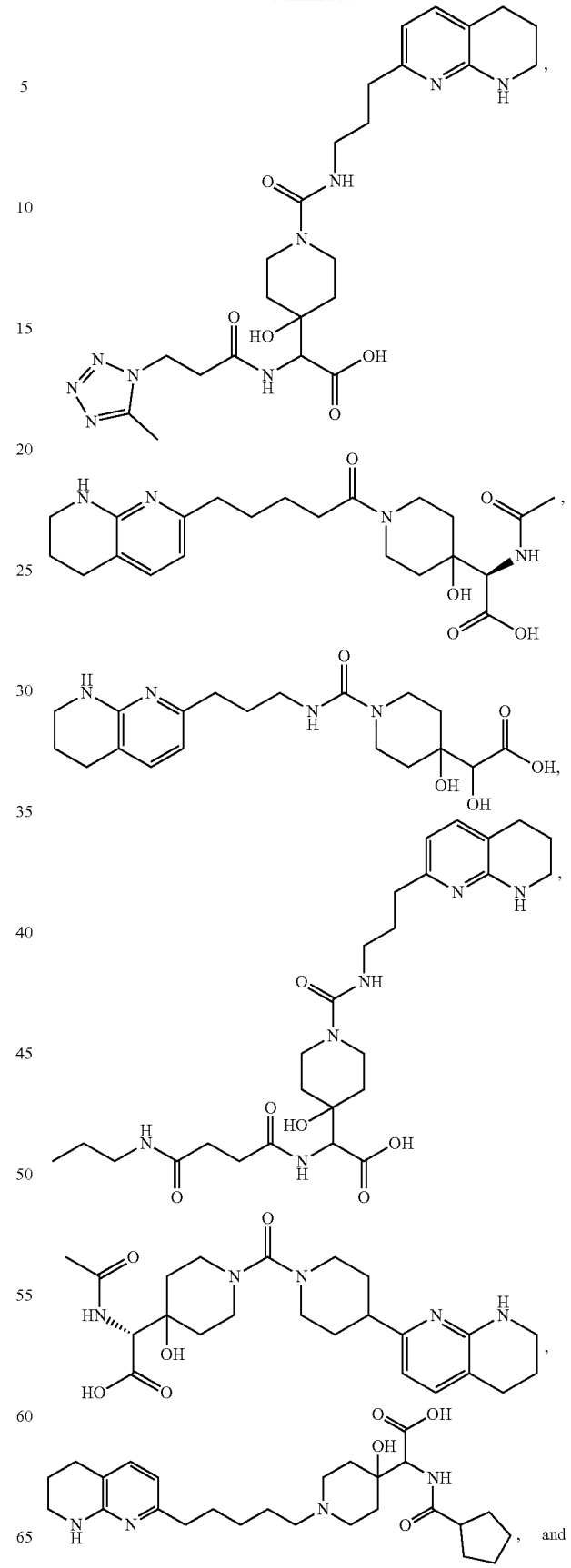

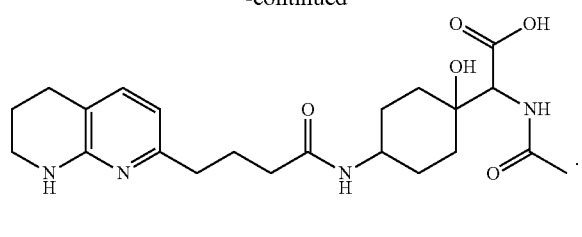
In certain embodiments, the invention relates to a compound selected from the group consisting of:
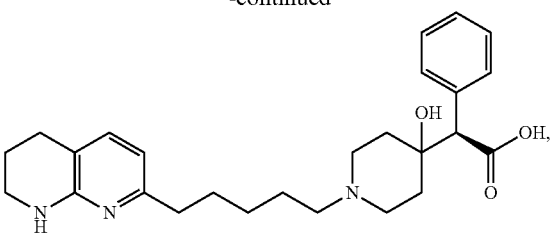
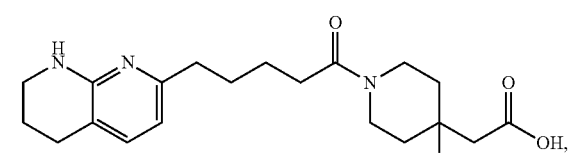
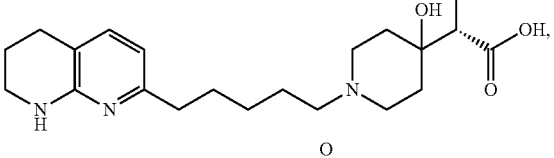
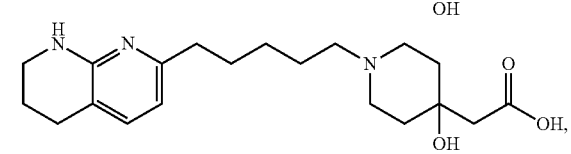
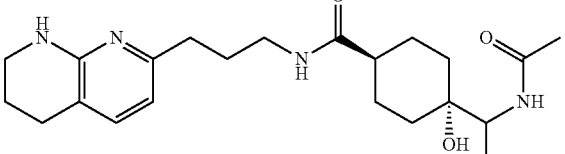
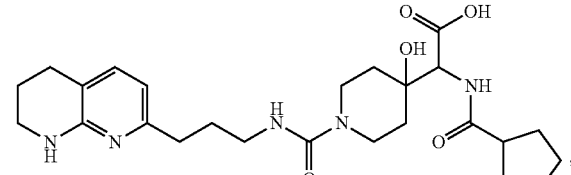
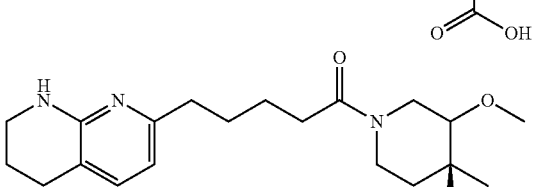
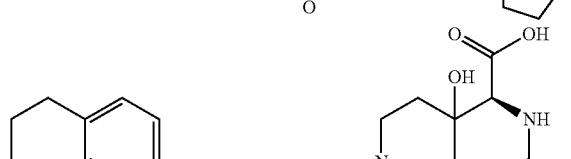
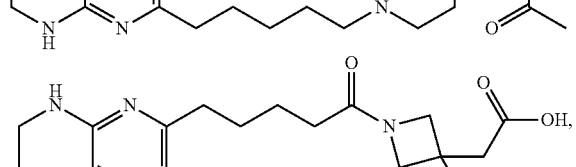
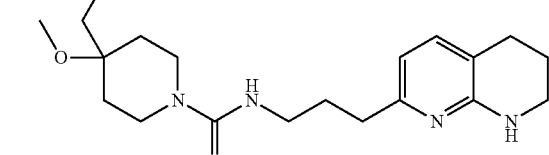
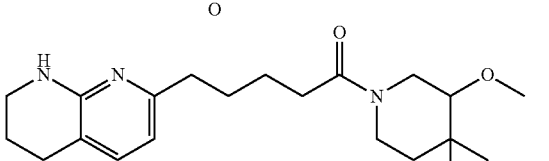
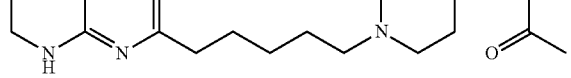
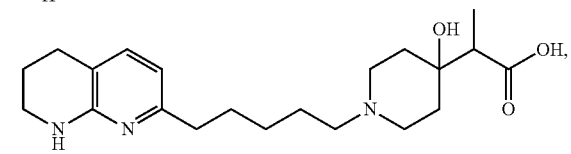
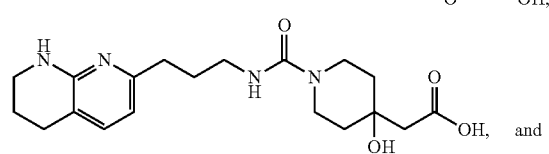
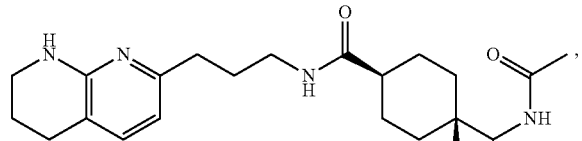
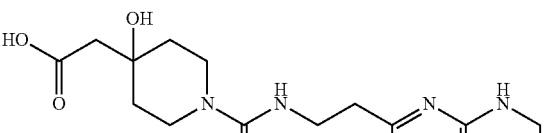, and
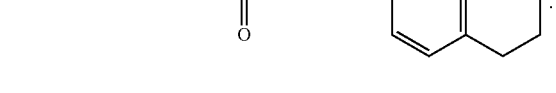.

In certain embodiments, the invention relates to a compound selected from the group consisting of:
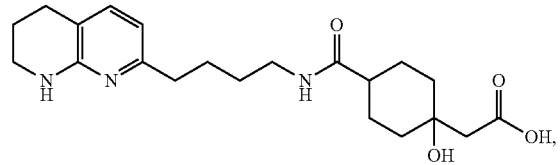
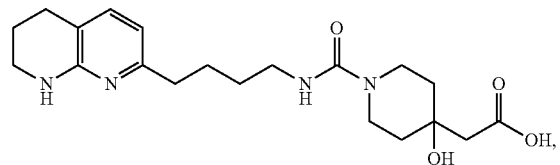
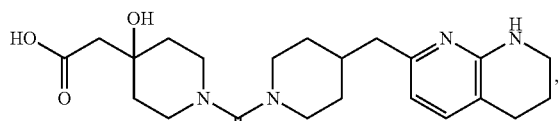
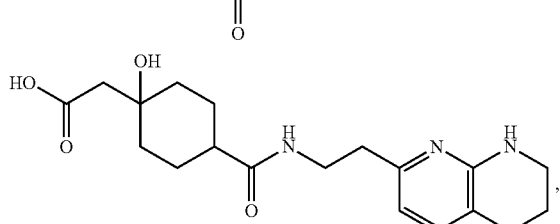
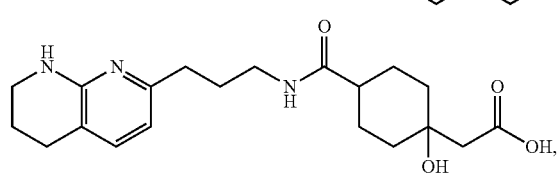
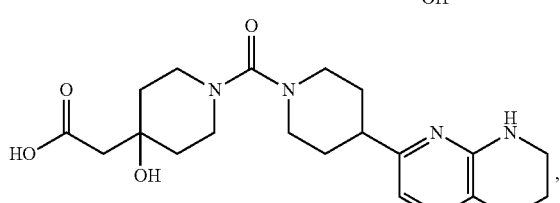
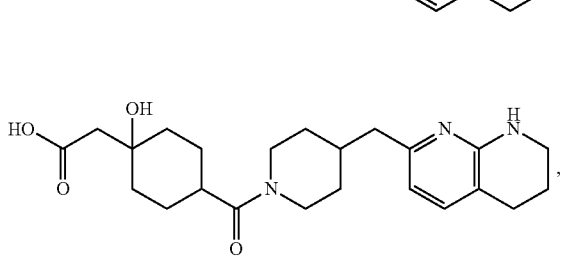
-continued
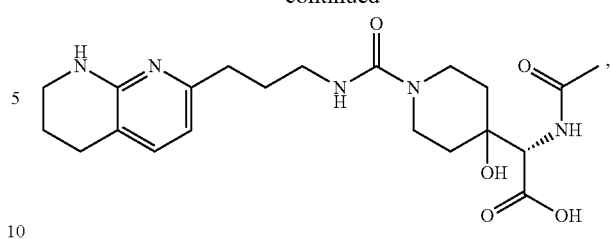
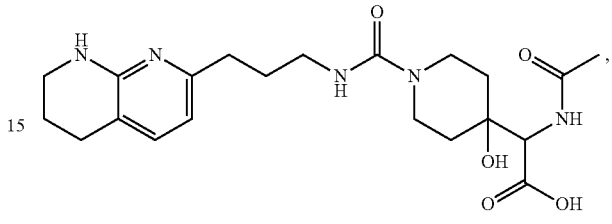
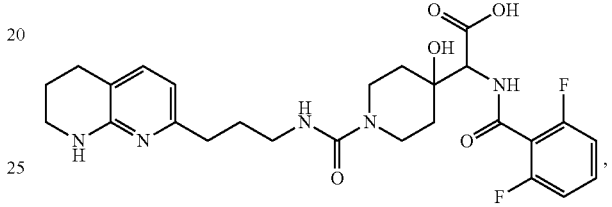
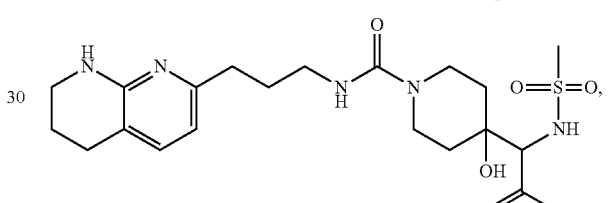
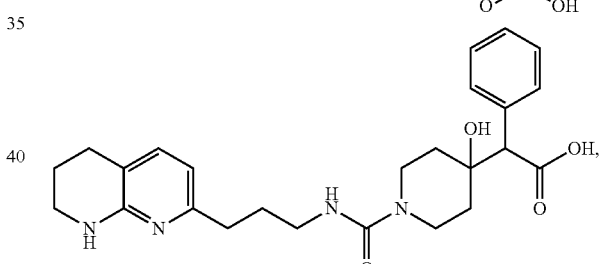
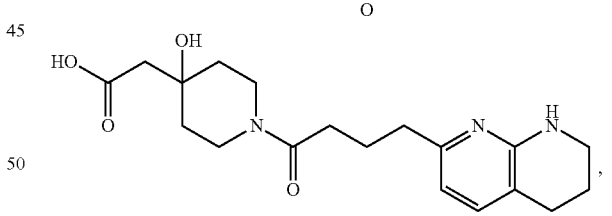
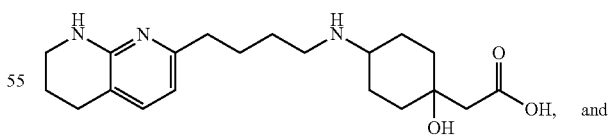
and
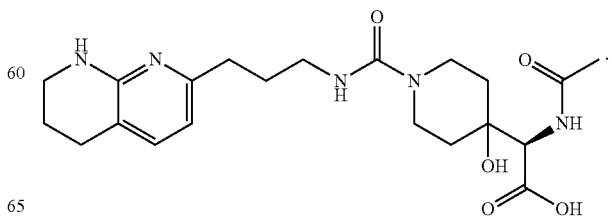

In certain embodiments, the invention relates to a compound selected from the group consisting of:
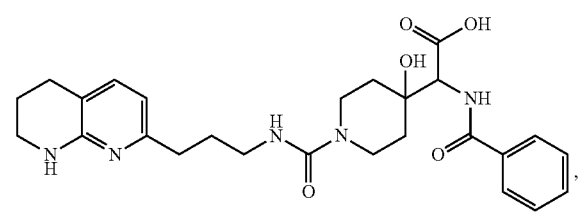,
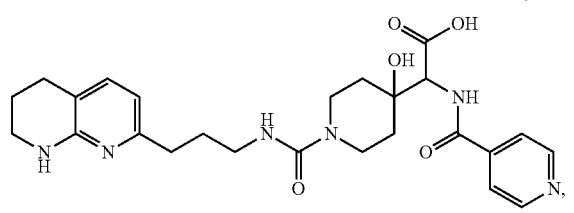,
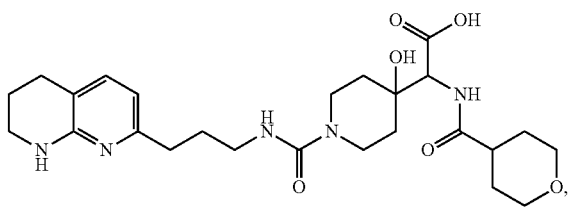,
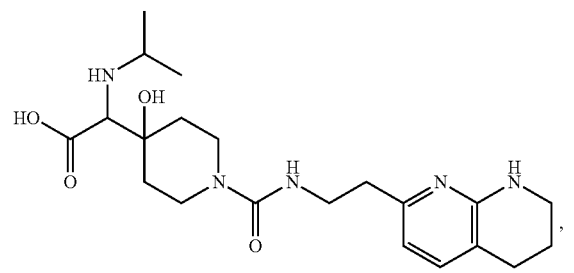,
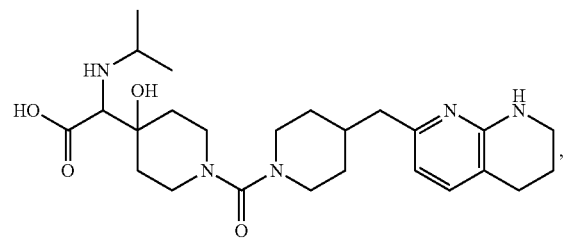,
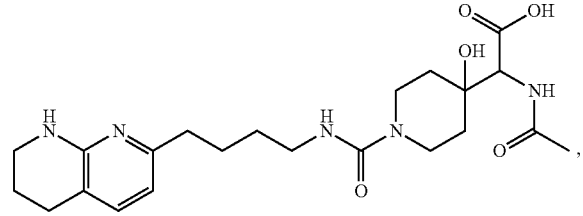,
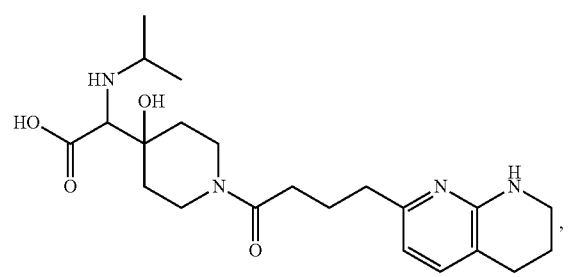,
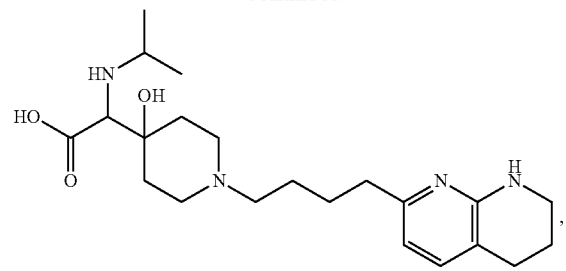,
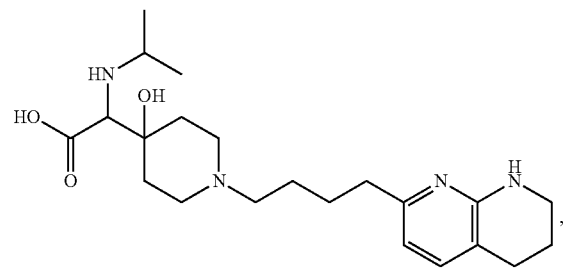 [SMILES: CC(C)NC(C(=O)O)C1(O)CCN(CCCCc2ccc3c(n2)NCCC3)CC1],
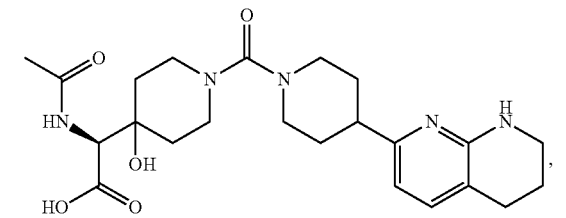,
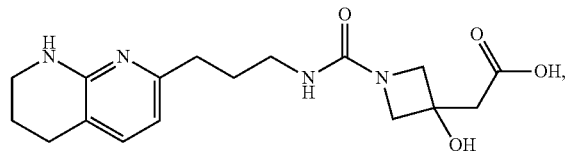,
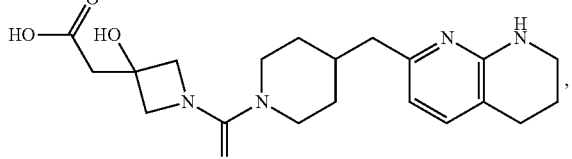,
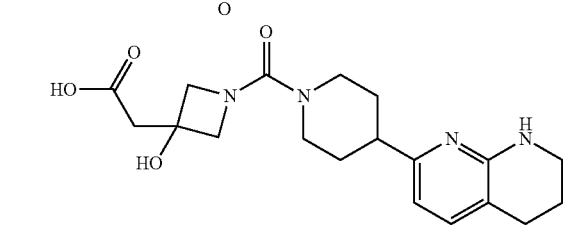,
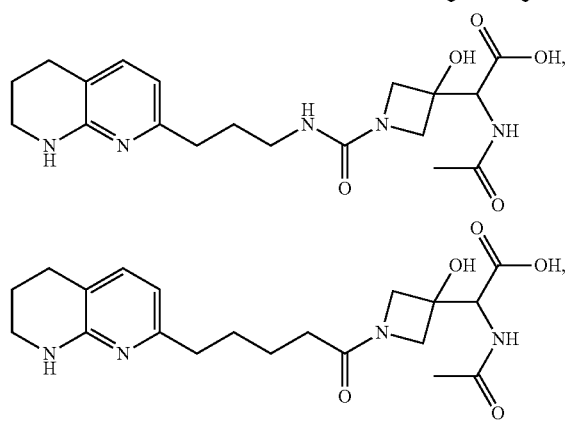

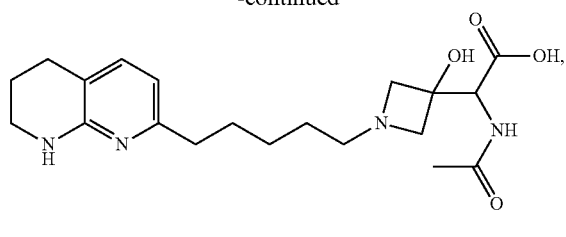
In certain embodiments, the invention relates to a compound selected from the group consisting of:
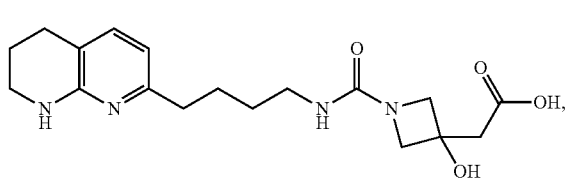
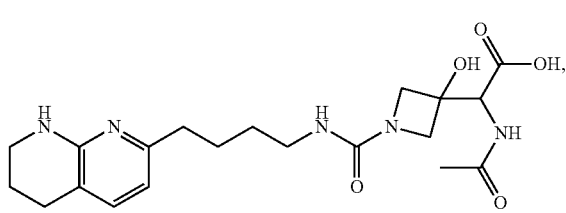
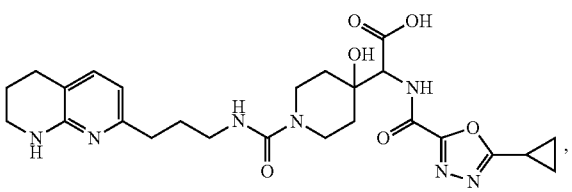
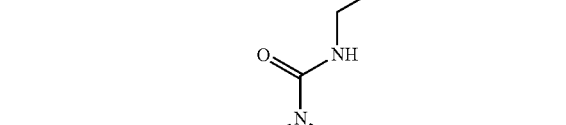
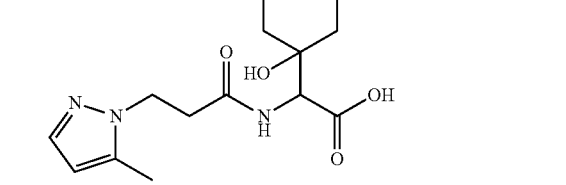
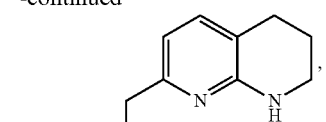
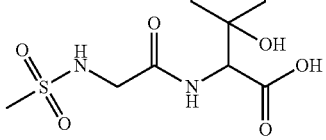
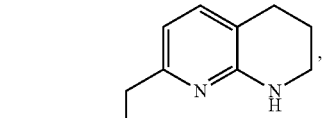
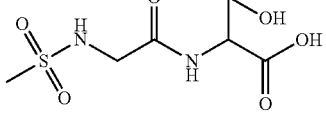
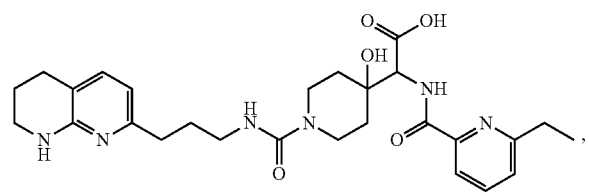
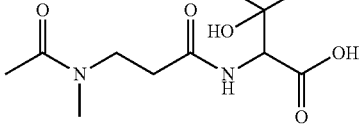

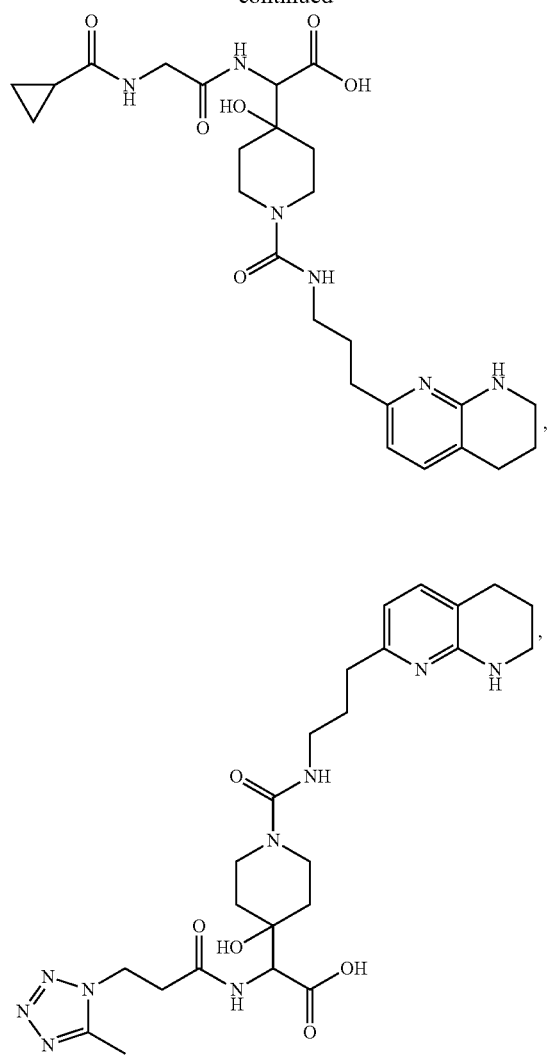
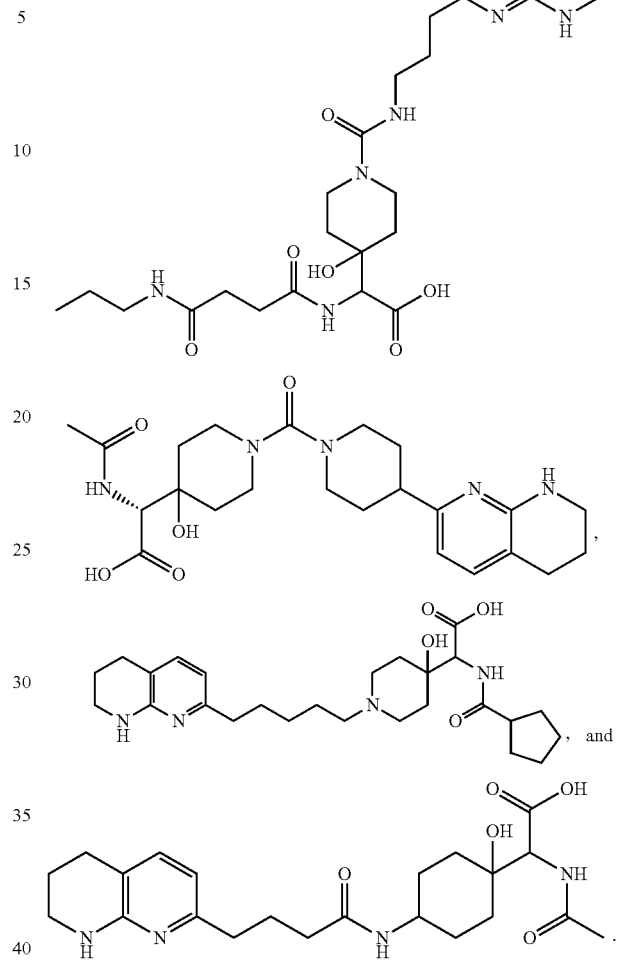
In certain embodiments, the invention relates to a compound selected from the group consisting of:
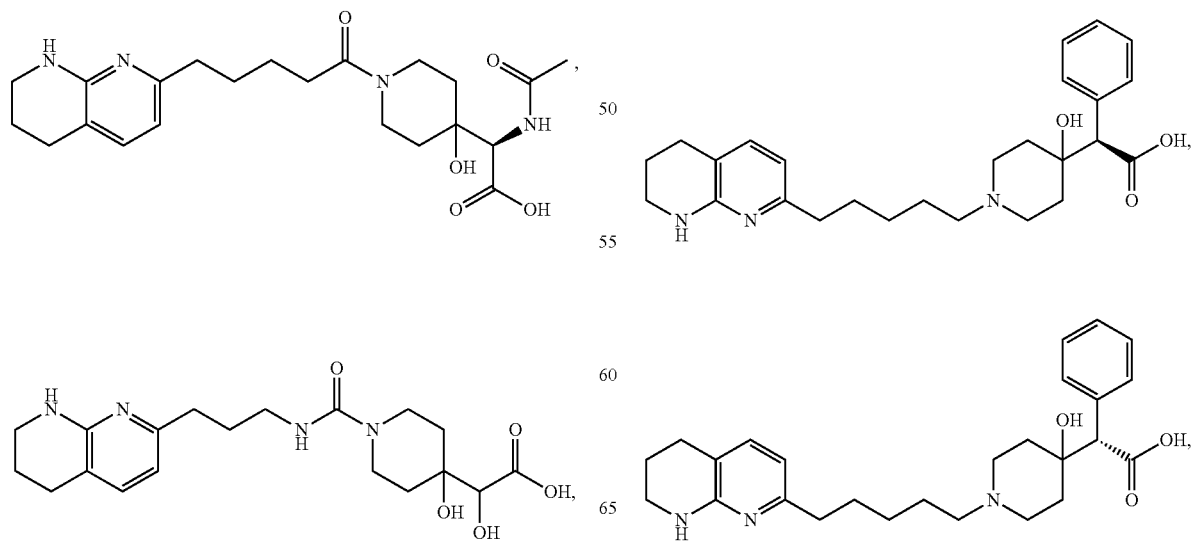

-continued

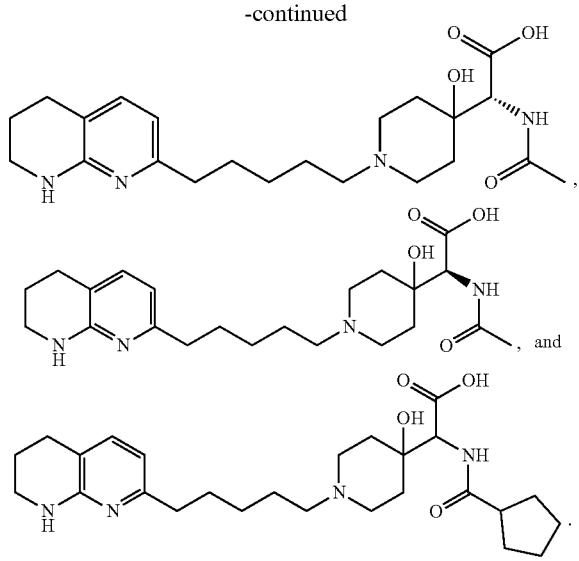

Exemplary Pharmaceutical Compositions

In certain embodiments, the invention relates to a pharmaceutical composition comprising any one of the aforementioned compounds and a pharmaceutically acceptable carrier.

Patients, including but not limited to humans, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

In certain embodiments, the mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose or sweetener as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antivirals, including but not limited to nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, carriers include physiological saline and phosphate buffered saline (PBS).

In certain embodiments, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Exemplary Methods of the Invention

In certain embodiments, the invention relates to a method of treating a disease or a condition selected from the group consisting of idiopathic pulmonary fibrosis, diabetic nephropathy, focal segmental glomerulosclerosis, chronic kidney disease, nonalcoholic steatohepatitis, primary biliary cholangitis, primary sclerosing cholangitis, solid tumors, hematological tumors, organ transplant, Alport syndrome, interstitial lung disease, radiation-induced fibrosis, bleomycin-induced fibrosis, asbestos-induced fibrosis, flu-induced fibrosis, coagulation-induced fibrosis, vascular injury-induced fibrosis, aortic stenosis, and cardiac fibrosis, comprising the step of: administering to a subject in need thereof a therapeutically effective amount of any one of the aforementioned compounds.

In certain embodiments, the compound administered is selected from the group consisting of:

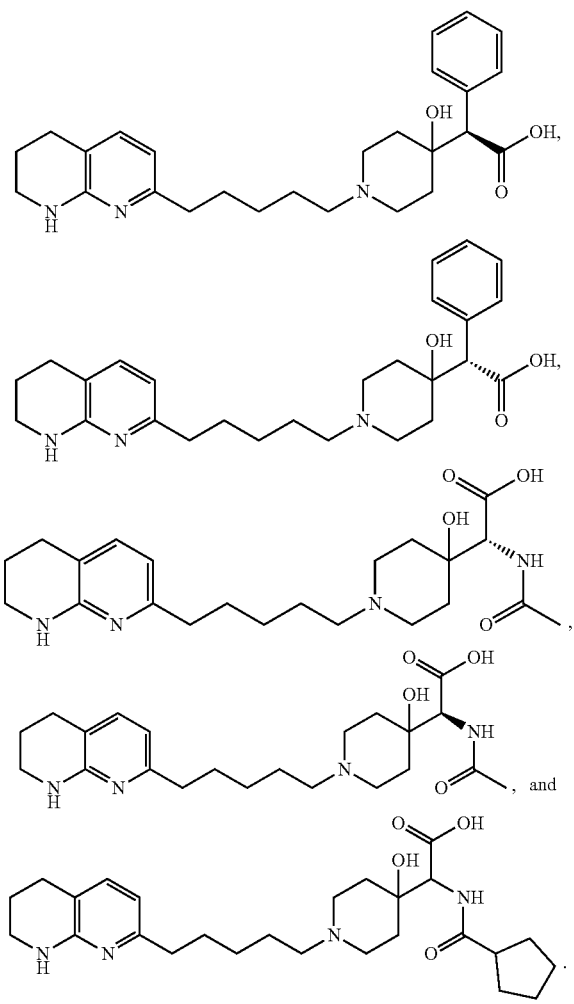

In certain embodiments, the invention relates to any one of the aforementioned methods, wherein the disease or condition is a solid tumor (sarcomas, carcinomas, and lymphomas). Exemplary tumors that may be treated in accordance with the invention include e.g., Ewing's sarcoma, rhabdomyosarcoma, osteosarcoma, myelosarcoma, chondrosarcoma, liposarcoma, leiomyosarcoma, soft tissue sarcoma, non-small cell lung cancer, small cell lung cancer, bronchus cancer, prostate cancer, breast cancer, pancreatic cancer, gastrointestinal cancer, colon cancer, rectum cancer, colon carcinoma, colorectal adenoma, thyroid cancer, liver cancer, intrahepatic bile duct cancer, hepatocellular cancer, adrenal gland cancer, stomach cancer, gastric cancer, glioma (e.g., adult, childhood brain stem, childhood cerebral astrocytoma, childhood visual pathway and hypothalamic), glioblastoma, endometrial cancer, melanoma, kidney cancer, renal pelvis cancer, urinary bladder cancer, uterine corpus, uterine cervical cancer, vaginal cancer, ovarian cancer, multiple myeloma, esophageal cancer, brain cancer (e.g., brain stem glioma, cerebellar astrocytoma, cerebral astrocytoma/malignant glioma, ependymoma, meduloblastoma, supratentorial primitive neuroectodermal tumors, visual pathway and hypothalamic glioma), lip and oral cavity and pharynx, larynx, small intestine, melanoma, villous colon adenoma, a neoplasia, a neoplasia of epithelial character, lymphomas (e.g., AIDS-related, Burkitt's, cutaneous T-cell, Hodgkin, non-Hodgkin, and primary central nervous system), a mammary carcinoma, basal cell carcinoma, squamous cell carcinoma, actinic keratosis, tumor diseases, including solid tumors, a tumor of the neck or head, polycythemia vera, essential thrombocythemia, myelofibrosis with myeloid metaplasia, Waldenstrom's macroglobulinemia, adrenocortical carcinoma, AIDS-related cancers, childhood cerebellar astrocytoma, childhood cerebellar astrocytoma, basal cell carcinoma, extrahepatic bile duct cancer, malignant fibrous histiocytoma bone cancer, bronchial adenomas/carcinoids, carcinoid tumor, gastrointestinal carcinoid tumor, primary central nervous system, cerebellar astrocytoma, childhood cancers, ependymoma, extracranial germ cell tumor, extragonadal germ cell tumor, extrahepatic bile duct cancer, intraocular melanoma eye cancer, retinoblastoma eye cancer, gallbladder cancer, gastrointestinal carcinoid tumor, germ cell tumors (e.g., extracranial, extragonadal, and ovarian), gestational trophoblastic tumor, hepatocellular cancer, hypopharyngeal cancer, hypothalamic and visual pathway glioma, islet cell carcinoma (endocrine pancreas), laryngeal cancer, malignant fibroushistiocytoma of bone/osteosarcoma, meduloblastoma, mesothelioma, metastatic squamous neck cancer with occult primary, multiple endocrine neoplasia syndrome, multiple myeloma/plasma cell neoplasm, mycosis fungoides, nasal cavity and paranasal sinus cancer, nasopharyngeal cancer, neuroblastoma, oral cancer, oropharyngeal cancer, ovarian epithelial cancer, ovarian germ cell tumor, ovarian low malignant potential tumor, islet cell pancreatic cancer, parathyroid cancer, pheochromocytoma, pineoblastoma, pituitary tumor, pleuropulmonary blastoma, ureter transitional cell cancer, retinoblastoma, rhabdomyosarcoma, salivary gland cancer, Sezary syndrome, non-melanoma skin cancer, Merkel cell carcinoma, squamous cell carcinoma, testicular cancer, thymoma, gestational trophoblastic tumor, and Wilms' tumor.

In certain embodiments, the invention relates to any one of the aforementioned methods, wherein the disease is disease or condition is a hematological tumor. Exemplary hematological tumors that may be treated in accordance with the invention include e.g., acute lymphocytic leukemia, acute myelogenous leukemia, chronic lymphocytic leukemia, chronic myelogenous leukemia, Hodgkin lymphoma, non-Hodgkin lymphoma, and multiple myeloma.

In certain embodiments, the invention relates to any one of the aforementioned methods, wherein the disease or condition is selected from the group consisting of idiopathic pulmonary fibrosis, systemic sclerosis associated interstitial lung disease, myositis associated interstitial lung disease, systemic lupus erythematosus associated interstitial lung disease, rheumatoid arthritis, and associated interstitial lung disease.

In certain embodiments, the invention relates to any one of the aforementioned methods, wherein the disease or condition is selected from the group consisting of diabetic nephropathy, focal segmental glomerulosclerosis, and chronic kidney disease.

In certain embodiments, the invention relates to any one of the aforementioned methods, wherein the disease or condition is selected from the group consisting of nonalcoholic steatohepatitis, primary biliary cholangitis, and primary sclerosing cholangitis.

In certain embodiments, the invention relates to any one of the aforementioned methods, wherein the subject is a mammal. In certain embodiments, the invention relates to any one of the aforementioned methods, wherein the subject is human.

EXEMPLIFICATION

The invention now being generally described, it will be more readily understood by reference to the following examples, which are included merely for purposes of illustration of certain aspects and embodiments of the present invention, and are not intended to limit the invention.

General Schemes and Procedures for the Preparation of Tertiary Alcohol Compounds The moieties R and $R_1$ are appropriate ester protecting groups; $R_2$, $R_3$, $R_4$, $R_5$ and $R_6$ are H or an appropriate substituent; L is an appropriate linker; and each instance of a independently equals 0 or 1.

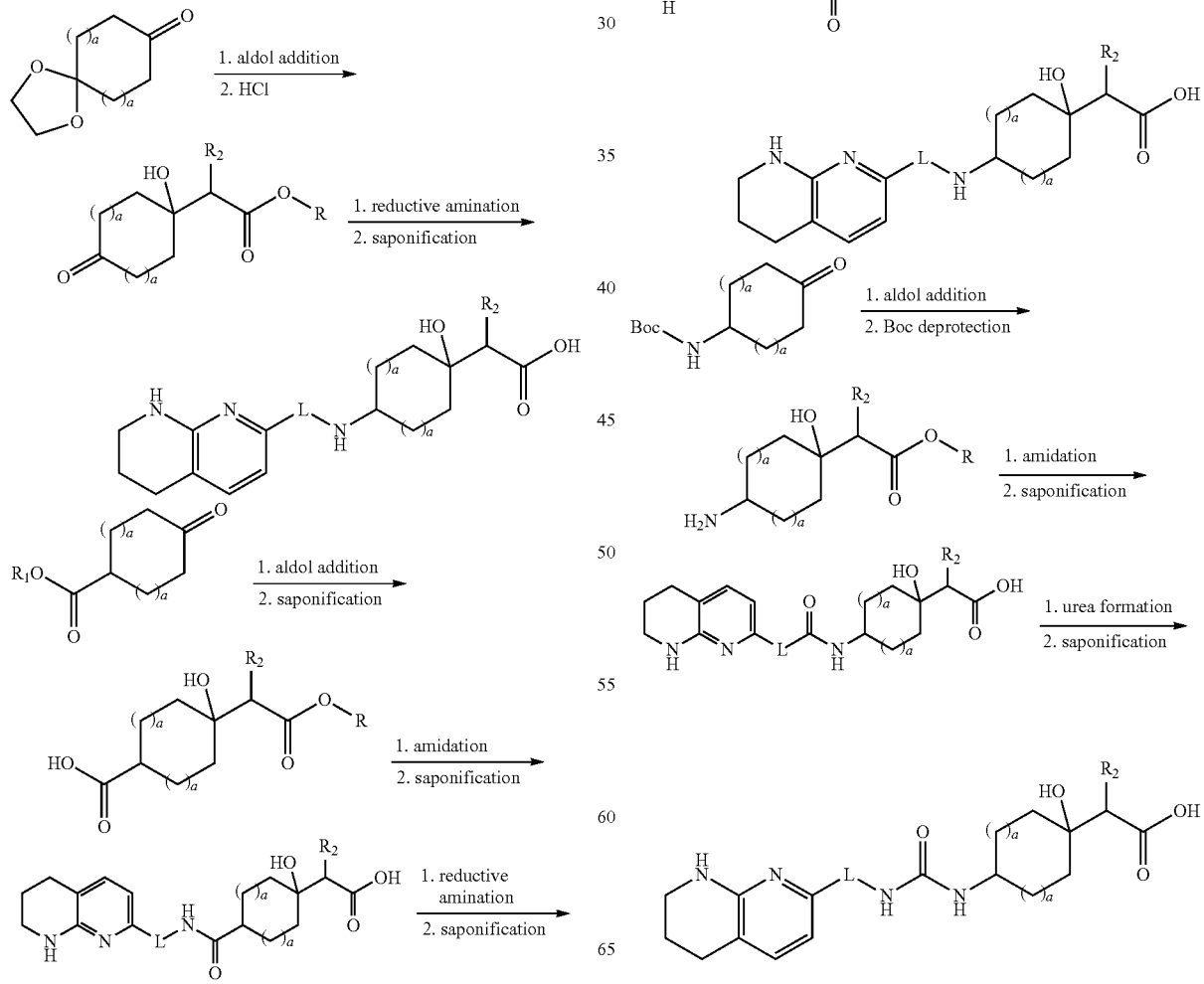

General Procedures
Reductive Amination:

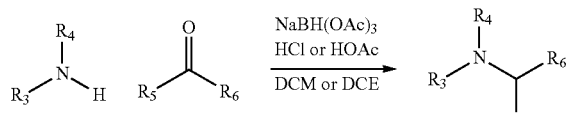

A mixture of amine (1 equiv.), aldehyde or ketone (1-1.2 equiv.), NaBH(OAc)₃ (2-3 equiv.) and HCl or acetic acid (0.1 to 2 equiv.) in DCM or DCE (5-10 mL/mmole amine) was stirred at room temperature from 1 to 16 hours until complete by LC/MS. The reaction was concentrated in vacuo or worked up (diluted with water and extracted with DCM; combined extracts dried over Na₂SO₄, filtered and concentrated), and the residue was purified by silica gel column to give the desired amine product.

Amide Bond Formation:

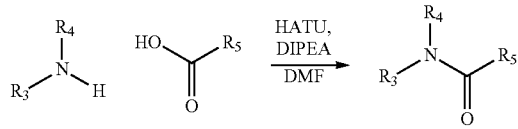

A mixture of carboxylic acid (1 equiv.), amine (0.5-2 equiv.), HATU (1-2 equiv.) and DIEA (2-5 equiv.) in DMF or DCM (5-10 mL/mmole amine) was stirred at room temperature for 16 hours or until complete by LC/MS. The reaction was concentrated in vacuo, and the residue was purified by silica gel column to give the desired amide product.

Urea Formation:

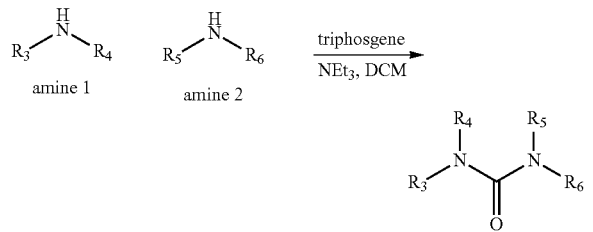

To a solution of amine 1 (1 equiv.) and triethylamine (3-5 equiv.) in DCM (5-10 mL/mmole amine 1) at 0° C. was added triphosgene (0.4-0.5 equiv.). The reaction was stirred for 30 min to 1 hour, and then amine 2 (0.5-1.5 equiv.) in DCM (1-2 mL/mmol amine 1) was added. The reaction was stirred at room temperature for 2-16 hours, then concentrated under vacuum. The residue was purified by silica gel column to give the desired urea.

Boc Deprotection:

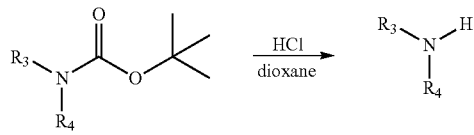

Boc-protected amine (1 equiv.) was treated with HCl (5-20 equiv.) in dioxane (5-20 mL/mmol amine) at room temperature for 1-4 hours. The reaction was concentrated in vacuo, and the amine product was used crude or after purification by silica gel column.

Aldol Addition:

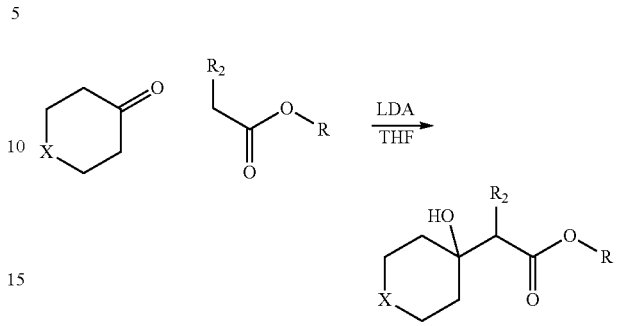

A solution of substituted acetate (1 equiv.) in THF (2-10 mL/mmol acetate) at −78° C. was added LDA (1-1.5 equiv., 2 M in THF/heptane/ethylbenzene). The reaction was stirred for 30 min, and then ketone (0.75-1 equiv.) in THF (1-2 mL/mmol acetate) was added. The reaction was stirred at −78° C. for 1-2 hours, then quenched with saturated aqueous NH₄Cl and extracted with EtOAc (2-3×). The combined organic extracts were dried over Na₂SO₄, filtered and concentrated in vacuo. The reside was purified by silica gel column to give the desired aldol addition product.

Saponification:

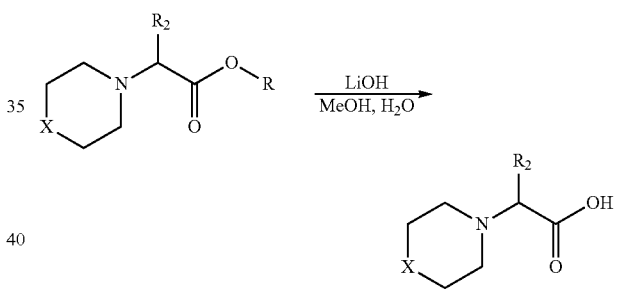

The ester (1 equiv.) was treated with LiOH—H₂O (3-5 equiv.) in MeOH (3-10 mL/mmol ester) and water (3-10 mL/mmol ester) at room temperature for 1-16 hours. The reaction was concentrated in vacuo, and the residue was purified by prep HPLC to give the desired carboxylic acid product.

Analytical Methods
LCMS Analytical Methods

Final compounds were analyzed using LC/MS conditions, with UV detector monitoring at 214 nm and 254 nm, and mass spectrometry scanning 110-800 amu in ESI+ ionization mode.

LC/MS A: column: XBridge C18, 4.6×50 mm, 3.5 µm; mobile phase: A water (10 mM ammonium hydrogen carbonate), B CH3CN; gradient: 5%-95% B in 1.4 min, then 1.6 min hold; flow rate: 1.8 mL/min; oven temperature 50° C.

LC/MS B: column: SunFire C18, 4.6×50 mm, 3.5 µm; mobile phase: A water (0.01% TFA), B CH3CN; gradient: 5%-95% B in 1.5 min, then 1.5 min hold; flow rate: 2.0 mL/min; oven temperature 50° C.

LC/MS C: column: XBridge C18, 4.6×50 mm, 3.5 µm; mobile phase: A water (10 mM ammonium hydrogen carbonate), B CH3CN; gradient: 5%-95% B in 1.5 min, then 1.5 min hold; flow rate: 1.8 mL/min; oven temperature 50° C.

LC/MS D: column: Poroshell 120 EC-C138, 4.6×30 mm, 2.7 μm; mobile phase: A water (0.01% TFA), B CH3CN (0.01% TFA); gradient: 5%-95% B in 1.2 min, then 1.8 min hold; flow rate: 2.2 mL/min; oven temperature 50° C.

LC/MS E: column: XBridge C18, 3.0×30 mm, 2.5 μm; mobile phase: A water (10 mM ammonium hydrogen carbonate), B CH3CN; gradient: 5%-95% B in 1.5 min, then 0.6 min hold; flow rate: 1.5 mL/min; oven temperature 50° C.

LC/MS F: column: Agilent poroshell 120 EC-C18, 4.6×50 mm, 2.7 μm: A water (0.1% formic acid), B CH3CN (0.1% formic acid); gradient 5%-95% B in 4.0 min, then 6.0 min hold; flow rate 0.95 mL/min; oven temp 50° C.

Prep-HPLC Methods

Crude samples were dissolved in MeOH and purified by prep HPLC using a Gilson 215 instrument, detection wavelength 214 nm:

Prep HPLC A: column: XBridge C18, 21.2*250 mm, 10 μm; mobile phase: A water (10 mM ammonium hydrogen carbonate), B CH3CN; gradient elution as in text; flow rate: 20 mL/min.

Prep HPLC B: column: XBridge C18, 21.2*250 mm, 10 μm; mobile phase: A water (10 mM formic acid), B CH3CN; gradient elution as in text; flow rate: 20 mL/min.

Prep HPLC C: column: XBridge OBD C18, 19*100 mm, 5 μm; mobile phase: A water, B CH3CN; gradient elution as in text; flow rate: 20 mL/min.

Prep Chiral SFC Methods

Racemic products were separated to individual enantiomers by chiral Prep SFC using an SFC-80 (Thar, Waters) instrument, detection wavelength 214 nm:

Prep chiral SFC A: column: (R,R)-Whelk-O1, 20*250 mm, 5 μm (Decial), column temperature: 35° C., mobile phase: CO2/methanol (0.2% methanol ammonia)=60/40, flow rate: 80 g/min, back pressure: 100 bar.

Prep chiral SFC B: column: AD 20*250 mm, 10 μm (Daicel), column temperature: 35° C., mobile phase: CO2/methanol (0.2% methanol ammonia)=60/40, flow rate: 80 g/min, back pressure: 100 bar.

Prep chiral SFC C: column: AS 20*250 mm, 10 μm (Daicel), column temperature: 35° C., mobile phase: CO2/methanol (0.2% methanol ammonia)=60/40, flow rate: 80 g/min, back pressure: 100 bar.

Analytical Chiral SFC Methods

Chiral products were analyzed by chiral SFC using an SFC-80 (Thar, Waters) instrument, detection wavelength 214 nm:

Chiral SFC A: column: (R,R)-Whelk-O1, 4.6*100 mm, 5 μm (Decial), column temperature: 40° C., mobile phase: CO2/methanol (0.2% methanol ammonia), isocratic elution as in text, flow rate: 4 g/min, back pressure: 120 bar.

Chiral SFC B: column: AD 4.6*100 mm, 5 μm (Daicel), column temperature: 40° C., mobile phase: CO2/methanol (0.2% methanol ammonia), isocratic elution as in text, flow rate: 4 g/min, back pressure: 120 bar.

Chiral SFC C: column: AS 4.6*100 mm, 5 μm (Daicel), column temperature: 40° C., mobile phase: CO2/methanol (0.2% methanol ammonia), isocratic elution as in text, flow rate: 4 g/min, back pressure: 120 bar.

Chiral SFC D: column: OD 4.6*100 mm, 5 μm (Daicel), column temperature: 40° C., mobile phase: CO2/methanol (0.2% methanol ammonia), isocratic elution as in text, flow rate: 4 g/min, back pressure: 120 bar.

Chiral SFC E: column: Cellulose-SC 4.6*100 mm, 5 μm (Daicel), column temperature: 40° C., mobile phase: CO2/methanol (0.2% methanol ammonia), isocratic elution as in text, flow rate: 4 g/min, back pressure: 120 bar.

Chiral SFC F: column: OZ 4.6*100 mm, 5 μm (Daicel), column temperature: 40° C., mobile phase: CO2/methanol (0.2% methanol ammonia), isocratic elution as in text, flow rate: 4 g/min, back pressure: 120 bar.

Chiral SFC G: column: IC 4.6*100 mm, 5 μm (Daicel), column temperature: 40° C., mobile phase: CO2/methanol (0.2% methanol ammonia), isocratic elution as in text, flow rate: 4 g/min, back pressure: 120 bar.

Chiral H: column: AD 4.6*250 mm, 5 μm (SHIMADZU), column temperature: 40° C., mobile phase: n-Hexane (0.1% DEA):EtOH (0.1% DEA), isocratic elution as in text, flow rate: 1 mL/min.

Example 1: Preparation of 2-hydroxy-2-(4-hydroxy-1-(3-(5,6,7,8-tetrahydro-1,8-naphthyridin-2-yl)propylcarbamoyl)piperidin-4-yl)acetic Acid (Compound 1)

Step 1: tert-butyl 4-(1-(benzyloxy)-2-ethoxy-2-oxo-ethyl)-4-hydroxypiperidine-1-carboxylate

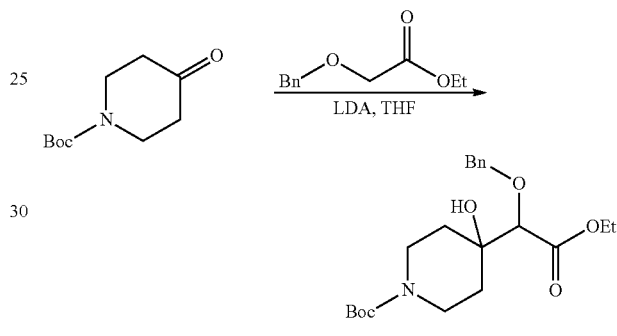

To a solution of ethyl 2-(benzyloxy)acetate (1.30 g, 6.69 mmol) in anhydrous THF (30 mL) at −78° C. was added dropwise LDA (2.0 M, 4.40 mL). The mixture was stirred for 30 min, and then tert-butyl 4-oxopiperidine-1-carboxylate (1.15 g, 5.77 mmol) in anhydrous THF (20 mL) was added. The mixture was stirred at −78° C. for 1 hour, then quenched with sat aqueous NH4Cl (30 mL) and extracted with EtOAc (50 mL×3). The combined organic extracts were washed with brine and dried over Na2SO4, filtered and concentrated in vacuo. The residue was purified by silica gel column (25% EtOAc in pet ether) to give the desired product as a colorless oil (1.82 g). Yield 80% (95% purity, UV=214 nm, ESI 294.1 (M+H)+).

Step 2: ethyl 2-(benzyloxy)-2-(4-hydroxypiperidin-4-yl)acetate

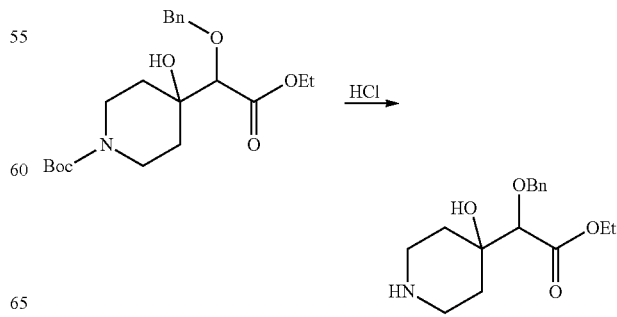

A mixture of tert-butyl 4-(1-(benzyloxy)-2-ethoxy-2-oxo-ethyl)-4-hydroxypiperidine-1-carboxylate (1.82 g, 4.62 mmol) in HCl/dioxane (4.0 M, 10 mL) was stirred at room temperature for 2 hours. Solvent was removed in vacuo to give the desired product as a pale yellow solid (1.5 g). Yield 98% (90% purity, UV=214 nm, ESI 294.3 (M+H)+).

Step 3: ethyl 2-(benzyloxy)-2-(4-hydroxy-1-(3-(5,6,7,8-tetrahydro-1,8-naphthyridin-2-yl)propylcarbamoyl)piperidin-4-yl)acetate

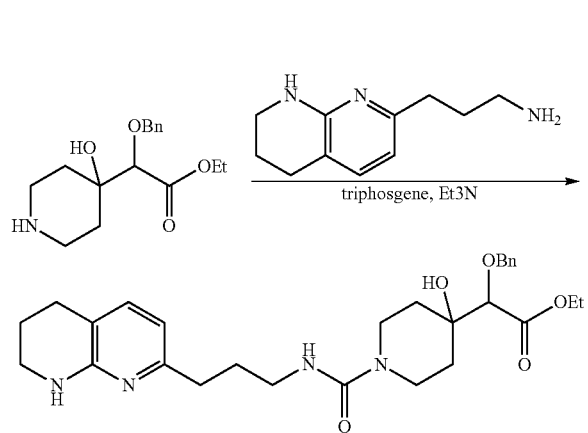

To a mixture of 3-(5,6,7,8-tetrahydro-1,8-naphthyridin-2-yl)propan-1-amine (455 mg, 2.00 mmol) and triethylamine (1.00 mL) in DCM (20 mL) at 0° C. was added triphosgene (297 mg, 1.00 mmol). The mixture was stirred for 30 min, and then ethyl 2-(benzyloxy)-2-(4-hydroxypiperidin-4-yl)acetate (990 mg, 3.00 mmol) in DCM (20 mL) was added. The mixture was stirred at room temperature for 16 hours. Solvent was removed in vacuo, and the residue was purified by silica gel column (5% MeOH in DCM) to give the desired product as a pale yellow solid (300 mg). Yield 29% (91% purity, UV=214 nm, ESI 511.4 (M+H)+).

Step 4: ethyl 2-hydroxy-2-(4-hydroxy-1-(3-(5,6,7,8-tetrahydro-1,8-naphthyridin-2-yl)propylcarbamoyl)piperidin-4-yl)acetate

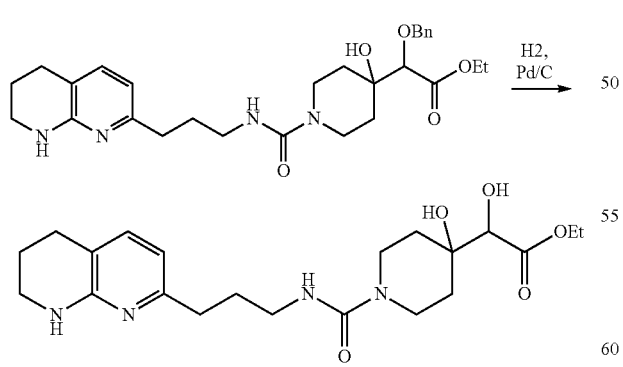

A mixture of ethyl 2-(benzyloxy)-2-(4-hydroxy-1-(3-(5,6,7,8-tetrahydro-1,8-naphthyridin-2-yl)propylcarbamoyl)piperidin-4-yl)acetate (300 mg, 0.59 mmol) and Pd/C (10%, 100 mg) in EtOAc (30 mL) was stirred under balloon hydrogen at room temperature for 16 hours. The mixture was filtered and concentrated to give the desired product as a gray solid (240 mg). Yield 97% (92% purity, UV=214 nm, ESI 421.4 (M+H)+).

Step 5: 2-hydroxy-2-(4-hydroxy-1-(3-(5,6,7,8-tetrahydro-1,8-naphthyridin-2-yl)propylcarbamoyl)piperidin-4-yl)acetic Acid (Compound 1)

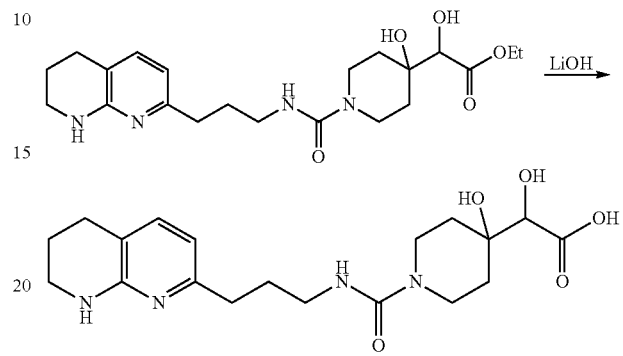

Ethyl 2-hydroxy-2-(4-hydroxy-1-(3-(5,6,7,8-tetrahydro-1,8-naphthyridin-2-yl) propylcarbamoyl)piperidin-4-yl)acetate (240 mg, 0.57 mmol) was treated with LiOH—H$_2$O (239 mg, 5.70 mmol) in MeOH (5.0 mL) and H2O (2.5 mL) at room temperature for 2 hours. The product was purified by Prep-HPLC A (33-65% MeCN) to give compound 1 as a white solid (180 mg, 80% yield). LC/MS B: 100% purity, UV=214 nm, Rt=1.06 min, ESI 393.4 (M+H)+. 1H NMR (400 MHz, CD3OD) δ 7.47 (d, J=7.2 Hz, 1H), 6.55 (d, J=7.2 Hz, 1H), 3.88-3.76 (m, 2H), 3.68 (s, 1H), 3.48-3.45 (m, 2H), 3.30-3.06 (m, 4H), 2.80-2.77 (m, 2H), 2.71-2.65 (m, 2H), 2.14-2.12 (m, 1H), 1.96-1.90 (m, 2H), 1.87-1.81 (m, 2H), 1.79-1.74 (m, 1H), 1.55-1.52 (m, 1H), 1.396-1.35 (m, 1H).

Example 2: Preparation of 2-(4-hydroxy-1-(5-(5,6,7,8-tetrahydro-1,8-naphthyridin-2-yl)pentyl)piperidin-4-yl)-2-phenylacetic Acid (Compounds 2-P1 and 2-P2)

Step 1: 2-(1-(tert-butoxycarbonyl)-4-hydroxypiperidin-4-yl)-2-phenylacetic Acid

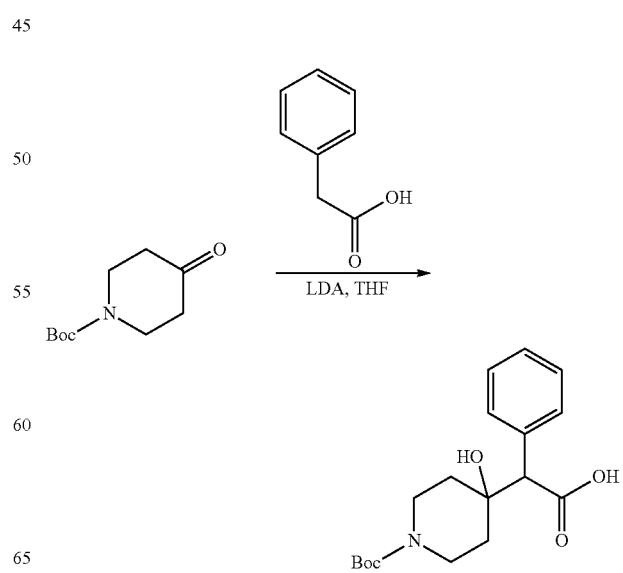

To a solution of 2-phenylacetic acid (2.04 g, 15.0 mmol) in anhydrous THF (20 mL) at −78° C. was added dropwise LDA (2.0 M, 15 mL). The mixture was stirred for 30 min, and then tert-butyl 4-oxopiperidine-1-carboxylate (3.0 g, 15.0 mmol) in anhydrous THF (20 mL) was added. This mixture was stirred at −78° C. for 1 h, then quenched with sat aqueous NH$_4$Cl (30 mL) and extracted with EtOAc (50 mL×3). The combined organic extracts were washed with brine and dried over Na$_2$SO$_4$, filtered and concentrated in vacuo. The residue was purified by silica gel column (DCM: MeOH 10:1) to give the desired product as a white solid (1.0 g). Yield 20% (ESI 236.2 (M+H−100)+).

Step 2: 2-(4-hydroxypiperidin-4-yl)-2-phenylacetic Acid Hydrochloride

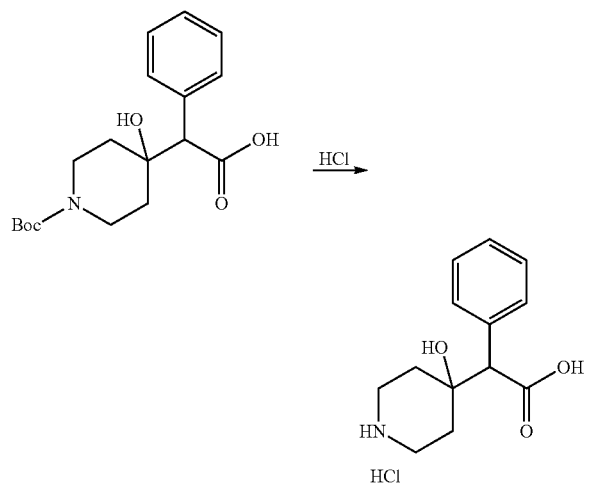

2-(1-(tert-butoxycarbonyl)-4-hydroxypiperidin-4-yl)-2-phenylacetic acid (1.0 g, 3.0 mmol) was treated with a solution of HCl/dioxane (2.0 M, 20 mL) at room temperature for 2 hours. The mixture was concentrated in vacuo to give the desired product as a white solid (800 mg). Yield 98% (ESI 236.3 (M+H)+).

Step 3: 2-(4-hydroxy-1-(5-(5,6,7,8-tetrahydro-1,8-naphthyridin-2-yl)pentyl) piperidin-4-yl)-2-phenylacetic Acid (Compounds 2-P1 and 2-P2)

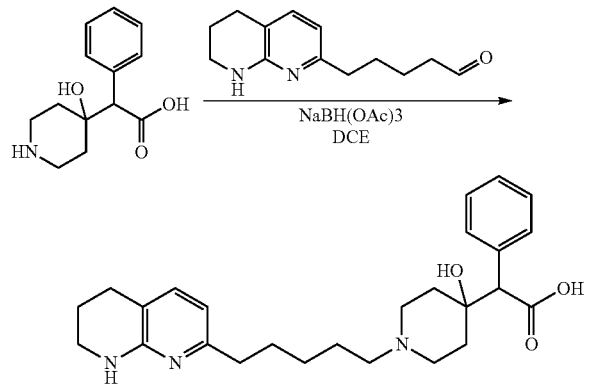

A mixture of 2-(4-hydroxypiperidin-4-yl)-2-phenylacetic acid hydrochloride (216 mg, 0.80 mmol), NaBH(OAc)$_3$ (583 mg, 2.75 mmol) and 5-(5,6,7,8-tetrahydro-1,8-naphthyridin-2-yl)pentanal (200 mg, 0.92 mmol) in DCM (10 mL) was stirred at room temperature for 1 hour. Solvent was removed in vacuo, and the residue was purified by Prep-HPLC A (35-65% MeCN) to give the racemic product (compound 2) as a white solid (65 mg, 19% yield). The racemic product was separated by prep chiral SFC A to give enantiomeric products compound 2-P1 (27 mg) and compound 2-P2 (23 mg) as white solids.

Compound 2-P1 LC/MS A: 92% purity, UV=214 nm, Rt=1.55 min, ESI 438.4 (M+H)+. 1H NMR (400 MHz, CD3OD) δ 7.35-7.33 (m, 2H), 7.19-7.12 (m, 3H), 7.03 (d, J=7.6 Hz, 1H), 6.25 (d, J=7.2 Hz, 1H), 3.26-3.20 (m, 3H), 3.18-3.04 (m, 2H), 2.90-2.82 (m, 2H), 2.59-2.56 (m, 2H), 2.44-2.40 (m, 2H), 1.94-1.72 (m, 4H), 1.62-1.44 (m, 6H), 1.30-1.15 (m, 4H). Chiral SFC A (40% MeOH): ee 100%, Rt=2.86 min.

Compound 2-P2 LC/MS A: 92% purity, UV=214 nm, Rt=1.55 min, ESI 438.4 (M+H)+. 1H NMR (400 MHz, CD3OD) δ 7.35-7.33 (m, 2H), 7.19-7.12 (m, 3H), 7.03 (d, J=7.6 Hz, 1H), 6.25 (d, J=7.2 Hz, 1H), 3.26-3.20 (m, 3H), 3.18-3.04 (m, 2H), 2.90-2.82 (m, 2H), 2.59-2.56 (m, 2H), 2.44-2.40 (m, 2H), 1.94-1.72 (m, 4H), 1.62-1.44 (m, 6H), 1.30-1.15 (m, 4H). Chiral SFC A (40% MeOH): ee 100%, Rt=3.86 min.

Example 3: Preparation of 2-(4-hydroxy-1-(5-(5,6,7,8-tetrahydro-1,8-naphthyridin-2-yl)pentyl)piperidin-4-yl)propanoic Acid (Compound 3)

Step 1: tert-butyl 4-(1-(benzyloxy)-1-oxopropan-2-yl)-4-hydroxypiperidine-1-carboxylate

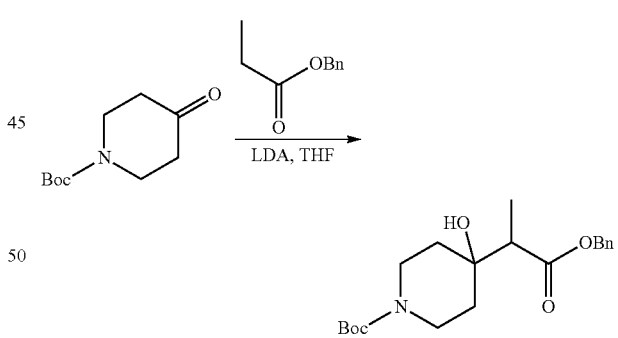

To a solution of benzyl propionate (2.46 g, 15.0 mmol) in anhydrous THF (30 mL) at −78° C. was added dropwise LDA (2.0 M, 7.5 mL). The mixture was stirred for 30 min, and then tert-butyl 4-oxopiperidine-1-carboxylate (3.0 g, 15.0 mmol) in anhydrous THF (20 mL) was added. This mixture was stirred at −78° C. for 1 h, then quenched with sat aqueous NH$_4$Cl (30 mL) and extracted with EtOAc (50 mL×3). The combined organic extracts were washed with brine and dried over Na$_2$SO$_4$, filtered and concentrated in vacuo. The residue was purified by silica gel column (pet ether:EtOAc 3:1) to give the desired product as a white solid (2.5 g). Yield 46% (ESI 264.2 (M+H−100)+).

Step 2: benzyl 2-(4-hydroxypiperidin-4-yl)propanoate Hydrochloride

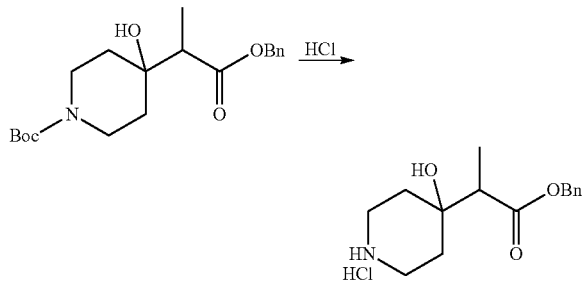

Tert-butyl 4-(1-(benzyloxy)-1-oxopropan-2-yl)-4-hydroxypiperidine-1-carboxylate (400 mg, 1.10 mmol) was treated with a solution of HCl/dioxane (2.0 M, 10 mL) at room temperature for 2 hours, then concentrated in vacuo to give the desired product as a white solid (322 mg). Yield 98% (ESI 264 (M+H)+).

Step 3: benzyl 2-(4-hydroxy-1-(5-(5,6,7,8-tetrahydro-1,8-naphthyridin-2-yl)pentyl)piperidin-4-yl)propanoate

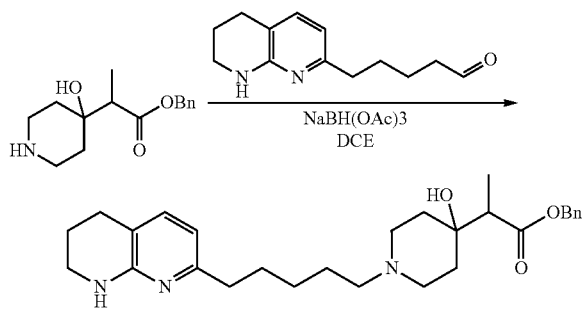

A mixture of benzyl 2-(4-hydroxypiperidin-4-yl)propanoate hydrochloride (241 mg, 0.92 mmol), NaBH(OAc)₃ (583 mg, 2.75 mmol) and 5-(5,6,7,8-tetrahydro-1,8-naphthyridin-2-yl)pentanal (200 mg, 0.92 mmol) in DCM (10 mL) was stirred at room temperature for 1 hour. Solvent was removed in vacuo, and the residue was purified by silica gel column (DCM:MeOH 10:1) to give the desired product as a white solid (150 mg). Yield 35% (ESI 466.5 (M+H)+).

Step 4: 2-(4-hydroxy-1-(5-(5,6,7,8-tetrahydro-1,8-naphthyridin-2-yl)pentyl) piperidin-4-yl)propanoic Acid (Compound 3)

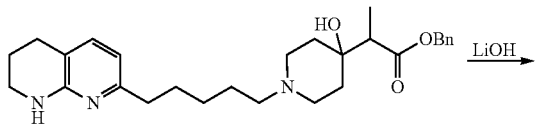

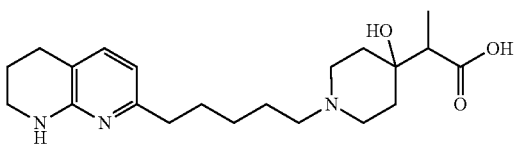

Benzyl 2-(4-hydroxy-1-(5-(5,6,7,8-tetrahydro-1,8-naphthyridin-2-yl)pentyl)piperidin-4-yl)propanoate (150 mg, 0.32 mmol) was treated with LiOH—H₂O (100 mg, 2.38 mmol) in MeOH (3 mL) and H₂O (1 mL) at room temperature for 2 hours. Solvent was removed in vacuo, and the residue was purified by Prep-HPLC A (35-65% MeCN) to give compound 3 as a white solid (55 mg, 45% yield). LC/MS A: 100% purity, UV=214 nm, Rt=1.45 min, ESI 376.4 (M+H)+. 1H NMR (400 MHz, CD3OD) δ 7.14 (d, J=7.2 Hz, 1H), 6.37 (d, J=7.2 Hz, 1H), 3.39-3.26 (m, 4H), 3.10-3.01 (m, 2H), 2.94-2.90 (m, 2H), 2.69 (t, J=6.4 Hz, 2H), 2.54 (t, J=7.6 Hz, 2H), 2.27 (q, J=7.2 Hz, 1H), 1.99-1.64 (m, 10H), 1.41-1.33 (m, 2H), 1.17 (d, J=7.2 Hz, 3H).

Example 4: Preparation of 2-acetamido-2-(1-hydroxy-4-(3-(5,6,7,8-tetrahydro-1,8-naphthyridin-2-yl)propylcarbamoyl)cyclohexyl)acetic Acid (Compounds 4-P1 and 4-P2)

Step 1: benzyl 4-(1-(dibenzylamino)-2-ethoxy-2-oxoethyl)-4-hydroxycyclohexanecarboxylate

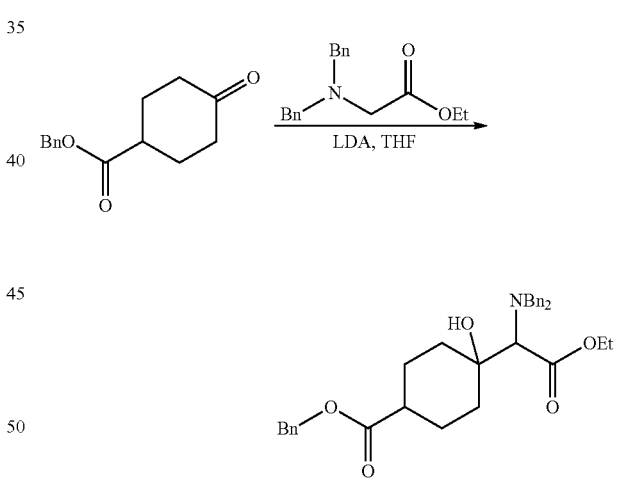

To a solution of ethyl 2-(dibenzylamino)acetate (2.43 g, 8.59 mmol) in anhydrous THF (50 mL) at −78° C. was added LDA (2.0 M, 6.60 mL). The mixture was stirred for 30 min, and benzyl 4-oxocyclohexanecarboxylate (1.50 g, 6.61 mmol) in anhydrous THF (20 mL) was added. The resulting mixture was stirred at −78° C. for 1 h, then quenched with sat aqueous NH4Cl (30 mL) and extracted with EtOAc (50 mL×3). The combined organic layers were washed with brine and dried over Na2SO4, filtered and concentrated in vacuo. The residue was purified by silica gel column (15% EtOAc in pet ether) to give the desired product as a colorless oil (2.30 g). Yield 52% (92% purity, UV=214 nm, ESI 516.3 (M+H)+).

Step 2: 4-(1-amino-2-ethoxy-2-oxoethyl)-4-hydroxycyclohexanecarboxylic Acid

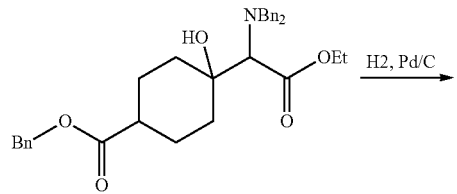

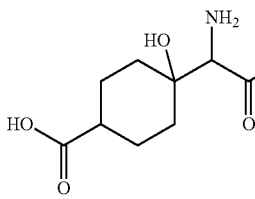

A mixture of benzyl 4-(1-(dibenzylamino)-2-ethoxy-2-oxoethyl)-4-hydroxycyclohexanecarboxylate (2.30 g, 4.45 mmol) and Pd/C (10%, 1.00 g) in EtOAc (30 mL) was stirred at 50° C. under balloon hydrogen for 16 hours. The mixture was filtered and concentrated in vacuo to give the desired product as a gray solid (1.00 g). Yield 92% (90% purity, UV=214 nm, ESI 246.3 (M+H)+).

Step 3: 4-(1-acetamido-2-ethoxy-2-oxoethyl)-4-hydroxycyclohexanecarboxylic Acid

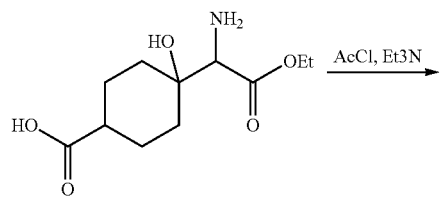

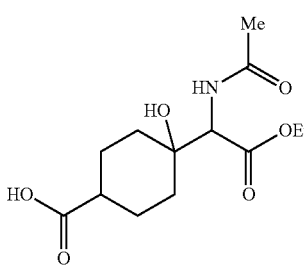

To a solution of 4-(1-amino-2-ethoxy-2-oxoethyl)-4-hydroxycyclohexanecarboxylic acid (500 mg, 2.04 mmol) and triethylamine (2.0 mL) in DCM (20 mL) at 0° C. was added dropwise acetyl chloride (0.17 mL, 2.45 mmol). The mixture was stirred at room temperature for 2 hours, then concentrated in vacuo. The residue was dissolved in EtOAc, filtered to remove the solid and concentrated in vacuo to give the desired product as a gray solid (585 mg). Yield 98% (90% purity, UV=214 nm, ESI 288.3 (M+H)+).

Step 4: ethyl 2-acetamido-2-(1-hydroxy-4-((3-(5,6,7,8-tetrahydro-1,8-naphthyridin-2-yl)propyl)carbamoyl)cyclohexyl)acetate

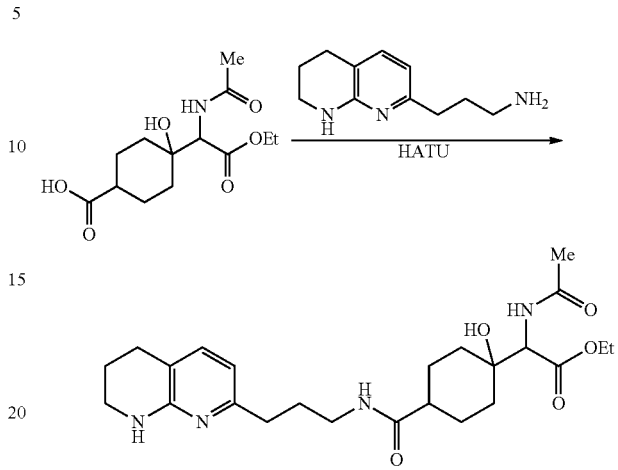

A mixture of 3-(5,6,7,8-tetrahydro-1,8-naphthyridin-2-yl)propan-1-amine (300 mg, 1.57 mmol), DIEA (461 mg, 3.58 mmol), HATU (544 mg, 1.43 mmol) and 4-(1-acetamido-2-ethoxy-2-oxoethyl)-4-hydroxycyclohexanecarboxylic acid (585 mg, 2.04 mmol) in DMF (10 mL) was stirred at room temperature for 16 hours. The mixture was concentrated in vacuo, and the residue was purified by silica gel column (10% MeOH in DCM) to give the desired product as a colorless oil (150 mg). Yield 21% (88% purity, UV=214 nm, ESI 461.3 (M+H)+).

Step 5: 2-acetamido-2-(1-hydroxy-4-(3-(5,6,7,8-tetrahydro-1,8-naphthyridin-2-yl)propylcarbamoyl)cyclohexyl)acetic Acid (Compounds 4-P1 and 4-P2)

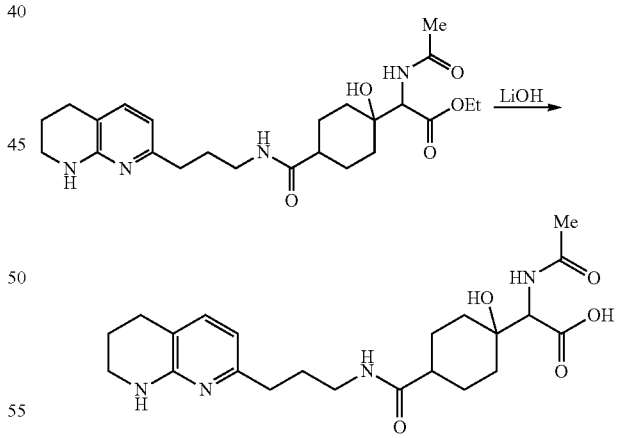

Ethyl 2-acetamido-2-(1-hydroxy-4-((3-(5,6,7,8-tetrahydro-1,8-naphthyridin-2-yl)propyl)carbamoyl)cyclohexyl)acetate (150 mg, 0.33 mmol) was treated with LiOH—H$_2$O (137 mg, 3.25 mmol) in MeOH (5 mL) and H$_2$O (2.5 mL) at room temperature for 2 hours. The crude was purified by Prep-HPLC A (33-65% MeCN) to give the racemic compound 4 as a white solid (30 mg, 21% yield). The racemic product was separated by prep chiral SFC C to give enantiomeric products compound 4-P1 (6.9 mg) and compound 4-P2 (13 mg) as white solids.

Compound 4-P1 LC/MS A: 92% purity, UV=214 nm, Rt=1.34 min, ESI 433.4 (M+H)+. 1H NMR (400 MHz, CD3OD) δ 7.39 (d, J=7.6 Hz, 1H), 6.44 (d, J=7.6 Hz, 1H), 4.04 (s, 1H), 3.33-3.30 (m, 2H), 3.12-3.09 (m, 2H), 2.65-2.62 (m, 2H), 2.58-2.54 (m, 2H), 1.99-1.96 (m, 1H), 1.94 (s, 3H), 1.80-1.73 (m, 4H), 1.63-1.57 (m, 2H), 1.54-1.49 (m, 4H), 1.42-1.33 (m, 1H).

Compound 4-P2 LC/MS A: 92% purity, UV=214 nm, Rt=1.33 min, ESI 433.4 (M+H)+. 1H NMR (400 MHz, CD3OD) δ 7.39 (d, J=7.6 Hz, 1H), 6.44 (d, J=7.6 Hz, 1H), 4.04 (s, 1H), 3.33-3.30 (m, 2H), 3.12-3.09 (m, 2H), 2.65-2.62 (m, 2H), 2.58-2.54 (m, 2H), 1.99-1.96 (m, 1H), 1.94 (s, 3H), 1.80-1.73 (m, 4H), 1.63-1.57 (m, 2H), 1.54-1.49 (m, 4H), 1.42-1.33 (m, 1H). Chiral SFC C (40% MeOH): ee 98%, Rt=3.08 min.

Example 5: Preparation of 2-(4-hydroxy-1-(5-(5,6,7,8-tetrahydro-1,8-naphthyridin-2-yl)pentanoyl)piperidin-4-yl)acetic Acid (Compound 5)

Step 1: methyl 6-oxoheptanoate

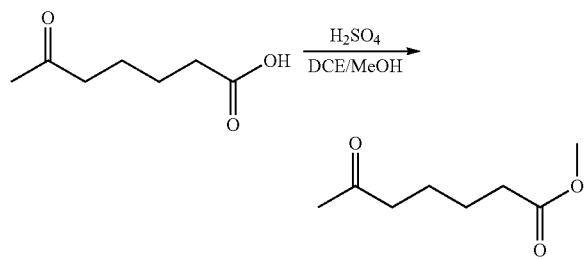

Concentrated $H_2SO_4$ (0.2 mL) was added to a stirred solution of 6-oxoheptanoic acid (10 g, 69 mmol) in DCE/MeOH (50 mL/20 mL). The mixture was stirred at 90° C. overnight. The solution was cooled to room temperature and concentrated. The residue was diluted with DCM (200 mL), washed with saturated $NaHCO_3$ solution, water, brine, dried and concentrated to give methyl 6-oxoheptanoate as light yellow liquid (8.4 g) Yield 76% (100% purity, UV=214 nm, ESI 159 (M+H)+).

Step 2: methyl 5-(1,8-naphthyridin-2-yl)pentanoate

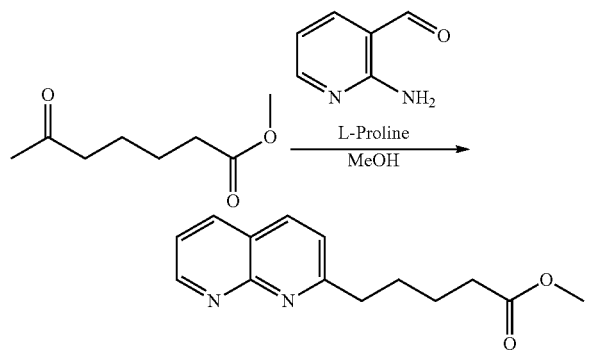

A mixture of methyl 6-oxoheptanoate (11 g, 69.53 mmol), 2-aminonicotinaldehyde (8.5 g, 69.53 mmol) and L-proline (4 g, 34.77 mmol) in MeOH (100 mL) was stirred at 90° C. overnight. The mixture was cooled to room temperature and concentrated. The crude product was purified by silica gel column (EtOAc) to give methyl 5-(1,8-naphthyridin-2-yl)pentanoate as light yellow solid (7 g). Yield 65% (100% purity, UV=214 nm, ESI 245 (M+H)+). $^1$H NMR (400 MHz, CDCl$_3$) δ 9.08 (dd, J=4.2, 1.9 Hz, 1H), 8.16 (dd, J=8.1, 1.9 Hz, 1H), 8.10 (d, J=8.3 Hz, 1H), 7.44 (dd, J=8.1, 4.3 Hz, 1H), 7.39 (d, J=8.3 Hz, 1H), 3.66 (s, 3H), 3.11-3.02 (m, 2H), 2.39 (m, 2H), 1.96 (m, 2H), 1.81-1.70 (m, 2H).

Step 3: methyl 5-(5,6,7,8-tetrahydro-1,8-naphthyridin-2-yl)pentanoate

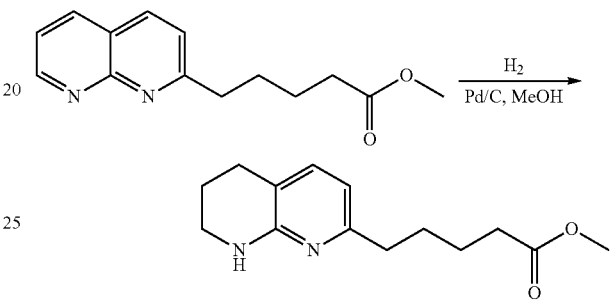

A mixture of methyl 5-(1,8-naphthyridin-2-yl)pentanoate (5 g, 20.47 mmol), and Pd/C (500 mg) in MeOH (50 mL) was stirred at room temperature under balloon $H_2$ overnight. The mixture was filtered and concentrated to give methyl 5-(5,6,7,8-tetrahydro-1,8-naphthyridin-2-yl)pentanoate as a light brown oil (4.2 g). Yield 83% (100% purity, UV=214 nm, ESI 249 (M+H)+).

Step 4: 5-(5,6,7,8-tetrahydro-1,8-naphthyridin-2-yl) pentanoic Acid

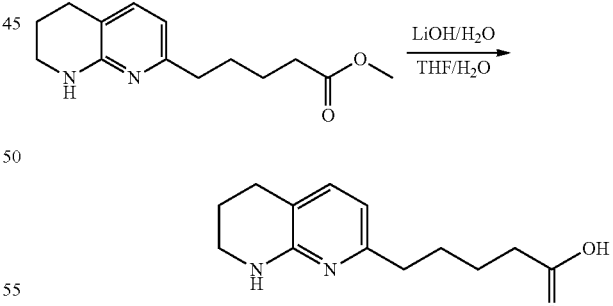

Methyl 5-(5,6,7,8-tetrahydro-1,8-naphthyridin-2-yl)pentanoate (2.6 g, 10.47 mmol) was treated with LiOH—$H_2O$ (659 mg, 15.71 mmol) in THF (4 mL) and $H_2O$ (2 mL) for 2 hours at room temperature. Solvent was removed in vacuo, then the residue was acidified with 1 N HCl to pH=6, resulting in precipitation of the product. The product was collected by filtration 5-(5,6,7,8-tetrahydro-1,8-naphthyridin-2-yl)pentanoic acid as light yellow solid (1.75 g). Yield 71% (100% purity, UV=214 nm, ESI 235 (M+H)+).

Step 5: ethyl 2-(4-hydroxy-1-(5-(5,6,7,8-tetrahydro-1,8-naphthyridin-2-yl)pentanoyl)piperidin-4-yl)acetate

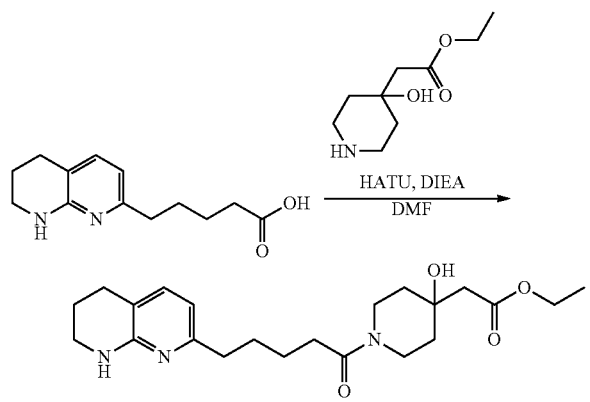

A mixture of 15-(5,6,7,8-tetrahydro-1,8-naphthyridin-2-yl)pentanoic acid dihydrochloride (100 mg, 0.32 mmol), HATU (146 mg, 0.38 mmol), ethyl 2-(4-hydroxypiperidin-4-yl)acetate (73 mg, 0.38 mmol), and DIEA (126 mg, 0.96 mmol) in DMF (2 mL) was stirred overnight. Solvent was removed in vacuo, and the residue was purified by silica gel column (pet ether:EtOAc 0:100) to give 2-(4-hydroxy-1-(5-(5,6,7,8-tetrahydro-1,8-naphthyridin-2-yl)pentanoyl)piperidin-4-yl)acetate as a light yellow solid (104 mg). Yield 79% (100% purity, UV=214 nm, ESI 404 (M+H)+).

Step 6: 2-(4-hydroxy-1-(5-(5,6,7,8-tetrahydro-1,8-naphthyridin-2-yl)pentanoyl)piperidin-4-yl)acetic Acid (Compound 5)

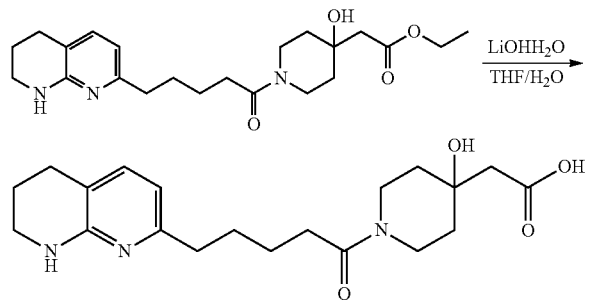

Ethyl 2-(4-hydroxy-1-(5-(5,6,7,8-tetrahydro-1,8-naphthyridin-2-yl)pentanoyl)piperidin-4-yl)acetate (200 mg, 0.50 mmol) was treated with LiOH—H$_2$O (31 mg, 0.75 mmol) in THF (4 mL) and H$_2$O (2 mL) for 2 h at room temperature. Solvent was removed in vacuo, and the residue was purified by Prep-HPLC B (30-65% MeCN) to give compound 5 as a white solid (88 mg, 61% yield) (LC/MS B: 100% purity, UV=214 nm, Rt=0.67 min, ESI 376 (M+H)+). 1H NMR (500 MHz, MeOD) δ 8.32 (s, 1H), 7.39 (d, J=7.2 Hz, 1H), 6.43 (d, J=7.2 Hz, 1H), 4.14 (d, J=12.5 Hz, 1H), 3.64 (d, J=13.4 Hz, 1H), 3.36 (s, 1H), 3.20 (s, 1H), 2.94 (t, J=12.2 Hz, 1H), 2.68 (m, 3H), 2.58 (s, 2H), 2.46 (m, 1H), 2.30 (d, J=6.0 Hz, 3H), 1.83 (m, 3H), 1.65-1.43 (m, 8H).

Example 6: Preparation of 2-(4-hydroxy-1-(5-(5,6,7,8-tetrahydro-1,8-naphthyridin-2-yl)pentyl)piperidin-4-yl)acetic Acid (Compound 6)

Step 1: tert-butyl 7-(5-methoxy-5-oxopentyl)-3,4-dihydro-1,8-naphthyridine-1(2H)-carboxylate

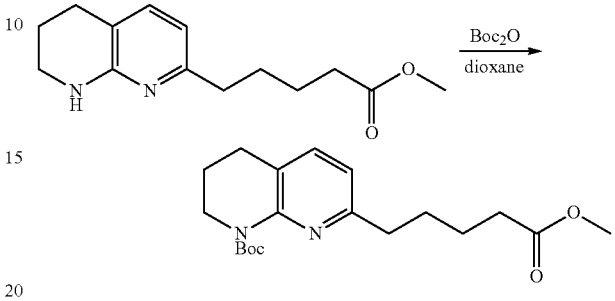

A mixture of methyl 5-(5,6,7,8-tetrahydro-1,8-naphthyridin-2-yl)pentanoate (2.4 g, 9.7 mmol) and Boc$_2$O (11 g, 48 mmol) in dioxane (20 mL) was stirred at 80° C. for 16 hrs. The mixture was concentrated, and the residue was purified by silica gel column chromatography (pet ether:EtOAc 1:1) to give tert-butyl 7-(5-methoxy-5-oxopentyl)-3,4-dihydro-1,8-naphthyridine-1(2H)-carboxylate as light yellow oil (1.8 g), Yield 53% (100% purity, UV=214 nm, ESI 349 (M+H)+).

Step 2: tert-butyl 7-(5-hydroxypentyl)-3,4-dihydro-1,8-naphthyridine-1(2H)-carboxylate

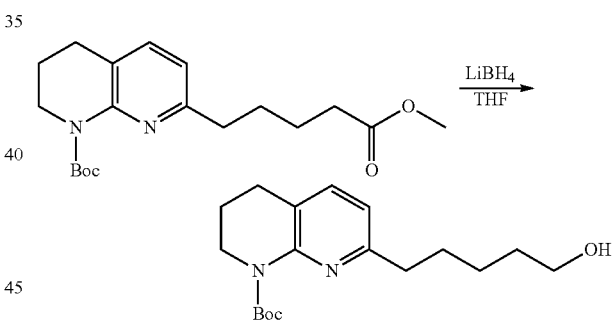

A mixture of tert-butyl 7-(5-methoxy-5-oxopentyl)-3,4-dihydro-1,8-naphthyridine-1(2H)-carboxylate (740 mg, 2.12 mmol) and LiBH$_4$ (93 mg, 4.24 mmol) in THF (10 mL) was stirred at 75° C. for 2 hrs. The solution was cooled to room temperature and concentrated, diluted with EtOAc (20 mL), washed with water and brine, dried and concentrated to give tert-butyl 7-(5-hydroxypentyl)-3,4-dihydro-1,8-naphthyridine-1(2H)-carboxylate as a light yellow oil (500 mg). Yield 73% (100% purity, UV=214 nm, ESI 321 (M+H)+).

Step 3: tert-butyl 7-(5-oxopentyl)-3,4-dihydro-1,8-naphthyridine-1(2H)-carboxylate

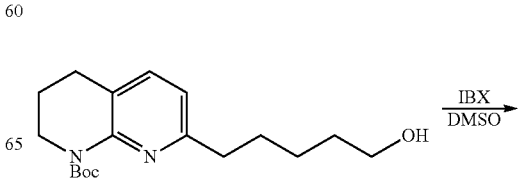

-continued

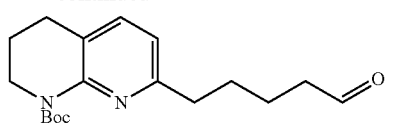

IBX (1.22 g, 4.36 mmol) was added to DMSO (15 mL) and stirred until the solution became clear. tert-butyl 7-(5-hydroxypentyl)-3,4-dihydro-1,8-naphthyridine-1(2H)-carboxylate (700 mg, 2.18 mmol) in DMSO 5 mL) was added dropwise to the solution, and the resulting mixture was stirred at room temperature for 16 hrs, then diluted with water (80 mL) and extracted with DCM (300 mL). The combined organic extracts were washed with water and brine, dried and concentrated. The residue was purified by silica gel column chromatography (pet ether:EtOAc 1:1) to give tert-butyl 7-(5-oxopentyl)-3,4-dihydro-1,8-naphthyridine-1(2H)-carboxylate as light yellow oil (498 mg) Yield 72% (100% purity, UV=214 nm, ESI 319 (M+H)+).

Step 4: tert-butyl 7-(5-(4-(2-ethoxy-2-oxoethyl)-4-hydroxypiperidin-1-yl)pentyl)-3,4-dihydro-1,8-naphthyridine-1(2H)-carboxylate

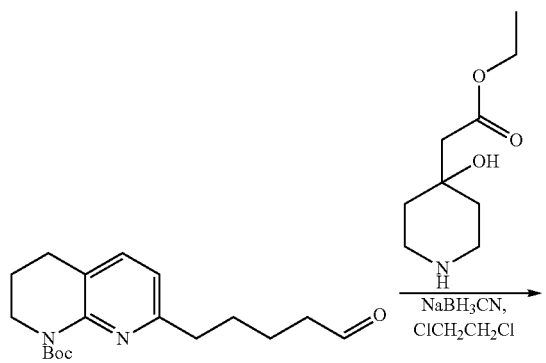

NaBH$_3$CN (63 mg, 1.00 mmol) was added to a stirred mixture of tert-butyl 7-(5-oxopentyl)-3,4-dihydro-1,8-naphthyridine-1(2H)-carboxylate (80 mg, 0.25 mmol) and ethyl 2-(4-hydroxypiperidin-4-yl)acetate (71 mg, 0.38 mmol) in DCE at room temperature. The resulting mixture was stirred for 2 h, then diluted with water (20 mL), and extracted with DCM (3×20 mL). The combined organic extracts were washed with water and brine, dried and concentrated to give tert-butyl 7-(5-(4-(2-ethoxy-2-oxoethyl)-4-hydroxypiperidin-1-yl)pentyl)-3,4-dihydro-1,8-naphthyridine-1(2H)-carboxylate as a light yellow oil (107 mg) Yield 87% (100% purity, UV=214 nm, ESI 490 (M+H)+).

Step 5: ethyl 2-(4-hydroxy-1-(5-(5,6,7,8-tetrahydro-1,8-naphthyridin-2-yl)pentyl)piperidin-4-yl)acetate

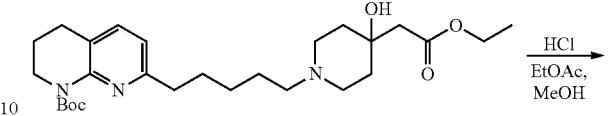

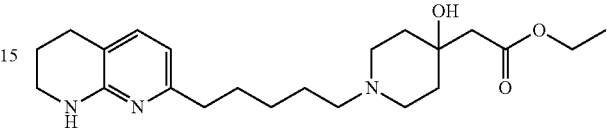

Tert-butyl 7-(5-(4-(2-ethoxy-2-oxoethyl)-4-hydroxypiperidin-1-yl)pentyl)-3,4-dihydro-1,8-naphthyridine-1(2H)-carboxylate (122 mg, 0.25 mmol) was treated with HCl (3 mL, 9 mmol) in dioxane (2 mL) at room temperature overnight. Solvent was removed in vacuo to give ethyl 2-(4-hydroxy-1-(5-(5,6,7,8-tetrahydro-1,8-naphthyridin-2-yl)pentyl)piperidin-4-yl)acetate as a light yellow solid (102 mg). Yield 100% (100% purity, UV=214 nm, ESI 390 (M+H)+).

Step 6: 2-(4-hydroxy-1-(5-(5,6,7,8-tetrahydro-1,8-naphthyridin-2-yl)pentyl)piperidin-4-yl)acetic Acid (Compound 6)

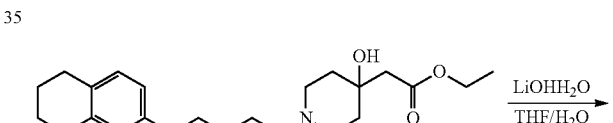

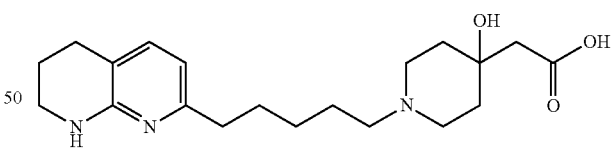

Ethyl 2-(4-hydroxy-1-(5-(5,6,7,8-tetrahydro-1,8-naphthyridin-2-yl)pentyl)piperidin-4-yl)acetate (96 mg, 0.41 mmol) was treated with LiOH—H$_2$O (26 mg, 0.62 mmol) in THF (4 mL) and H$_2$O (2 mL) for 2 h at room temperature. Solvent was removed in vacuo, and the residue was purified by Prep-HPLC A (33-65% MeCN) to give compound 6 as a white solid (50 mg, 53% yield). LC/MS A: 100% purity, UV=214 nm, Rt=1.49 min, ESI 362 (M+H)+. $^1$H NMR (400 MHz, MeOD) δ 7.17 (d, J=7.3 Hz, 1H), 6.39 (d, J=7.3 Hz, 1H), 3.42-3.35 (m, 2H), 3.27 (m, 2H), 3.12 (dd, J=13.3, 10.8 Hz, 2H), 3.00-2.90 (m, 2H), 2.70 (t, J=6.2 Hz, 2H), 2.56 (t, J=7.6 Hz, 2H), 2.36 (s, 2H), 2.01-1.79 (m, 6H), 1.71 (m, 4H), 1.40 (m, 2H).

Example 7: Preparation of 2-(cyclopentanecarboxamido)-2-(4-hydroxy-1-(3-(5,6,7,8-tetrahydro-1,8-naphthyridin-2-yl)propylcarbamoyl)piperidin-4-yl) acetic Acid (Compound 7)

Step 1: tert-butyl 4-(1-(cyclopentanecarboxamido)-2-ethoxy-2-oxoethyl)-4-hydroxypiperidine-1-carboxylate

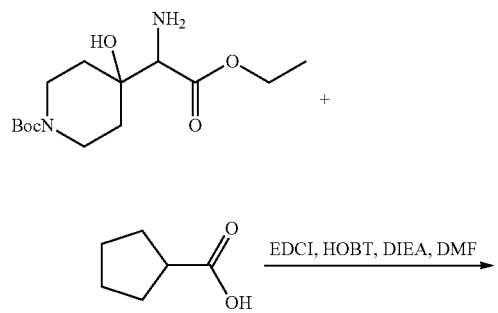

To a solution of tert-butyl 4-(1-amino-2-ethoxy-2-oxoethyl)-4-hydroxypiperidine-1-carboxylate (300 mg, 1 mmol) in DMF (5 mL) was added cyclopentanecarboxylic acid (113 mg, 1 mmol), EDCI (208 mg, 1.1 mmol), HOBT (146 mg, 1.1 mmol) and DIEA (234 mg, 1.8 mmol). The reaction mixture was stirred at room temperature for 2 h, diluted with water (25 mL) and extracted with EtOAc (15 mL×3). The combined organic phase was washed with brine, dried over Na₂SO₄ and concentrated in vacuo to give tert-butyl 4-(4-(5,6,7,8-tetrahydro-1,8-naphthyridin-2-yl)butanamido)piperidine-1-carboxylate (276 mg, 70% yield) as a yellow oil.

Step 2: ethyl 2-(cyclopentanecarboxamido)-2-(4-hydroxypiperidin-4-yl)acetate 2,2,2-trifluoroacetate

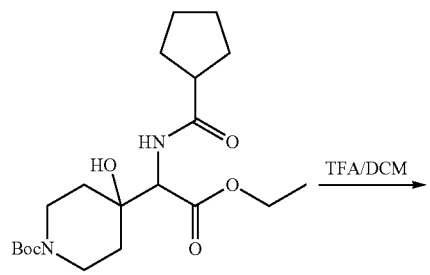

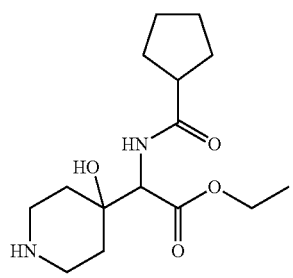

To a solution of tert-butyl 4-(4-(5,6,7,8-tetrahydro-1,8-naphthyridin-2-yl)butanamido)piperidine-1-carboxylate (276 mg, 0.69 mmol) in DCM (4 mL) was added TFA (4 mL). The reaction mixture was stirred at room temperature for 2 h, then concentrated in vacuo to give ethyl 2-(cyclopentanecarboxamido)-2-(4-hydroxypiperidin-4-yl)acetate 2,2,2-trifluoroacetate (205 mg, 98% yield) as a yellow oil. (100% purity, UV=254 nm, ESI 299.2 (M+H)+).

Step 3: ethyl 2-(cyclopentanecarboxamido)-2-(4-hydroxy-1-(3-(5,6,7,8-tetrahydro-1,8-naphthyridin-2-yl)propylcarbamoyl)piperidin-4-yl)acetate

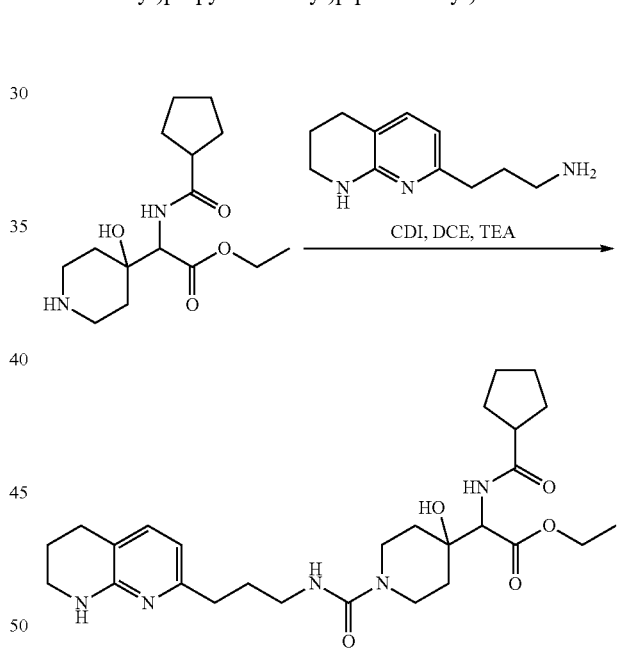

To a solution of 3-(5,6,7,8-tetrahydro-1,8-naphthyridin-2-yl)propan-1-amine (131 mg, 0.69 mmol) in DCE (5 mL) was added TEA (210 mg, 2.07 mmol) and CDI (111 mg, 0.69 mmol) at 0° C. The reaction mixture was stirred at room temperature for 1 h. Then ethyl 2-(cyclopentanecarboxamido)-2-(4-hydroxypiperidin-4-yl)acetate 2,2,2-trifluoroacetate (205 mg, 0.69 mmol) was added. The reaction mixture was stirred at room temperature for 16 h, then concentrated in vacuo. The residue was purified by silica gel column (MeOH:EtOAc=1:5) to give ethyl 2-(cyclopentanecarboxamido)-2-(4-hydroxy-1-(3-(5,6,7,8-tetrahydro-1,8-naphthyridin-2-yl)propylcarbamoyl)piperidin-4-yl)acetate (100 mg, 38% yield) as a yellow oil. (100% purity, UV=254 nm, ESI 516.3 (M+H)+).

Step 4: 2-(cyclopentanecarboxamido)-2-(4-hydroxy-1-(3-(5,6,7,8-tetrahydro-1,8-naphthyridin-2-yl)propylcarbamoyl)piperidin-4-yl)acetic Acid (Compound 7)

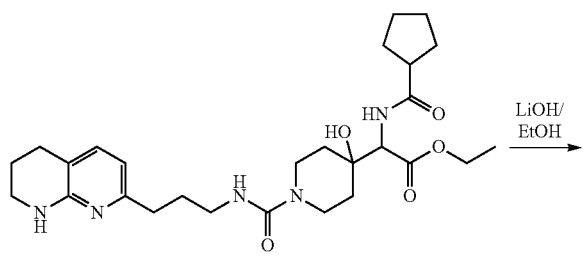

Ethyl 2-(cyclopentanecarboxamido)-2-(4-hydroxy-1-(3-(5,6,7,8-tetrahydro-1,8-naphthyridin-2-yl)propylcarbamoyl)piperidin-4-yl)acetate (100 mg, 0.19 mmol) was treated with LiOH (21 mg, 0.9 mmol) in EtOH (4 mL) and H$_2$O (2 mL) at room temperature for 2 h. The reaction mixture was neutralized with 6 N HCl. The resultant mixture was concentrated in vacuo, and the residue was purified by prep HPLC A (30-62% MeCN) to give compound 7 as a white solid (60 mg). LC/MS A: 100% purity, UV=214 nm, Rt=1.43 min, ESI 488.2 (M+H)$^+$. 1H NMR (500 MHz, MeOD) δ 7.56 (d, J=7.4 Hz, 1H), 6.62 (d, J=7.4 Hz, 1H), 4.33 (s, 1H), 3.78 (d, J=13.3 Hz, 2H), 3.53-3.45 (m, 2H), 3.31-3.09 (m, 4H), 2.84-2.65 (m, 5H), 2.01-1.49 (m, 16H).

Example 8: 2-acetamido-2-(4-hydroxy-1-(5-(5,6,7,8-tetrahydro-1,8-naphthyridin-2-yl)pentyl)piperidin-4-yl)acetic Acid (Compounds 8-P1 and 8-P2)

Step 1: tert-butyl 4-(1-(dibenzylamino)-2-ethoxy-2-oxoethyl)-4-hydroxypiperidine-1-carboxylate

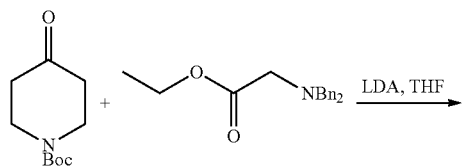

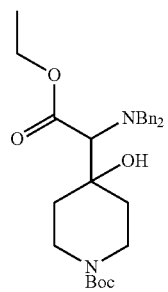

To a solution of ethyl 2-(dibenzylamino)acetate (15.6 g, 55 mmol) in THF (200 mL) at −78° C. was added LDA (2 M in THF/hexane, 68 mL, 136 mmol). The reaction mixture was stirred at −78° C. for 1 h. Then a solution of tert-butyl 4-oxopiperidine-1-carboxylate (11 g, 55 mmol) in THF (20 mL) was added, and the reaction was stirred at −78° C. for 2 h, then quenched with saturated NH$_4$Cl solution and extracted with EtOAc (3×200 mL). The combined organic extracts were washed with brine and concentrated in vacuo, and the residue was separated by silica gel column (EtOAc: pet petroleum=1:1) to give tert-butyl 4-(1-(dibenzylamino)-2-ethoxy-2-oxoethyl)-4-hydroxypiperidine-1-carboxylate as yellow oil (12 g, 45% yield). (90% purity, UV=214 nm, ESI 483.3 (M+H)+).

Step 2: tert-butyl 4-(1-amino-2-ethoxy-2-oxoethyl)-4-hydroxypiperidine-1-carboxylate A mixture of tert-butyl 4-(1-(dibenzylamino)-2-ethoxy-2-oxoethyl)-4-hydroxypiperidine-1-carboxylate (10.5 g, 21.8 mmol) and Pd/C (10%, 1 g) in EtOH (100 mL) was stirred at 55° C. under H$_2$ atmosphere (1 atm, 4 L) for 3 days. The reaction mixture was filtered and concentrated in vacuo to give tert-butyl 4-(1-amino-2-ethoxy-2-oxoethyl)-4-hydroxypiperidine-1-carboxylate as a yellow oil (5.3 g, 77% yield). (80% purity, UV=214 nm, ESI 247.0 (M-55)$^+$).

Step 3: tert-butyl 4-(1-acetamido-2-ethoxy-2-oxo-ethyl)-4-hydroxypiperidine-1-carboxylate

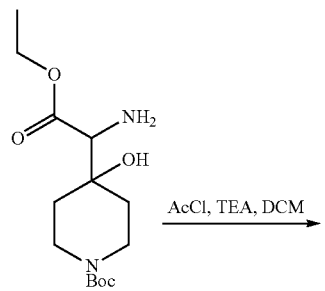

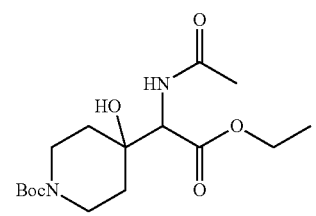

To a solution of tert-butyl 4-(1-amino-2-ethoxy-2-oxoethyl)-4-hydroxypiperidine-1-carboxylate (4.3 g, 14.2 mmol) and triethylamine (2.86 g, 28.4 mmol) in DCM (50 mL) at 0° C. was added dropwise acetyl chloride (1.7 g, 21.3 mmol). The reaction mixture was stirred at room temperature for 2 hours, then diluted with water (100 mL) and extracted with DCM (3×50 mL). The combined organic phase was washed with brine, dried over Na$_2$SO$_4$, filtered and concentrated in vacuo, and the residue was purified by Prep-HPLC A (30-70% MeCN) to give the racemic product tert-butyl 4-(1-acetamido-2-ethoxy-2-oxoethyl)-4-hydroxypiperidine-1-carboxylate as a colourless oil (2.4 g, 49% yield). The racemic product was separated by Prep chiral SFC B to give enantiomeric products tert-butyl 4-(1-acetamido-2-ethoxy-2-oxoethyl)-4-hydroxypiperidine-1-carboxylate-P1 as a colourless oil (0.9 g, 38% yield) and tert-butyl 4-(1-acetamido-2-ethoxy-2-oxoethyl)-4-hydroxypiperidine-1-carboxylate-P2 as a colourless oil (0.95 g, 40% yield).

P1: 90% purity, UV=214 nm, ESI 345.4 (M+H)$^+$. Chiral SFC B (10% MeOH): ee 96.4%, Rt=1.18 min P2: 95% purity, UV=214 nm, ESI 345.4 (M+H)$^+$. Chiral SFC B (10% MeOH): ee 100%, Rt=1.64 min Step 4: ethyl 2-acetamido-2-(4-hydroxypiperidin-4-yl)acetate-P1

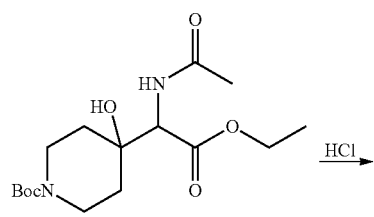

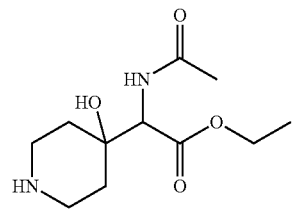

Tert-butyl 4-(1-acetamido-2-ethoxy-2-oxoethyl)-4-hydroxypiperidine-1-carboxylate-P1 (900 mg, 2.6 mmol) was treated with HCl (40 mmol) in 1,4-dioxane (20 mL) at room temperature for 2 hours. The reaction mixture concentrated in vacuo to give ethyl 2-acetamido-2-(4-hydroxypiperidin-4-yl)acetate-P1 as a yellow solid (710 mg, 97% yield) (90% purity, UV=214 nm, ESI 245.1 (M+H)$^+$).

Step 5: tert-butyl 7-(5-(4-(1-acetamido-2-ethoxy-2-oxoethyl)-4-hydroxypiperidin-1-yl)pentyl)-3,4-dihydro-1,8-naphthyridine-1(2H)-carboxylate-P1

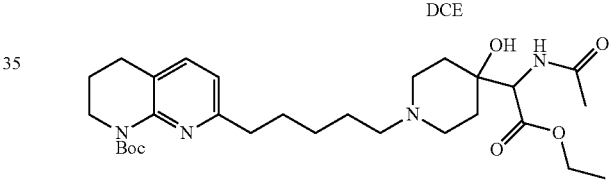

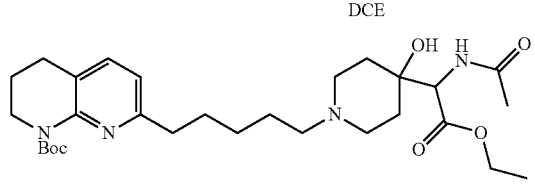

NaBH$_3$CN (39 mg, 0.60 mmol) was added to a stirred mixture of tert-butyl 7-(5-oxopentyl)-3,4-dihydro-1,8-naphthyridine-1(2H)-carboxylate (49 mg, 0.15 mmol) and ethyl 2-acetamido-2-(4-hydroxypiperidin-4-yl)acetate-P1 (65 mg, 0.23 mmol) in DCE at room temperature. The resulting mixture was stirred at room temperature for 2 hours, then diluted with water (20 mL) and extracted with DCM (3×20 mL). The combined organic extracts were washed with water and brine, dried and concentrated to give tert-butyl 7-(5-(4-(1-acetamido-2-ethoxy-2-oxoethyl)-4-hydroxypiperidin-1-yl)pentyl)-3,4-dihydro-1,8-naphthyridine-1(2H)-carboxylate (43 mg) Yield 92% (ESI 547 (M+H)+).

Step 6: ethyl 2-acetamido-2-(4-hydroxy-1-(5-(5,6,7,8-tetrahydro-1,8-naphthyridin-2-yl)pentyl)piperidin-4-yl)acetate-P1

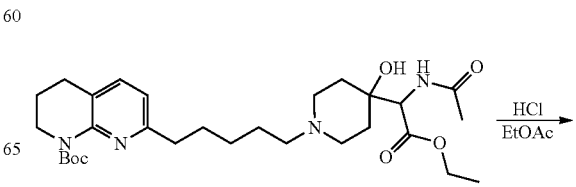

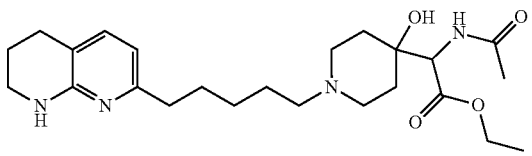

Tert-butyl 7-(5-(4-(1-acetamido-2-ethoxy-2-oxoethyl)-4-hydroxypiperidin-1-yl)pentyl)-3,4-dihydro-1,8-naphthyridine-1(2H)-carboxylate-P1 (70 mg, 0.13 mmol) was treated with 4 N HCl/dioxane (2 mL) at room temperature overnight. Solvent was removed in vacuo to give ethyl 2-acetamido-2-(4-hydroxy-1-(5-(5,6,7,8-tetrahydro-1,8-naphthyridin-2-yl)pentyl)piperidin-4-yl)acetate-P1 as light yellow solid (17 mg). Yield 70% (ESI 447 (M+H)+).

Step 7: 2-acetamido-2-(4-hydroxy-1-(5-(5,6,7,8-tetrahydro-1,8-naphthyridin-2-yl)pentyl)piperidin-4-yl)acetic Acid (Compounds 8-P1 and 8-P2)

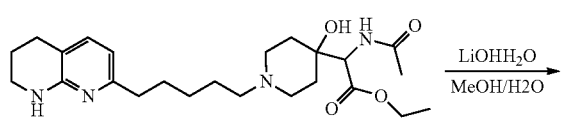

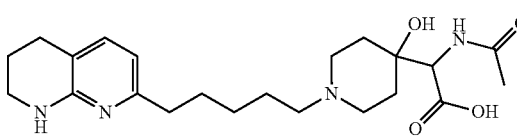

Ethyl 2-acetamido-2-(4-hydroxy-1-(5-(5,6,7,8-tetrahydro-1,8-naphthyridin-2-yl)pentyl)piperidin-4-yl)acetate-P1 (81 mg, 0.18 mmol) was treated with LiOH—H$_2$O (23 mg, 0.54 mmol) in EtOH (4 mL) and H$_2$O (1 mL) at room temperature for 2 hours. Solvent was removed in vacuo, and the residue was purified by Prep-HPLC A (33-65% MeCN) to give enantiomeric product compound 8-P1 (42 mg) as white solid. Compound 8-P2 (17 mg of a white solid) was prepared by the same procedures starting with tert-butyl 4-(1-acetamido-2-ethoxy-2-oxoethyl)-4-hydroxypiperidine-1-carboxylate-P2 from step 3.

Compound 8-P1 LC/MS A: 100% purity, UV=214 nm, Rt=0.95 mim, ESI 419 (M+H)+. $^1$H NMR (500 MHz, MeOD) δ 7.15 (d, J=7.3 Hz, 1H), 6.38 (d, J=7.3 Hz, 1H), 4.38 (s, 1H), 3.43-3.35 (m, 2H), 3.28 (br s, 2H), 3.08 (m, 2H), 2.99-2.90 (m, 2H), 2.71 (t, J=6.3 Hz, 2H), 2.55 (t, J=7.5 Hz, 2H), 2.04 (s, 3H), 1.94-1.81 (m, 5H), 1.80-1.64 (m, 5H), 1.45-1.32 (m, 2H). Chiral SFC A: ee 69%, Rt=4.34 min.

Compound 8-P2 LC/MS A: 100% purity, UV=214 nm, Rt=0.94 mim, ESI 419 (M+H)+. $^1$H NMR (500 MHz, MeOD) δ 7.15 (d, J=7.3 Hz, 1H), 6.38 (d, J=7.3 Hz, 1H), 4.36 (s, 1H), 3.43-3.36 (m, 2H), 3.26 (m, 2H), 3.06 (m, 2H), 2.92 (m, 2H), 2.71 (t, J=6.2 Hz, 2H), 2.55 (t, J=7.5 Hz, 2H), 2.04 (s, 3H), 1.94-1.79 (m, 5H), 1.78-1.64 (m, 5H), 1.43-1.23 (m, 2H). Chiral SFC A: ee 60%, Rt=3.55 min.

Example 9: Preparation of 2-(3-hydroxy-1-(5-(5,6,7,8-tetrahydro-1,8-naphthyridin-2-yl)pentanoyl)azetidin-3-yl)acetic Acid (Compound 9)

Step 1: ethyl 2-(3-hydroxy-1-(5-(5,6,7,8-tetrahydro-1,8-naphthyridin-2-yl)pentanoyl)azetidin-3-yl)acetate

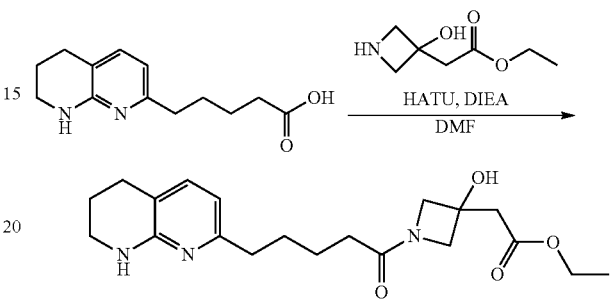

A mixture of 5-(5,6,7,8-tetrahydro-1,8-naphthyridin-2-yl)pentanoic acid dihydrochloride (100 mg, 0.32 mmol), HATU (150 mg, 0.40 mmol), ethyl 2-(3-hydroxyazetidin-3-yl)acetate hydrochloride (76 mg, 0.40 mmol), and DIEA (206 mg, 1.60 mmol) in DMF (2 mL) was stirred overnight. Solvent was removed in vacuo, and the residue was purified by silica gel column (EtOAc) to give ethyl 2-(3-hydroxy-1-(5-(5,6,7,8-tetrahydro-1,8-naphthyridin-2-yl)pentanoyl)azetidin-3-yl)acetate as a light yellow solid (60 mg). Yield 49% (100% purity, UV=214 nm, ESI 376 (M+H)+).

Step 2: 2-(3-hydroxy-1-(5-(5,6,7,8-tetrahydro-1,8-naphthyridin-2-yl)pentanoyl) azetidin-3-yl)acetic Acid (Compound 9)

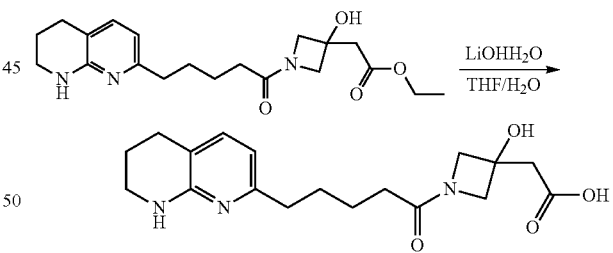

Ethyl 2-(3-hydroxy-1-(5-(5,6,7,8-tetrahydro-1,8-naphthyridin-2-yl)pentanoyl)azetidin-3-yl)acetate (80 mg, 0.21 mmol) was treated with LiOH—H$_2$O (19 mg, 0.42 mmol) in THF (4 mL) and H$_2$O (2 mL) for 2 hours at room temperature. Solvent was removed in vacuo, and the residue was purified by Prep-HPLC A (33-65% MeCN) to give compound 9 as a white solid (49 mg 88% yield). LC/MS B: 100% purity, UV=214 nm, Rt=1.05 min, ESI 348 (M+H)$^+$. $^1$H NMR (400 MHz, MeOD) δ 7.26 (d, J=7.3 Hz, 1H), 6.43 (d, J=7.3 Hz, 1H), 4.39 (d, J=8.9 Hz, 1H), 4.08-3.97 (m, 1H), 3.83 (d, J=10.2 Hz, 2H), 3.47-3.36 (m, 1H), 2.74 (t, J=6.2 Hz, 2H), 2.65-2.49 (m, 2H), 2.27 (m, 4H), 2.16 (dd, J=13.9, 7.0 Hz, 1H), 1.90 (m, 2H), 1.68 (m, 4H).

Example 10: Preparation of 2-(4-methoxy-1-((3-(5,6,7,8-tetrahydro-1,8-naphthyridin-2-yl)propyl)carbamoyl)piperidin-4-yl)acetic Acid (Compound 10)

Step 1: benzyl 4-(2-ethoxy-2-oxoethyl)-4-hydroxypiperidine-1-carboxylate

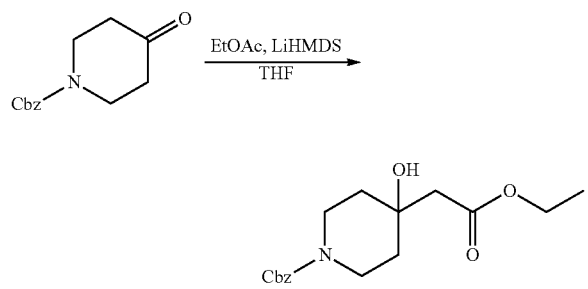

To a solution of LiHMDS (1 M in THF, 4.50 mmol, 4.50 mL) in anhydrous THF (10 mL) at −78° C. under nitrogen was added slowly a solution of ethyl acetate (4.29 mmol, 0.420 mL) in anhydrous THF (5 mL). The reaction was stirred for 15 min at −78° C., then removed from the bath and stirred for 10 minutes more. The reaction was cooled back to −78° C., and benzyl 4-oxopiperidine-1-carboxylate (4.29 mmol, 0.853 mL) in THF (5 mL) was added slowly. The reaction was stirred for 30 min at −78° C., then allowed to warm to room temperature and stirred for 30 minutes more. The reaction was quenched with saturated aqueous NH$_4$Cl and extracted twice with EtOAc. The organic extracts were washed with brine, combined, dried over Na$_2$SO$_4$, filtered, and concentrated under vacuum The residue was purified by silica gel column (40 g SiO$_2$, 0-50% EtOAc/Hex) to give the desired product benzyl 4-(2-ethoxy-2-oxoethyl)-4-hydroxypiperidine-1-carboxylate (910 mg). Yield 66% (88% purity, ESI 344.2 (M+Na)$^+$).

Step 2: benzyl 4-(2-ethoxy-2-oxoethyl)-4-methoxypiperidine-1-carboxylate

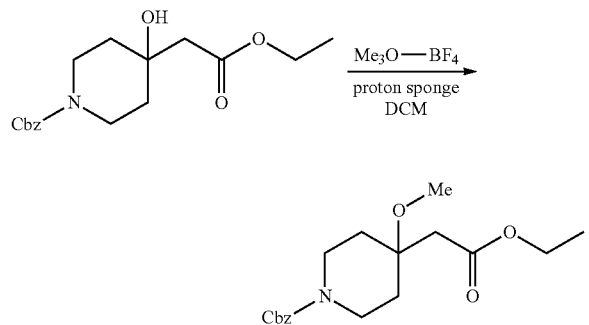

Benzyl 4-(2-ethoxy-2-oxoethyl)-4-hydroxypiperidine-1-carboxylate (2.07 mmol, 665 mg) was rotavapped twice with toluene, then combined with proton sponge (4.14 mmol, 0.887 g), and trimethyloxonium tetrafluoroborate (4.14 mmol, 0.612 g) in dry dichloromethane (7 mL) under nitrogen. The reaction was stirred overnight. Additional proton sponge (4.14 mmol, 0.887 g) and trimethyloxonium tetrafluoroborate (4.14 mmol, 0.612 g) were added, and the reaction was stirred for another 3 hours, then filtered, washed with water and brine, dried over sodium sulfate, filtered, and concentrated under vacuum. The residue was purified by silica gel column (24 g SiO$_2$, 0-50% EtOAc:hexanes) to give the desired product benzyl 4-(2-ethoxy-2-oxoethyl)-4-methoxypiperidine-1-carboxylate (259 mg). Yield 35% (90% purity, ESI 358.2 (M+Na)$^+$), $^1$H NMR (400 MHz, CDCl$_3$) δ 7.37-7.29 (m, 5H), 5.12 (s, 2H), 4.14 (t, J=7.2 Hz, 2H), 3.90 (br s, 2H), 3.13 (br s, 2H), 2.49 (br s, 2H), 1.89 (d, J=5.6 Hz, 2H), 1.59 (ddd, J=4.8, 12.0, 14.0 Hz, 2H), 1.26 (t, J=7.2 Hz, 3H).

Step 3: ethyl 2-(4-methoxypiperidin-4-yl)acetate

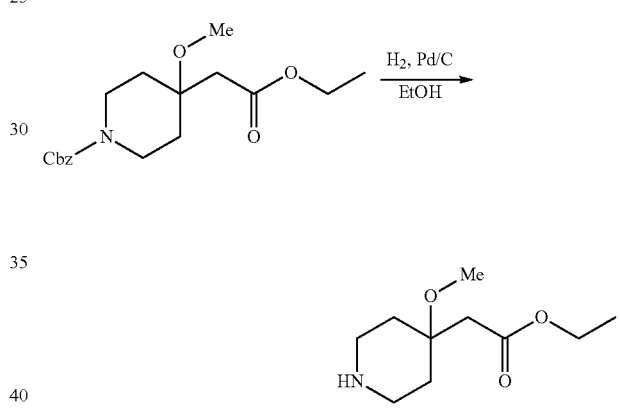

Benzyl 4-(2-ethoxy-2-oxoethyl)-4-methoxypiperidine-1-carboxylate (0.772 mmol, 0.259 g) was hydrogenated overnight under balloon hydrogen over 10% Pd/C (50% wet, 0.16 g) in ethanol (5 mL). The reaction was filtered and concentrated under vacuum to give ethyl 2-(4-methoxypiperidin-4-yl)acetate (0.154 g) as an oil. Yield 99% (85% purity).

Step 4: ethyl 2-(4-methoxy-1-((3-(5,6,7,8-tetrahydro-1,8-naphthyridin-2-yl)propyl) carbamoyl) piperidin-4-yl)acetate

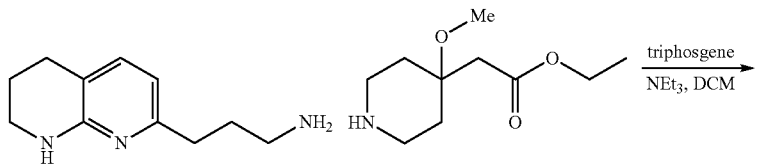

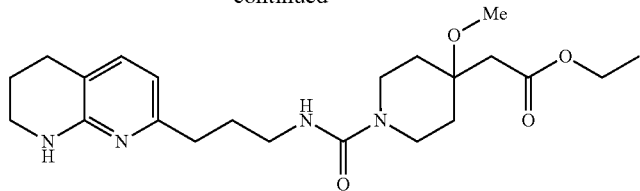

To a solution of triphosgene (0.123 mmol, 0.037 g) in dry DCM (0.5 mL) under nitrogen was added dropwise 3-(5,6,7,8-tetrahydro-1,8-naphthyridin-2-yl)propan-1-amine hydrochloride (0.290 mmol, 0.066 g) and triethylamine (0.92 mmol, 0.13 mL) in DCM (1.5 mL). The reaction was stirred for 30 minutes, then ethyl 2-(4-methoxypiperidin-4-yl)acetate (0.308 mmol, 0.062 g) and triethylamine (0.62 mmol, 0.085 mL) in DCM (1.5 mL) were added slowly. The reaction was stirred for 5 hours, then diluted with EtOAc, washed with saturated aqueous NaHCO$_3$ and brine, dried over sodium sulfate, filtered, and concentrated under vacuum. The residue was purified by silica gel column (12 g SiO$_2$, 0-10% MeOH/DCM) to give the desired product ethyl 2-(4-methoxy-1-((3-(5,6,7,8-tetrahydro-1,8-naphthyridin-2-yl)propyl)carbamoyl)piperidin-4-yl)acetate (0.095 g). Yield 74% (90% purity, ESI 419.2 (M+H)$^+$).

Step 5: 2-(4-methoxy-1-((3-(5,6,7,8-tetrahydro-1,8-naphthyridin-2-yl)propyl) carbamoyl)piperidin-4-yl)acetic Acid (Compound 10)

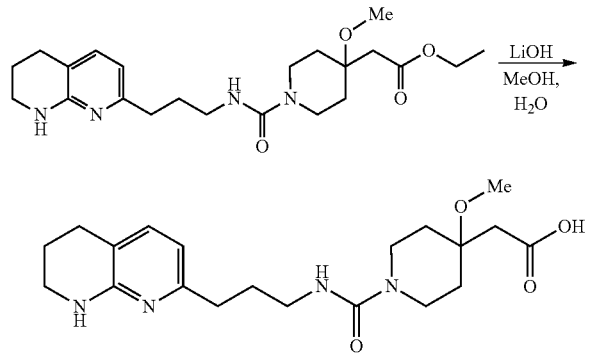

Ethyl 2-(4-methoxy-1-((3-(5,6,7,8-tetrahydro-1,8-naphthyridin-2-yl)propyl)carbamoyl)piperidin-4-yl)acetate (0.227 mmol, 0.095 g) was treated with LiOH (0.5 mmol, 0.012 g) in water (0.5 mL) and methanol (0.5 mL) for 3 hours at room temperature and 1 hour at 60° C. The reaction was neutralized to pH 6 with AcOH, diluted with water and MeOH, purified by prep HPLC C (5-95% MeCN) and lyophilized to give compound 10 (27 mg, 31% yield) as a white solid. LC/MS F: 100% purity, UV=215 nm, Rt=3.463 min, ESI 391.2 (M+H)$^+$. $^1$H NMR (400 MHz, MeOD) δ 7.44 (d, J=7.2 Hz, 1H), 6.52 (d, J=7.2 Hz, 1H), 3.75-3.71 (m, 2H), 3.43 (t, J=5.6 Hz, 2H), 3.28-3.26 (m, 2H), 3.23 (s, 3H), 3.07 (dt, J=1.2, 13.6, 13.6 Hz, 2H), 2.76 (t, J=6.2 Hz, 2H), 2.71-2.67 (m, 2H), 2.41 (s, 2H), 2.35 (dt, J=4.0, 13.6, 13.6 Hz, 2H), 1.94-1.88 (m, 2H), 1.85-1.78 (m, 2H), 1.63 (d, J=13.6 Hz, 2H).

Example 11: Preparation of 2-(4-methoxy-1-((3-(5,6,7,8-tetrahydro-1,8-naphthyridin-2-yl)propyl)carbamoyl)piperidin-4-yl)acetic Acid (Compounds 11-P1 and 11-P2)

Step 1: tert-butyl 4-(2-ethoxy-2-oxoethyl)-4-hydroxy-3-methoxypiperidine-1-carboxylate

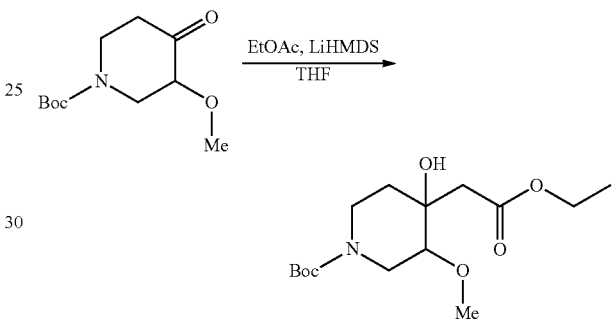

To a solution of ethyl acetate (1.20 mmol, 0.117 mL) in anhydrous THF (7 mL) at −78° C. under nitrogen was added slowly a solution of LiHMDS (1 M in THF, 1.2 mmol, 1.2 mL). The reaction was stirred for 15 min at −78° C., then removed from the bath and stirred for 7 minutes more. The reaction was cooled back to −78 C, and tert-butyl 3-methoxy-4-oxopiperidine-1-carboxylate (1 mmol, 0.229 g) in anhydrous THF (3 mL) was added slowly. The reaction was stirred for 30 min at −78° C., then allowed to warm to room temperature and stirred for 30 minutes more. The reaction was quenched with saturated aqueous NH$_4$Cl and extracted twice with EtOAc. The organic extracts were washed with brine, combined, dried over Na$_2$SO$_4$, filtered and concentrated under vacuum. The residue was purified by silica gel column (24 g SiO$_2$, 0-50% EtOAc/Hex) to give two diastereomeric products of tert-butyl 4-(2-ethoxy-2-oxoethyl)-4-hydroxy-3-methoxypiperidine-1-carboxylate: P1 (57 mg, 18%) and P2 (87 mg, 27%), plus some mixed fractions (90 mg).

P1 (ESI 340.2 (M+Na)$^+$), $^1$H NMR (400 MHz, CDCl$_3$) δ 4.22-4.14 (m, 2H), 4.13-4.03 (m, 1H), 3.91 (br s, 1H), 3.74-3.67 (m, 1H), 3.36 (s, 3H), 3.24 (d, J=6.4 Hz, 1H), 3.12-3.04 (m, 1H), 2.68 (d, J=16 Hz, 1H), 2.45 (d, J=16.4 Hz, 1H), 1.75 (dt, J=4.8, 12.8, 12.8 Hz, 1H), 1.46 (s, 9H), 1.43-1.40 (m, 1H), 1.28 (t, J=7.2 Hz, 3H).

P2 (ESI 340.2 (M+Na)$^+$), $^1$H NMR (400 MHz, CDCl$_3$) δ 4.16 (q, J=7.2 Hz, 2H), 4.07-4.01 (m, 1H), 3.80-3.72 (m, 1H), 3.41 (s, 3H), 3.27 (br s, 1H), 3.16-3.08 (m, 1H), 2.62 (d, J=14.4 Hz, 1H), 2.43 (d, J=14.4 Hz, 1H), 1.79 (td, J=2.8, 2.8, 14.0 Hz, 1H), 1.59-1.52 (m, 1H), 1.46 (s, 9H), 1.28 (t, J=7.2 Hz, 3H).

Step 2: ethyl 2-(4-hydroxy-3-methoxypiperidin-4-yl)acetate-P1 Hydrochloride

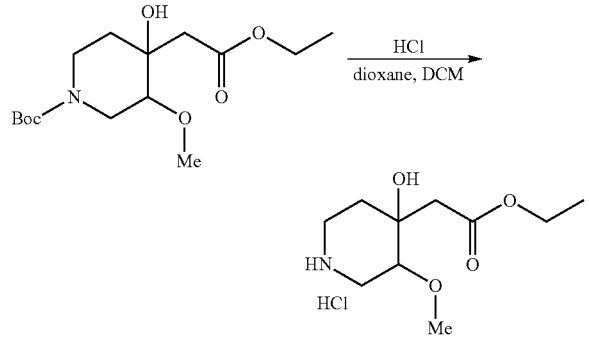

Tert-butyl 4-(2-ethoxy-2-oxoethyl)-4-hydroxy-3-methoxypiperidine-1-carboxylate-P1 (0.180 mmol, 57 mg) was treated with HCl (4M in dioxane, 2.0 mmol, 0.5 mL) in DCM (2 mL) for 1 hour. The reaction was concentrated under vacuum to give ethyl 2-(4-hydroxy-3-methoxypiperidin-4-yl)acetate-P1 hydrochloride, used without further purification. (ESI 218.2 (M+H)$^+$).

Step 3: ethyl 2-(4-hydroxy-3-methoxy-1-(5-(5,6,7,8-tetrahydro-1,8-naphthyridin-2-yl)pentanoyl)piperidin-4-yl)acetate-P1

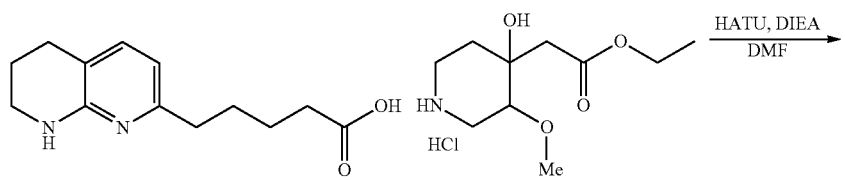

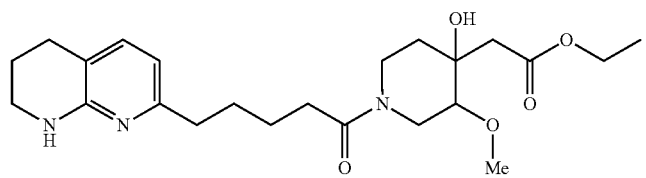

A mixture of ethyl 2-(4-hydroxy-3-methoxypiperidin-4-yl)acetate-P1 hydrochloride (0.18 mmol, 0.046 g), 5-(5,6,7,8-tetrahydro-1,8-naphthyridin-2-yl)pentanoic acid (0.216 mmol, 0.051 g), DIEA (0.720 mmol, 0.126 mL) and HATU (0.234 mmol, 0.089 g) in DMF (6.46 mmol, 0.5 mL) was stirred at room temp overnight. The mixture was diluted with ethyl acetate, washed with saturated aqueous NaHCO$_3$ and brine, dried over sodium sulfate, filtered and concentrated under vacuum. The residue was purified by silica gel column (12 g SiO$_2$, 0-10% MeOH:DCM) to give ethyl 2-(4-hydroxy-3-methoxy-1-(5-(5,6,7,8-tetrahydro-1,8-naphthyridin-2-yl)pentanoyl)piperidin-4-yl)acetate-P1 (40 mg, 51.3%). (ESI 434.2 (M+H)$^+$).

Step 4: 2-(4-methoxy-1-((3-(5,6,7,8-tetrahydro-1,8-naphthyridin-2-yl)propyl) carbamoyl)piperidin-4-yl) acetic Acid (Compounds 11-P1 and 11-P2)

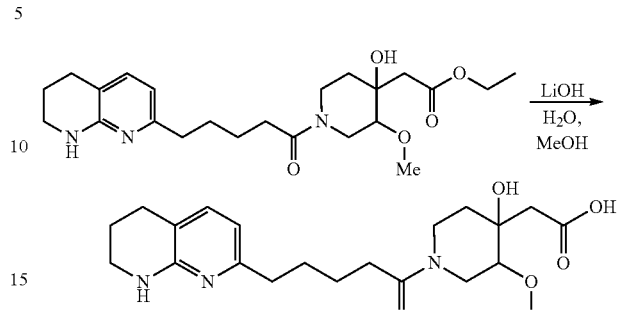

Ethyl 2-(4-hydroxy-3-methoxy-1-(5-(5,6,7,8-tetrahydro-1,8-naphthyridin-2-yl)pentanoyl)piperidin-4-yl)acetate-P1 (0.092 mmol, 40 mg) was treated with LiOH (0.50 mmol, 0.012 g) in water (0.5 mL) and methanol (0.5 mL) for 1 hour at 60° C. The reaction was neutralized to pH 5 with AcOH, diluted with water and MeOH, purified by prep HPLC C (5-60% MeCN) and lyophilized to give compound 11-P1 (13.7 mg, 36.6%) as a white solid. The diastereomeric product compound 11-P2 (16.5 mg of a white solid) was prepared in the same manner starting with tert-butyl 4-(2-ethoxy-2-oxoethyl)-4-hydroxy-3-methoxypiperidine-1-carboxylate-P2 from step 1.

Compound 11-P1 LC/MS F: 100% purity, UV=215 nm, Rt=3.187 min, ESI 406.2 (M+H)$^+$. $^1$H NMR (400 MHz, MeOD) conformational isomers result in two sets of peaks δ 7.46-7.42 (m, 1H), 6.55-6.51 (m, 1H), 4.62 (td, J=2.4, 2.4, 13.6 Hz, 0.5H), 4.30-4.26 (m, 0.5H), 3.94-3.89 (m, 0.5H), 3.72-3.68 (m, 0.5H), 3.53-3.37 (m, 4H), 3.26 (s, 2H), 3.21-3.18 (m, 1H), 3.04 (dd, J=1.2, 13.6 Hz, 0.5H), 2.95 (dt, J=2.4, 13.2, 13.2 Hz, 0.5H), 2.78 (t, J=6.4 Hz, 2H), 2.68-2.23 (m, 6H), 2.09 (dt, J=4.4, 13.2, 13.2 Hz, 1H), 1.95-1.81 (m, 2H), 1.79-1.61 (m, 4H), 1.53-1.2 (m, 1H).

Compound 11-P2 LC/MS F: 100% purity, UV=215 nm, Rt=3.176 min, ESI 406.2 (M+H)$^+$. $^1$H NMR (400 MHz, MeOD) conformational isomers result in two sets of peaks δ 7.43 (d, J=7.2 Hz, 1H), 6.50-6.47 (m, 1H), 4.53 (ddd, J=2.0, 4.8, 12.0 Hz, 0.5H), 4.28-4.23 (m, 1H), 3.99 (ddd, J=2.0, 5.0, 12.8 Hz, 0.5H), 3.75-3.69 (m, 0.5H), 3.58 (s, 1H), 3.46-3.33 (m, 4.5H), 3.27-3.19 (m, 1H), 2.94-2.58 (m, 7H), 2.45-2.19 (m, 2H), 1.95-1.89 (m, 2H), 1.86-1.52 (m, 6H).

Additional Examples

Compounds 12-56 were prepared using general procedures based on the method used to prepare compounds 1-11.

2-(1-hydroxy-4-(4-((5,6,7,8-tetrahydro-1,8-naphthyridin-2-yl)methyl)piperidine-1-carbonyl)cyclohexyl)acetic Acid (Compound 12)

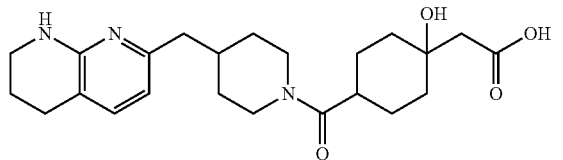 [SMILES: O=C(O)CC1(O)CCC(C(=O)N2CCC(Cc3ccc4c(n3)NCCC4)CC2)CC1]

Compound 12 LC/MS A: 98% purity, UV=214 nm, Rt=1.42 min, ESI 416.4 (M+H)+. ¹H NMR (400 MHz, MeOD) δ 7.39 (d, J=7.3 Hz, 1H), 6.49 (d, J=7.3 Hz, 1H), 4.51 (d, J=13.4 Hz, 1H), 4.03 (d, J=13.2 Hz, 1H), 3.47-3.38 (m, 2H), 3.04 (t, J=12.1 Hz, 1H), 2.80-2.45 (m, 8H), 2.00-1.47 (m, 13H), 1.30-1.06 (m, 2H).

2-(4-hydroxy-1-(4-((5,6,7,8-tetrahydro-1,8-naphthyridin-2-yl)methyl)piperidine-1-carbonyl)piperidin-4-yl)acetic Acid (Compound 13)

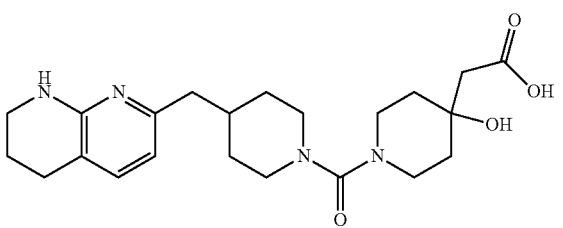 [SMILES: O=C(O)CC1(O)CCN(C(=O)N2CCC(Cc3ccc4c(n3)NCCC4)CC2)CC1]

Compound 13 LC/MS A: 98% purity, UV=214 nm, Rt=1.42 min, ESI 417.4 (M+H)+. ¹H NMR (400 MHz, MeOD) δ 7.41 (d, J=7.3 Hz, 1H), 6.50 (d, J=7.3 Hz, 1H), 3.69 (d, J=13.2 Hz, 2H), 3.67-3.32 (m, 4H), 3.27-3.20 (m, 2H), 2.81-2.76 (m, 4H), 2.57 (d, J=7.2 Hz, 2H), 2.36 (s, 2H), 1.95-1.71 (m, 3H), 1.78-1.47 (m, 6H), 1.29-1.22 (m, 2H).

2-(1-hydroxy-4-(4-(5,6,7,8-tetrahydro-1,8-naphthyridin-2-yl)piperidine-1-carbonyl) cyclohexyl)acetic Acid (Compound 14)

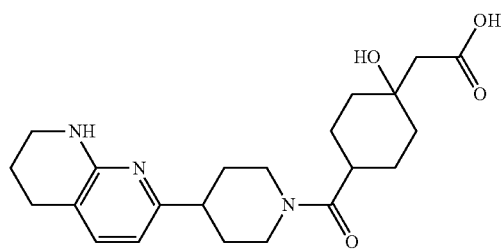 [SMILES: O=C(O)CC1(O)CCC(C(=O)N2CCC(c3ccc4c(n3)NCCC4)CC2)CC1]

Compound 14 LC/MS A: 99% purity, UV=214 nm, Rt=1.41 min, ESI 402.4 (M+H)+. ¹H NMR (400 MHz, MeOD) δ 8.41 (s, 0.42H), 7.42 (d, J=7.3 Hz, 1H), 6.52 (d, J=7.4 Hz, 1H), 4.70 (d, J=12.6 Hz, 1H), 4.18 (d, J=13.4 Hz, 1H), 3.51-3.36 (m, 2H), 3.19 (t, J=12.8 Hz, 1H), 2.95-2.60 (m, 5H), 2.60-2.30 (m, 2H), 2.08-1.44 (m, 14H).

2-(4-hydroxy-1-(4-(5,6,7,8-tetrahydro-1,8-naphthyridin-2-yl)piperidine-1-carbonyl) piperidin-4-yl)acetic Acid (Compound 15)

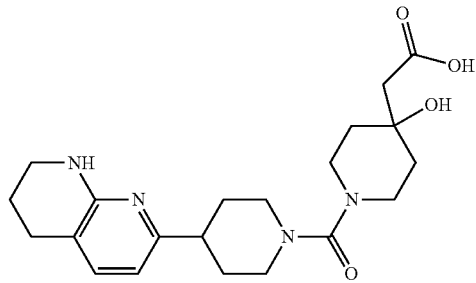 [SMILES: O=C(O)CC1(O)CCN(C(=O)N2CCC(c3ccc4c(n3)NCCC4)CC2)CC1]

Compound 15 LC/MS A: 99% purity, UV=214 nm, Rt=1.40 min, ESI 403.3 (M+H)+. ¹H NMR (400 MHz, MeOD) δ 7.37 (d, J=7.4 Hz, 1H), 6.50 (d, J=7.4 Hz, 1H), 3.81 (d, J=13.2 Hz, 2H), 3.58-3.37 (m, 4H), 3.28-3.19 (m, 2H), 2.93 (t, J=12.0 Hz, 2H), 2.80-2.64 (m, 3H), 2.38 (s, 2H), 1.98-1.79 (m, 4H), 1.75-1.56 (m, 6H).

2-(1-hydroxy-4-((2-(5,6,7,8-tetrahydro-1,8-naphthyridin-2-yl)ethyl)carbamoyl) cyclohexyl)acetic Acid (Compound 16)

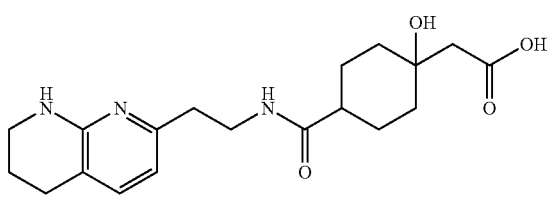 [SMILES: O=C(O)CC1(O)CCC(C(=O)NCCc2ccc3c(n2)NCCC3)CC1]

Compound 16 LC/MS A: 100% purity, UV=214 nm, Rt=1.31 min, ESI 362.3 (M+H)+. 1H NMR (400 MHz, CD3OD) δ 7.35 (d, J=7.2 Hz, 1H), 6.47 (d, J=7.6 Hz, 1H), 3.49-3.42 (m, 4H), 2.80-2.75 (m, 4H), 2.48 (s, 2H), 2.20-2.16 (m, 1H), 1.93-1.84 (m, 4H), 1.78-1.70 (m, 2H), 1.64-1.42 (m, 4H).

2-(4-hydroxy-1-((2-(5,6,7,8-tetrahydro-1,8-naphthyridin-2-yl)ethyl)carbamoyl) piperidin-4-yl)acetic Acid (Compound 17)

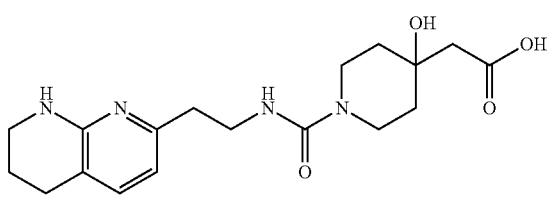 [SMILES: O=C(O)CC1(O)CCN(C(=O)NCCc2ccc3c(n2)NCCC3)CC1]

Compound 17 LC/MS A: 100% purity, UV=214 nm, Rt=1.42 min, ESI 363.3 (M+H)+. 1H NMR (400 MHz, CD3OD) δ 7.14 (d, J=7.2 Hz, 1H), 6.37 (d, J=7.6 Hz, 1H), 3.67-3.63 (m, 2H), 3.42-3.36 (m, 4H), 3.21 (t, J=12.8 Hz, 2H), 2.72-2.67 (m, 4H), 2.67 (s, 2H), 1.91-1.84 (m, 2H), 1.66-1.59 (m, 2H), 1.52-1.43 (m, 2H).

2-(1-hydroxy-4-((3-(5,6,7,8-tetrahydro-1,8-naphthyridin-2-yl)propyl)carbamoyl) cyclohexyl)acetic Acid (Compound 18)

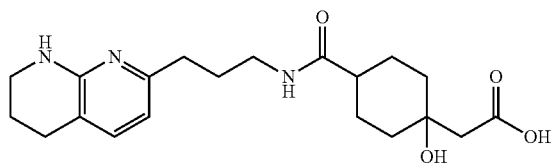 [SMILES: O=C(O)CC1(O)CCC(C(=O)NCCCc2ccc3c(n2)NCCC3)CC1]

Compound 18 LC/MS A: 99.0% purity, UV=214 nm, Rt=1.33 min, ESI 376.4 (M+H)+. 1H NMR (400 MHz, CD3OD) δ 7.30 (d, J=7.6 Hz, 1H), 6.40 (d, J=7.2 Hz, 1H), 3.35-3.31 (m, 2H), 3.17-3.08 (m, 2H), 2.66 (t, J=6.2 Hz, 2H), 2.59-2.50 (m, 2H), 2.34-2.18 (m, 2H), 2.06-1.95 (m, 2H), 1.84-1.66 (m, 9H), 1.38-1.32 (m, 2H).

2-(4-hydroxy-1-((3-(5,6,7,8-tetrahydro-1,8-naphthyridin-2-yl)propyl)carbamoyl) piperidin-4-yl)acetic Acid (Compound 19)

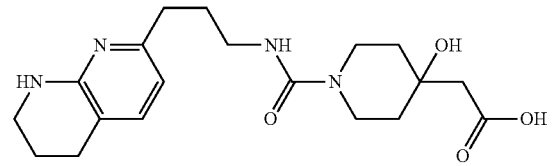 [SMILES: O=C(O)CC1(O)CCN(C(=O)NCCCc2ccc3c(n2)NCCC3)CC1]

Compound 19 LC/MS A: 99% purity, UV=214 nm, Rt=1.30 min, ESI 377.4 (M+H)+. ¹H NMR (400 MHz, MeOD) δ 7.43 (d, J=7.4 Hz, 1H), 6.53 (d, J=7.3 Hz, 1H), 3.74 (d, J=13.9 Hz, 2H), 3.44 (t, J=5.6 Hz, 2H), 3.33-3.17 (m, 4H), 2.77 (t, J=6.2 Hz, 2H), 2.67 (t, J=8.0 Hz, 2H), 2.36 (s, 2H), 2.13-2.08 (m, 2H), 1.99-1.73 (m, 4H), 1.48 (d, J=13.5 Hz, 2H).

2-(1-hydroxy-4-((4-(5,6,7,8-tetrahydro-1,8-naphthyridin-2-yl)butyl)carbamoyl) cyclohexyl)acetic Acid (Compound 20)

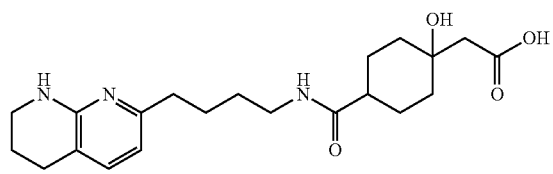 [SMILES: O=C(O)CC1(O)CCC(C(=O)NCCCCc2ccc3c(n2)NCCC3)CC1]

Compound 20 LC/MS A: 99.5% purity, UV=214 nm, Rt=1.37 min, ESI 390.4 (M+H)+. 1H NMR (400 MHz, DMSO-d6) δ 7.68-7.59 (m, 1H), 7.01 (d, J=7.6 Hz, 1H), 6.35 (s, 1H), 6.23 (d, J=7.2 Hz, 1H), 3.25-3.20 (m, 2H), 3.03-2.97 (m, 2H), 2.59 (t, J=6.2 Hz, 2H), 2.40 (t, J=7.2 Hz, 2H), 2.32-2.24 (m, 2H), 2.11-2.03 (m, 1H), 1.83-1.23 (m, 14H).

2-(4-hydroxy-1-((4-(5,6,7,8-tetrahydro-1,8-naphthyridin-2-yl)butyl)carbamoyl) piperidin-4-yl)acetic Acid Formic Acid Salt (Compound 21)

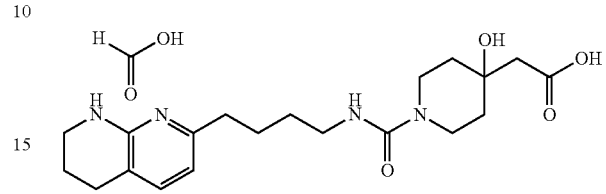

Compound 21 LC/MS A: 98.1% purity, UV=214 nm, Rt=1.36 min, ESI 391.3 (M+H)+. 1H NMR (400 MHz, CD3OD) δ 8.27 (s, 1.8H, formate), 7.51 (d, J=7.2 Hz, 1H), 6.54 (d, J=7.2 Hz, 1H), 3.76-3.72 (m, 2H), 3.47 (t, J=5.6 Hz, 2H), 3.23-3.19 (m, 4H), 2.80 (t, J=6.0 Hz, 2H), 2.68 (t, J=7.6 Hz, 2H), 2.44 (s, 2H), 1.95-1.85 (m, 4H), 1.70-1.54 (m, 6H).

2-(2,6-difluorobenzamido)-2-(4-hydroxy-1-((3-(5,6,7,8-tetrahydro-1,8-naphthyridin-2-yl)propyl)carbamoyl)piperidin-4-yl)acetic Acid (Compound 22)

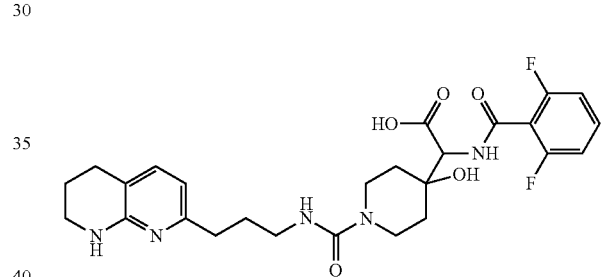

Compound 22 LC/MS A: 99% purity, UV=214 nm, Rt=1.41 min, ESI 532.3 (M+H)+. ¹H NMR (400 MHz, MeOD) δ 7.55-7.36 (m, 2H), 7.04 (t, J=8.1 Hz, 2H), 6.57 (d, J=7.3 Hz, 1H), 4.57 (s, 1H), 3.83 (d, J=13.0 Hz, 2H), 3.55-3.38 (m, 2H), 3.27-3.05 (m, 4H), 2.80 (t, J=6.0 Hz, 2H), 2.65 (t, J=7.2 Hz, 2H), 2.14-1.73 (m, 6H), 1.65-1.59 (m, 2H).

2-acetamido-2-(4-hydroxy-1-((3-(5,6,7,8-tetrahydro-1,8-naphthyridin-2-yl)propyl) carbamoyl)piperidin-4-yl)acetic Acid (Enantiomeric Compounds 23-P1 and 23-P2)

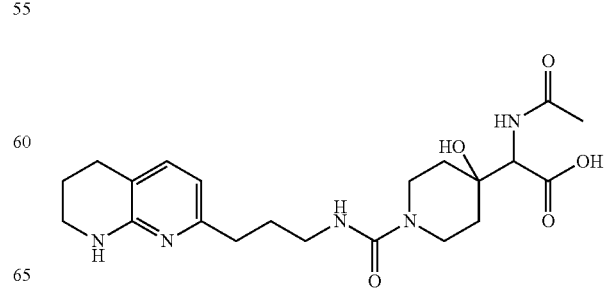

Compound 23-P1 LC/MS A: 100% purity, UV=214 nm, Rt=1.36 min, ESI 434 (M+H)+ ¹H NMR (500 MHz, MeOD) δ 7.36 (d, J=7.3 Hz, 1H), 6.43 (d, J=7.3 Hz, 1H), 4.25 (s, 1H), 3.68 (d, J=6.6 Hz, 2H), 3.37-3.32 (m, 2H), 3.20-3.13 (m, 1H), 3.11-2.99 (m, 3H), 2.67 (t, J=6.1 Hz, 2H), 2.60-2.53 (m, 2H), 1.93 (s, 3H), 1.90-1.80 (m, 3H), 1.77-1.70 (m, 2H), 1.61 (td, J=13.2, 4.5 Hz, 1H), 1.51-1.46 (m, 1H), 1.42-1.37 (m, 1H). Chiral SFC G (45% MeOH): ee 100%, Rt=2.76 min Compound 23-P2 LC/MS A: 100% purity, UV=214 nm, Rt=1.36 min, ESI 434 (M+H)+ ¹H NMR (500 MHz, MeOD) δ 7.35 (d, J=7.3 Hz, 1H), 6.43 (d, J=7.3 Hz, 1H), 4.25 (s, 1H), 3.68 (s, 2H), 3.37-3.33 (m, 2H), 3.17 (t, J=6.5 Hz, 1H), 3.11-2.98 (m, 3H), 2.67 (t, J=6.1 Hz, 2H), 2.61-2.51 (m, 2H), 1.93 (s, 3H), 1.85 (ddd, J=28.5, 12.4, 5.0 Hz, 3H), 1.77-1.70 (m, 2H), 1.61 (td, J=13.1, 4.6 Hz, 1H), 1.48 (dd, J=13.6, 1.9 Hz, 1H), 1.42-1.37 (m, 1H). Chiral SFC G (45% MeOH): ee 87%, Rt=3.53 min 2-(4-hydroxy-1-((3-(5,6,7,8-tetrahydro-1,8-naphthyridin-2-yl)propyl)carbamoyl) piperidin-4-yl)-2-(methylsulfonamido)acetic Acid (Compound 24)

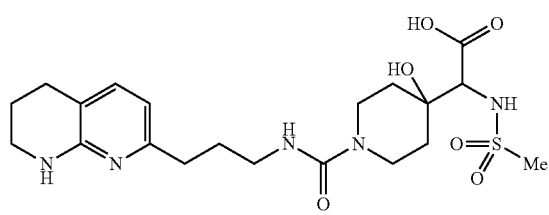 [SMILES: CS(=O)(=O)NC(C(=O)O)C1(O)CCN(C(=O)NCCCc2ccc3c(n2)NCCC3)CC1]

Compound 24 LC/MS A: 97% purity, UV=214 nm, Rt=1.35 min, ESI 470.3 (M+H)+. ¹H NMR (400 MHz, MeOD) δ 7.46 (d, J=7.4 Hz, 1H), 6.56 (d, J=7.3 Hz, 1H), 3.81 (t, J=12.8 Hz, 2H), 3.65 (s, 1H), 3.52-3.40 (m, 2H), 3.28-3.05 (m, 4H), 2.99 (s, 3H), 2.79 (t, J=6.4 Hz, 2H), 2.67 (t, J=7.6 Hz, 2H), 2.02-1.72 (m, 6H), 1.53 (d, J=13.7 Hz, 2H).

2-(4-hydroxy-1-((3-(5,6,7,8-tetrahydro-1,8-naphthyridin-2-yl)propyl)carbamoyl) piperidin-4-yl)-2-phenylacetic Acid (Compound 25)

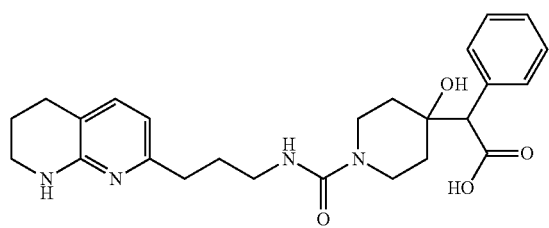 [SMILES: O=C(O)C(c1ccccc1)C1(O)CCN(C(=O)NCCCc2ccc3c(n2)NCCC3)CC1]

Compound 25 LC/MS B: 98% purity, UV=214 nm, Rt=1.07 min, ESI 453.2 (M+H)+. ¹H NMR (400 MHz, MeOD) δ 8.33 (s, 0.36H), 7.58-7.42 (m, 3H), 7.35-7.21 (m, 3H), 6.57 (d, J=7.4 Hz, 1H), 3.76 (d, J=13.1 Hz, 2H), 3.50-3.41 (m, 3H), 3.28-2.98 (m, 4H), 2.82-2.61 (m, 4H), 2.30 (s, 1H), 1.98-1.66 (m, 5H), 1.52 (s, 1H), 1.32 (d, J=13.0 Hz, 1H).

2-(cyclopentanecarboxamido)-2-(4-hydroxy-1-(5-(5,6,7,8-tetrahydro-1,8-naphthyridin-2-yl)pentyl)piperidin-4-yl)acetic Acid (Compound 26)

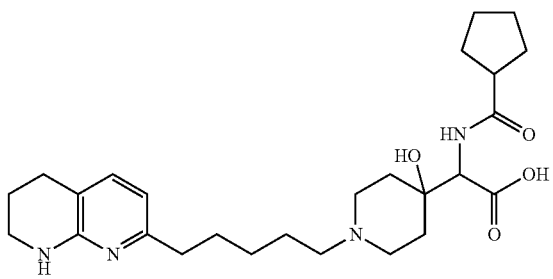 [SMILES: O=C(NC(C(=O)O)C1(O)CCN(CCCCCc2ccc3c(n2)NCCC3)CC1)C1CCCC1]

Compound 26 LC/MS A: 98% purity, UV=214 nm, Rt=1.54 min, ESI 473.5 (M+H)+. 1H NMR (500 MHz, MeOD) δ 7.21 (d, J=7.3 Hz, 1H), 6.44 (d, J=7.3 Hz, 1H), 4.33 (s, 1H), 3.40-3.36 (m, 3H), 3.20-3.01 (m, 4H), 2.78-2.71 (m, 3H), 2.55 (t, J=7.5 Hz, 2H), 1.98-1.85 (m, 7H), 1.82-1.56 (m, 12H), 1.41-1.36 (m, 2H).

2-acetamido-2-(1-hydroxy-4-(4-(5,6,7,8-tetrahydro-1,8-naphthyridin-2-yl)butanamido)cyclohexyl)acetic Acid (Compound 27)

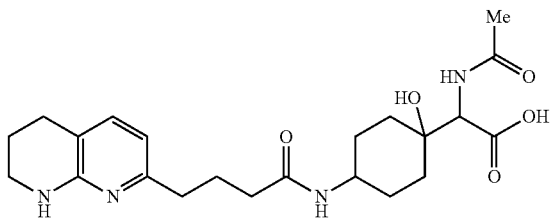 [SMILES: CC(=O)NC(C(=O)O)C1(O)CCC(NC(=O)CCCc2ccc3c(n2)NCCC3)CC1]

Compound 27 LC/MS B: 96% purity, UV=214 nm, Rt=1.06 min, ESI 433.3 (M+H)+. 1H NMR (400 MHz, CD3OD) δ 7.12 (d, J=7.2 Hz, 1H), 6.36 (d, J=7.2 Hz, 1H), 4.32 (s, 1H), 3.59-3.53 (m, 1H), 3.39-3.36 (m, 2H), 2.71-2.68 (m, 2H), 2.54-2.50 (m, 2H), 2.20-2.15 (m, 2H), 2.03 (s, 3H), 1.94-1.88 (m, 4H), 1.69-1.48 (m, 8H).

2-(4-hydroxy-1-(4-(5,6,7,8-tetrahydro-1,8-naphthyridin-2-yl)butanoyl)piperidin-4-yl)acetic Acid (Compound 28)

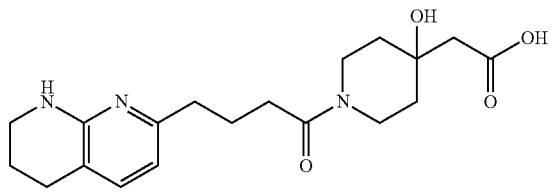 [SMILES: O=C(O)CC1(O)CCN(C(=O)CCCc2ccc3c(n2)NCCC3)CC1]

Compound 28 LC/MS A: 100% purity, UV=214 nm, Rt=1.44 min, ESI 362.2 (M+H)+. ¹H NMR (500 MHz, MeOD) δ 7.44 (d, J=7.3 Hz, 1H), 6.54 (d, J=7.3 Hz, 1H), 4.22 (d, J=13.1 Hz, 1H), 3.71 (d, J=13.6 Hz, 1H), 3.52-3.44 (m, 3H), 3.12 (td, J=12.7, 2.9 Hz, 1H), 2.79 (t, J=6.1 Hz, 2H), 2.72-2.66 (m, 2H), 2.49 (t, J=7.4 Hz, 2H), 2.37 (s, 2H), 1.99-1.91 (m, 4H), 1.78-1.54 (m, 4H).

2-(1-hydroxy-4-((4-(5,6,7,8-tetrahydro-1,8-naphthyridin-2-yl)butyl)amino) cyclohexyl)acetic Acid (Compound 29)

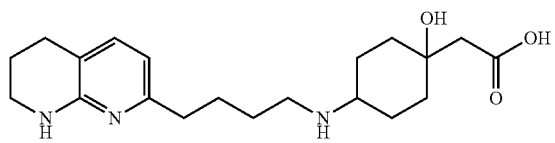 [SMILES: O=C(O)CC1(O)CCC(NCCCCc2ccc3c(n2)NCCC3)CC1]

Compound 29 LC/MS A: 100% purity, UV=214 nm, Rt=1.48 min, ESI 362.2 (M+H)⁺. ¹H NMR (500 MHz, MeOD) δ 7.13 (d, J=7.3 Hz, 1H), 6.38 (d, J=7.3 Hz, 1H), 3.39-3.35 (m, 2H), 3.31 (dt, J=3.1, 1.5 Hz, 1H), 2.97 (dd, J=15.4, 8.2 Hz, 3H), 2.69 (t, J=6.2 Hz, 2H), 2.56 (t, J=7.1 Hz, 2H), 2.23 (s, 1H), 1.91-1.61 (m, 12H), 1.51 (t, J=9.4 Hz, 1H), 1.47-1.36 (m, 2H).

2-benzamido-2-(4-hydroxy-1-((3-(5,6,7,8-tetrahydro-1,8-naphthyridin-2-yl)propyl) carbamoyl) piperidin-4-yl)acetic Acid (Compound 30)

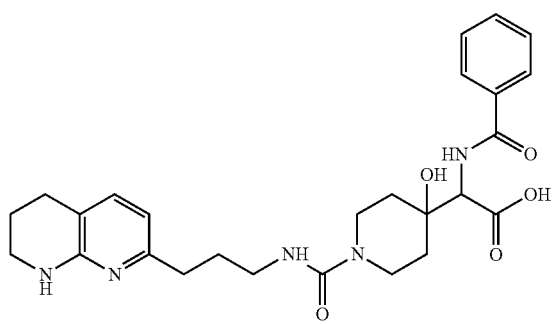 [SMILES: O=C(NC(C(=O)O)C1(O)CCN(C(=O)NCCCc2ccc3c(n2)NCCC3)CC1)c1ccccc1]

Compound 30 LC/MS B: 100% purity, UV=214 nm, Rt=1.15 min, ESI 496.2 (M+H)⁺. ¹H NMR (500 MHz, MeOD) δ 7.91 (d, J=7.3 Hz, 2H), 7.56 (t, J=7.4 Hz, 1H), 7.50 (dd, J=15.0, 7.3 Hz, 3H), 6.57 (d, J=7.4 Hz, 1H), 4.56 (s, 1H), 3.84 (dd, J=26.0, 13.5 Hz, 2H), 3.51-3.44 (m, 2H), 3.31-3.12 (m, 4H), 2.80 (t, J=6.1 Hz, 2H), 2.73-2.65 (m, 2H), 2.25 (t, J=11.0 Hz, 1H), 1.95 (dd, J=11.6, 6.0 Hz, 2H), 1.89-1.79 (m, 3H), 1.71 (d, J=13.8 Hz, 1H), 1.59 (d, J=13.9 Hz, 1H).

2-(4-hydroxy-1-((3-(5,6,7,8-tetrahydro-1,8-naphthyridin-2-yl)propyl)carbamoyl) piperidin-4-yl)-2-(isonicotinamido)acetic Acid (Compound 31)

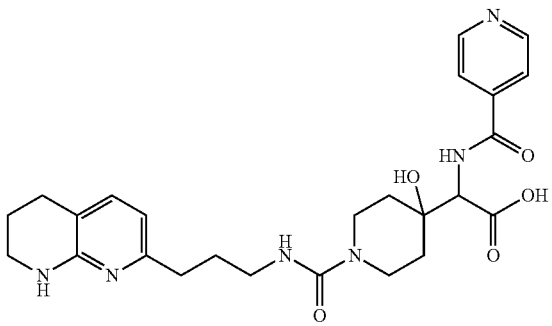 [SMILES: O=C(NC(C(=O)O)C1(O)CCN(C(=O)NCCCc2ccc3c(n2)NCCC3)CC1)c1ccncc1]

Compound 31 LC/MS B: 100% purity, UV=214 nm, Rt=1.04 min, ESI 497.0 (M+H)⁺. 1H NMR (400 MHz, DMSO) δ 8.73 (dd, J=4.4, 1.6 Hz, 2H), 8.32 (d, J=8.8 Hz, 0.8H), 7.78 (dd, J=4.4, 1.6 Hz, 2H), 7.36 (s, 0.8H), 7.15 (d, J=7.3 Hz, 1H), 7.08 (s, 0.6H), 6.48 (t, J=5.4 Hz, 1H), 6.34 (d, J=7.3 Hz, 1H), 4.39 (d, J=8.8 Hz, 1H), 3.74-3.63 (m, 3H), 3.27-3.21 (m, 3H), 3.11-2.86 (m, 5H), 2.62 (t, J=6.0 Hz, 2H), 2.44 (m, 2H), 2.04-1.80 (m, 1H), 1.78-1.43 (m, 7H).

2-(4-hydroxy-1-((3-(5,6,7,8-tetrahydro-1,8-naphthyridin-2-yl)propyl)carbamoyl) piperidin-4-yl)-2-(tetrahydro-2H-pyran-4-carboxamido)acetic Acid (Compound 32)

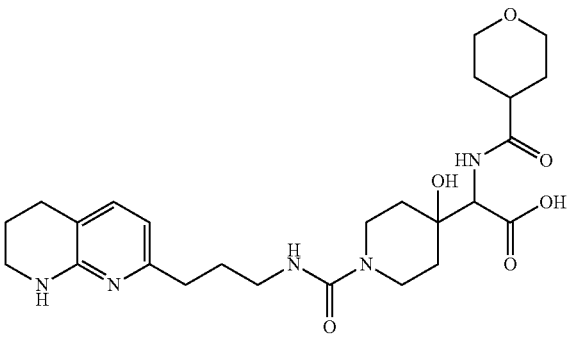 [SMILES: O=C(NC(C(=O)O)C1(O)CCN(C(=O)NCCCc2ccc3c(n2)NCCC3)CC1)C1CCOCC1]

Compound 32 LC/MS A: 100% purity, UV=214 nm, Rt=1.35 min, ESI 504.2 (M+H)⁺. ¹H NMR (500 MHz, Methanol-d₄) δ 7.54 (d, J=7.4 Hz, 1H), 6.61 (d, J=7.5 Hz, 1H), 4.31 (s, 1H), 4.02-3.93 (m, 2H), 3.77 (d, J=13.5 Hz, 2H), 3.54-3.43 (m, 4H), 3.29-3.09 (m, 4H), 2.81 (t, J=6.2 Hz, 2H), 2.71-2.58 (m, 3H), 1.97-1.51 (m, 12H).

2-acetamido-2-(4-hydroxy-1-((2-(5,6,7,8-tetrahydro-1,8-naphthyridin-2-yl)ethyl) carbamoyl)piperidin-4-yl)acetic Acid (Compound 33)

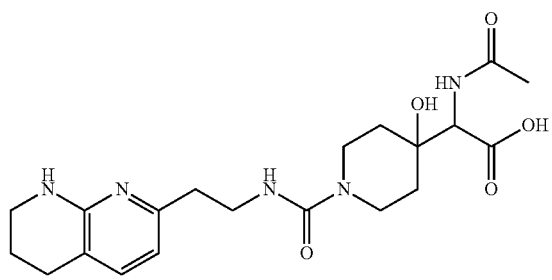 [SMILES: CC(=O)NC(C(=O)O)C1(O)CCN(C(=O)NCCc2ccc3c(n2)NCCC3)CC1]

Compound 33 LC/MS A: 100% purity, UV=214 nm, Rt=1.40 min, ESI 420.3 (M+H)$^+$. $^1$H NMR (500 MHz, Methanol-d$_4$) δ 7.53 (d, J=7.3 Hz, 1H), 6.56 (d, J=7.3 Hz, 1H), 4.36 (s, 1H), 3.76 (t, J=12.9 Hz, 2H), 3.52-3.42 (m, 4H), 3.20-3.09 (m, 2H), 2.87-2.79 (m, 4H), 2.05 (s, 3H), 1.99-1.89 (m, 2H), 1.69-1.49 (m, 4H).

2-acetamido-2-(4-hydroxy-1-((4-(5,6,7,8-tetrahydro-1,8-naphthyridin-2-yl)butyl) carbamoyl)piperidin-4-yl)acetic Acid (Compound 34)

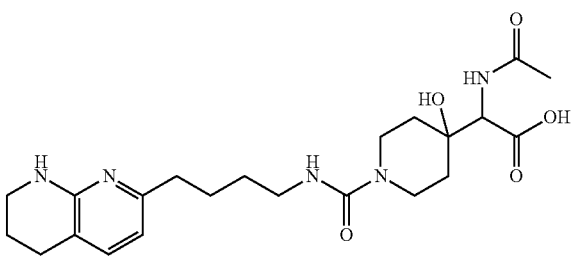 [SMILES: CC(=O)NC(C(=O)O)C1(O)CCN(C(=O)NCCCCc2ccc3c(n2)NCCC3)CC1]

Compound 34 LC/MS A: 100% purity, UV=214 nm, Rt=1.39 min, ESI 448.2 (M+H)$^+$. $^1$H NMR (500 MHz, MeOD) δ 7.44 (d, J=7.3 Hz, 1H), 6.50 (d, J=7.3 Hz, 1H), 4.35 (s, 1H), 3.81 (t, J=14.9 Hz, 2H), 3.53-3.41 (m, 2H), 3.20 (tt, J=16.3, 8.6 Hz, 4H), 2.79 (t, J=6.1 Hz, 2H), 2.73-2.59 (m, 2H), 2.05 (s, 3H), 2.01-1.89 (m, 3H), 1.81-1.63 (m, 3H), 1.62-1.47 (m, 4H).

2-acetamido-2-(4-hydroxy-1-(4-((5,6,7,8-tetrahydro-1,8-naphthyridin-2-yl)methyl) piperidine-1-carbonyl)piperidin-4-yl)acetic Acid (Compound 35)

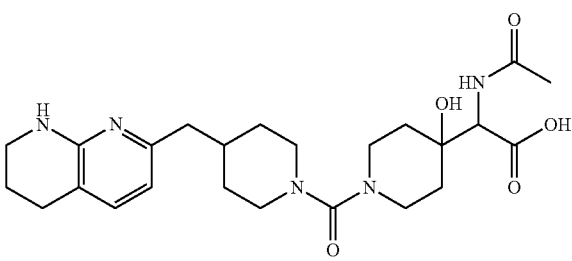 [SMILES: CC(=O)NC(C(=O)O)C1(O)CCN(C(=O)N2CCC(Cc3ccc4c(n3)NCCC4)CC2)CC1]

Compound 35 LC/MS A: 100% purity, UV=214 nm, Rt=1.54 min, ESI 474.3 (M+H)$^+$. $^1$H NMR (500 MHz, Methanol-d$_4$) δ 7.58 (d, J=7.4 Hz, 1H), 6.61 (d, J=7.4 Hz, 1H), 4.28 (s, 1H), 3.66 (d, J=13.1 Hz, 2H), 3.53-3.43 (m, 4H), 3.20-3.11 (m, 2H), 2.87-2.76 (m, 4H), 2.64 (d, J=7.3 Hz, 2H), 2.07 (s, 3H), 1.99-1.82 (m, 3H), 1.74-1.52 (m, 6H), 1.31-1.18 (m, 2H).

2-acetamido-2-(4-hydroxy-1-(4-(5,6,7,8-tetrahydro-1,8-naphthyridin-2-yl) piperidine-1-carbonyl)piperidin-4-yl)acetic Acid (Enantiomeric Compounds 36-P1 and 36-P2)

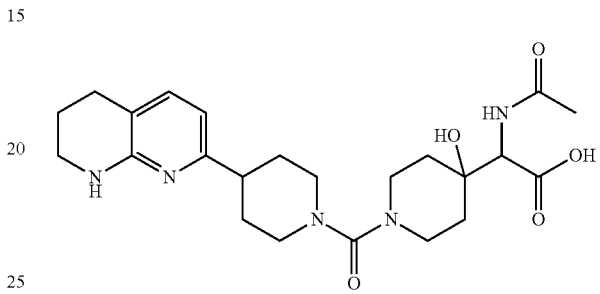

Compound 36-P1 LC/MS A: 100% purity, UV=214 nm, Rt=1.40 min, ESI 460.2 (M+H)$^+$. $^1$H NMR (500 MHz, Methanol-d$_4$) δ 7.48 (d, J=7.4 Hz, 1H), 6.55 (d, J=7.4 Hz, 1H), 4.40 (s, 1H), 3.88-3.77 (m, 2H), 3.60-3.43 (m, 4H), 3.28-3.19 (m, 2H), 3.01-2.91 (m, 2H), 2.88-2.76 (m, 3H), 2.06 (s, 3H), 1.98-1.86 (m, 4H), 1.82-1.54 (m, 6H). Chiral SFC H (20% EtOH): ee 96%, Rt=17.94 min.

Compound 36-P2 LC/MS A: 100% purity, UV=214 nm, Rt=1.53 min, ESI 460.3 (M+H)$^+$. $^1$H NMR (500 MHz, Methanol-d$_4$) δ 7.44 (d, J=7.5 Hz, 1H), 6.53 (d, J=7.4 Hz, 1H), 4.39 (s, 1H), 3.82 (t, J=12.0 Hz, 2H), 3.60-3.50 (m, 2H), 3.47 (t, J=5.6 Hz, 2H), 3.28-3.17 (m, 2H), 3.00-2.90 (m, 2H), 2.85-2.74 (m, 3H), 2.06 (s, 3H), 1.95-1.55 (m, 10H). Chiral SFC H (20% EtOH): ee 100%, Rt=11.55 min.

2-acetamido-2-(4-hydroxy-1-(4-(5,6,7,8-tetrahydro-1,8-naphthyridin-2-yl)butanoyl) piperidin-4-yl)acetic Acid (Compound 37)

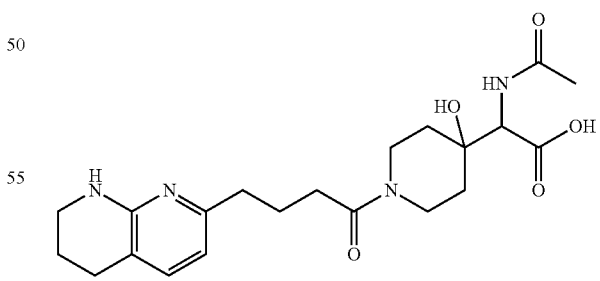

Compound 37 LC/MS A: 100% purity, UV=214 nm, Rt=1.45 min, ESI 419.2 (M+H)$^+$. $^1$H NMR (500 MHz, MeOD) δ 7.51 (d, J=7.3 Hz, 1H), 6.59 (d, J=7.3 Hz, 1H), 4.35 (dd, J=25.2, 6.1 Hz, 2H), 3.83-3.73 (m, 1H), 3.47 (dd, J=26.9, 21.6 Hz, 3H), 3.02 (t, J=12.7 Hz, 1H), 2.81 (t, J=6.0 Hz, 2H), 2.70 (d, J=8.0 Hz, 2H), 2.61-2.43 (m, 2H), 2.02 (t, J=12.8 Hz, 3H), 2.02-1.89 (m, 4H), 1.75-1.56 (m, 4H).

2-acetamido-2-(4-hydroxy-1-(5-(5,6,7,8-tetrahydro-1,8-naphthyridin-2-yl)pentanoyl) piperidin-4-yl) acetic Acid (Enantiomeric Compounds 38-P1 and 38-P2)

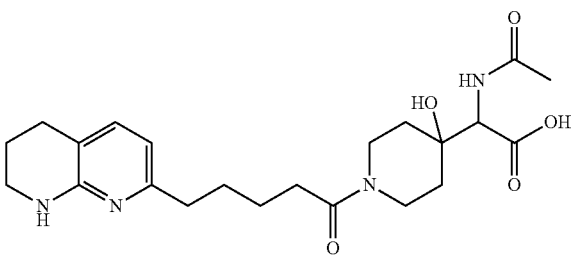 [SMILES: CC(=O)NC(C(=O)O)C1(O)CCN(C(=O)CCCCc2ccc3c(n2)NCCC3)CC1]

Compound 38-P1 LC/MS B: 100% purity, UV=214 nm, Rt=0.68 min, ESI 433 (M+H)+. $^1$H NMR (500 MHz, MeOD) δ 7.65-7.42 (m, 1H), 6.59-6.48 (m, 1H), 4.37 (m, 2H), 3.81 (m, 1H), 3.54-3.41 (m, 3H), 2.96 (m, 1H), 2.79 (m, 2H), 2.71-2.47 (m, 3H), 2.40-2.24 (m, 1H), 2.06 (m, 3H), 1.98-1.85 (m, 2H), 1.79-1.46 (m, 8H). Chiral SFC F (40% MeOH): ee 91%, Rt=3.37 min.

Compound 38-P2 LC/MS B: 100% purity, UV=214 nm, Rt=0.68 min, ESI 433 (M+H)+. $^1$H NMR (500 MHz, MeOD) δ 7.48 (dd, J=7.2, 4.0 Hz, 1H), 6.53 (t, J=7.3 Hz, 1H), 4.37 (t, J=17.4 Hz, 2H), 3.81 (t, J=12.4 Hz, 1H), 3.46 (m, 3H), 3.05-2.87 (m, 1H), 2.83-2.71 (m, 2H), 2.71-2.53 (m, 3H), 2.50-2.27 (m, 1H), 2.06 (d, J=12.0 Hz, 3H), 1.98-1.84 (m, 2H), 1.79-1.48 (m, 8H). Chiral SFC F (40% MeOH): ee 75%, Rt=5.07 min.

2-acetamido-2-(4-hydroxy-1-(4-(5,6,7,8-tetrahydro-1,8-naphthyridin-2-yl)butyl) piperidin-4-yl)acetic Acid (Compound 39)

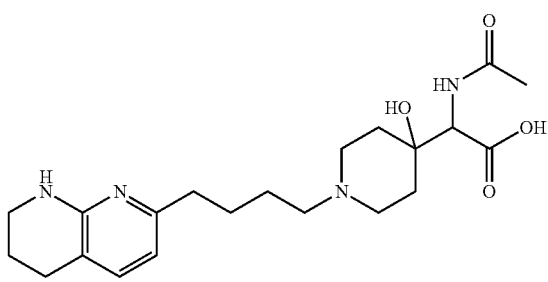 [SMILES: CC(=O)NC(C(=O)O)C1(O)CCN(CCCCc2ccc3c(n2)NCCC3)CC1]

Compound 39 LC/MS C: 100% purity, UV=214 nm, Rt=1.55 min, ESI 405.2 (M+H)+. $^1$H NMR (500 MHz, MeOD) δ 7.15 (d, J=7.3 Hz, 1H), 6.39 (d, J=7.3 Hz, 1H), 4.36 (s, 1H), 3.42-3.36 (m, 2H), 3.16 (s, 2H), 2.93 (d, J=12.1 Hz, 2H), 2.85 (s, 2H), 2.71 (t, J=6.2 Hz, 2H), 2.56 (d, J=5.3 Hz, 2H), 2.04 (s, 3H), 1.96-1.85 (m, 4H), 1.81-1.78 (m, 1H), 1.70-1.68 (m, 5H), 1.32 (s, 1H).

2-(3-hydroxy-1-(4-((5,6,7,8-tetrahydro-1,8-naphthyridin-2-yl)methyl)piperidine-1-carbonyl)azetidin-3-yl)acetic Acid (Compound 40)

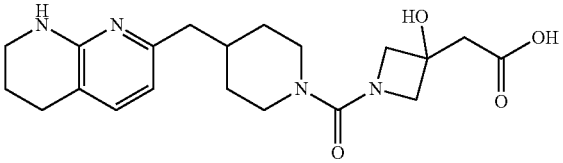 [SMILES: O=C(O)CC1(O)CN(C(=O)N2CCC(Cc3ccc4c(n3)NCCC4)CC2)C1]

Compound 40 LC/MS B: 100% purity, UV=214 nm, Rt=1.07 min, ESI 389.0 (M+H)+. $^1$H NMR (400 MHz, Methanol-$d_4$) δ 7.43-7.32 (m, 1H), 6.47 (d, J=6.9 Hz, 1H), 4.03 (d, J=8.6 Hz, 2H), 3.95-3.81 (m, 4H), 3.48-3.41 (m, 2H), 2.83-2.71 (m, 4H), 2.66 (s, 2H), 2.56 (d, J=7.2 Hz, 2H), 1.98-1.84 (m, 3H), 1.69-1.58 (m, 2H), 1.26-1.12 (m, 2H).

2-(3-hydroxy-1-(4-(5,6,7,8-tetrahydro-1,8-naphthyridin-2-yl)piperidine-1-carbonyl) azetidin-3-yl)acetic Acid (Compound 41)

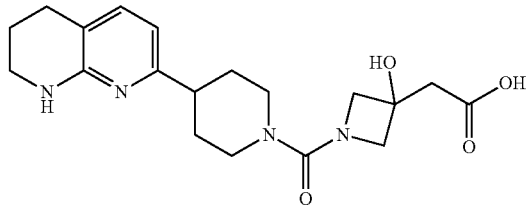 [SMILES: O=C(O)CC1(O)CN(C(=O)N2CCC(c3ccc4c(n3)NCCC4)CC2)C1]

Compound 41 LC/MS B: 100% purity, UV=214 nm, Rt=1.05 min, ESI 375 (M+H)+. $^1$H NMR (500 MHz, MeOD) δ 7.41 (d, J=7.4 Hz, 1H), 6.51 (d, J=7.4 Hz, 1H), 4.10 (d, J=8.8 Hz, 2H), 4.03 (d, J=13.2 Hz, 2H), 3.96 (d, J=8.7 Hz, 2H), 3.45 (dd, J=11.0, 5.6 Hz, 2H), 2.93 (t, J=12.4 Hz, 2H), 2.81 (s, 1H), 2.78 (t, J=6.1 Hz, 2H), 2.70 (s, 2H), 1.92 (dd, J=16.5, 10.7 Hz, 4H), 1.71-1.61 (m, 2H).

2-(3-hydroxy-1-((3-(5,6,7,8-tetrahydro-1,8-naphthyridin-2-yl)propyl) carbamoyl) azetidin-3-yl)acetic Acid (Compound 42)

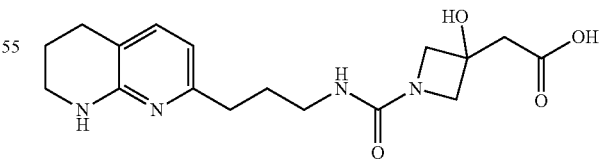

Compound 42 LC/MS B: 100% purity, UV=214 nm, Rt=1.01 min, ESI 349.0 (M+H)+. $^1$H NMR (400 MHz, Methanol-$d_4$) δ 7.48 (d, J=7.3 Hz, 1H), 6.53 (d, J=7.3 Hz, 1H), 4.33 (d, J=8.6 Hz, 2H), 3.81 (d, J=8.6 Hz, 2H), 3.50-3.37 (m, 2H), 3.17 (s, 2H), 2.85-2.64 (m, 4H), 2.60 (s, 2H), 2.00-1.72 (m, 4H).

2-(3-hydroxy-1-((4-(5,6,7,8-tetrahydro-1,8-naphthyridin-2-yl)butyl)carbamoyl) azetidin-3-yl)acetic Acid (Compound 43)

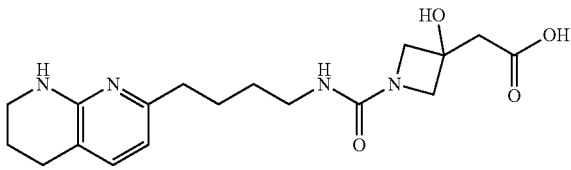 [SMILES: O=C(O)CC1(O)CN(C(=O)NCCCCc2ccc3c(n2)NCCC3)C1]

Compound 43 LC/MS A: 100% purity, UV=214 nm, Rt=1.47 min, ESI 363.3 (M+H)⁺. ¹H NMR (500 MHz, Methanol-$d_4$) δ 7.41 (d, J=7.3 Hz, 1H), 6.46 (d, J=7.4 Hz, 1H), 4.30 (d, J=8.5 Hz, 2H), 3.76 (d, J=8.5 Hz, 2H), 3.46-3.40 (m, 2H), 3.29-3.21 (m, 2H), 2.78 (t, J=6.3 Hz, 2H), 2.67-2.62 (m, 2H), 2.59 (s, 2H), 1.96-1.89 (m, 2H), 1.79-1.69 (m, 2H), 1.64-1.55 (m, 2H).

2-acetamido-2-(3-hydroxy-1-((3-(5,6,7,8-tetrahydro-1,8-naphthyridin-2-yl)propyl) carbamoyl)azetidin-3-yl)acetic Acid (Compound 44)

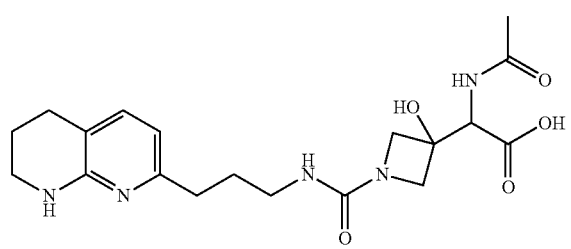 [SMILES: CC(=O)NC(C(=O)O)C1(O)CN(C(=O)NCCCc2ccc3c(n2)NCCC3)C1]

Compound 44 LC/MS A: 100% purity, UV=214 nm, Rt=1.34 min, ESI 406.2 (M+H)⁺. 1H NMR (400 MHz, MeOD) δ 7.43 (d, J=7.3 Hz, 1H), 6.53 (d, J=7.3 Hz, 1H), 4.52-4.46 (m, 1H), 4.43-4.09 (m, 2H), 3.78 (dd, J=9.1, 3.3 Hz, 2H), 3.43 (dd, J=27.2, 21.6 Hz, 2H), 3.22-2.97 (m, 2H), 2.85-2.58 (m, 4H), 2.12-1.95 (m, 3H), 1.96-1.60 (m, 4H).

2-acetamido-2-(3-hydroxy-1-((4-(5,6,7,8-tetrahydro-1,8-naphthyridin-2-yl)butyl) carbamoyl)azetidin-3-yl)acetic Acid (Compound 45)

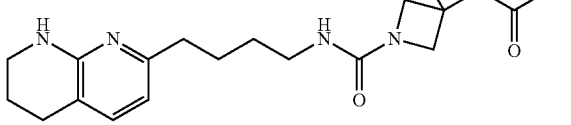

Compound 45 LC/MS A: 100% purity, UV=214 nm, Rt=1.47 min, ESI 420.3 (M+H)⁺. 1H NMR (500 MHz, MeOD) δ 7.53 (d, J=7.3 Hz, 1H), 6.57 (d, J=7.3 Hz, 1H), 4.50 (s, 1H), 4.33 (d, J=9.1 Hz, 1H), 4.25 (d, J=9.3 Hz, 1H), 3.82-3.71 (m, 2H), 3.55-3.40 (m, 2H), 3.19 (s, 2H), 2.81 (t, J=6.2 Hz, 2H), 2.74-2.63 (m, 2H), 2.06 (s, 3H), 1.99-1.90 (m, 2H), 1.85-1.66 (m, 2H), 1.66-1.37 (m, 2H).

2-acetamido-2-(3-hydroxy-1-(5-(5,6,7,8-tetrahydro-1,8-naphthyridin-2-yl)pentanoyl) azetidin-3-yl)acetic Acid (Compound 46)

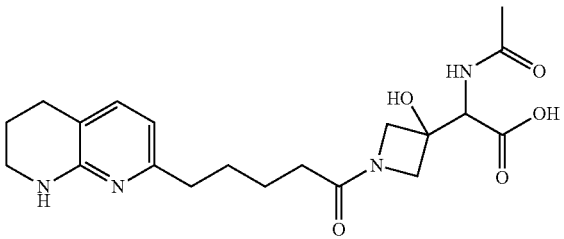 [SMILES: CC(=O)NC(C(=O)O)C1(O)CN(C(=O)CCCCc2ccc3c(n2)NCCC3)C1]

Compound 46 LC/MS A: 100% purity, UV=254 nm, Rt=1.46 min, ESI 405 (M+H)⁺. ¹H NMR (500 MHz, MeOD) δ 7.35 (d, J=7.3 Hz, 1H), 6.41 (dd, J=7.3, 1H), 4.62 (dd, J=22.5, 9.5 Hz, 1H), 4.44 (d, J=14.5 Hz, 1H), 4.16 (dd, J=35.1, 10.8 Hz, 1H), 3.92 (dd, J=9.0, 6.2 Hz, 1H), 3.67 (dd, J=10.5, 5.9 Hz, 1H), 3.36 (t, J=5.6 Hz, 2H), 2.67 (t, J=6.1 Hz, 2H), 2.63-2.46 (m, 2H), 2.22 (dd, J=14.7, 6.6 Hz, 1H), 2.08-1.98 (m, 1H), 1.93 (d, J=7.5 Hz, 3H), 1.82 (dd, J=11.2, 5.8 Hz, 2H), 1.71-1.52 (m, 4H).

2-acetamido-2-(3-hydroxy-1-(5-(5,6,7,8-tetrahydro-1,8-naphthyridin-2-yl)pentyl) azetidin-3-yl)acetic Acid (Compound 47)

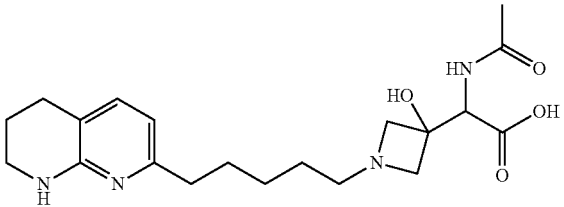 [SMILES: CC(=O)NC(C(=O)O)C1(O)CN(CCCCCc2ccc3c(n2)NCCC3)C1]

Compound 47 LC/MS A: 100% purity, UV=214 nm, Rt=1.02 min, ESI 391 (M+H)⁺. ¹H NMR (500 MHz, MeOD) δ 8.49 (s, 1H), 7.48 (d, J=7.3 Hz, 1H), 6.56 (d, J=7.3 Hz, 1H), 4.61 (s, 1H), 3.59-3.50 (m, 3H), 3.50-3.46 (m, 2H), 3.42 (m, 1H), 3.28-3.17 (m, 1H), 2.80 (t, J=6.2 Hz, 2H), 2.67 (t, J=7.5 Hz, 2H), 2.07 (d, J=10.2 Hz, 3H), 1.98-1.90 (m, 2H), 1.77-1.67 (m, 2H), 1.67-1.57 (m, 2H), 1.43-1.34 (m, 2H).

2-(5-cyclopropyl-1,3,4-oxadiazole-2-carboxamido)-2-(4-hydroxy-1-((3-(5,6,7,8-tetrahydro-1,8-naphthyridin-2-yl)propyl)carbamoyl)piperidin-4-yl)acetic Acid (Compound 48)

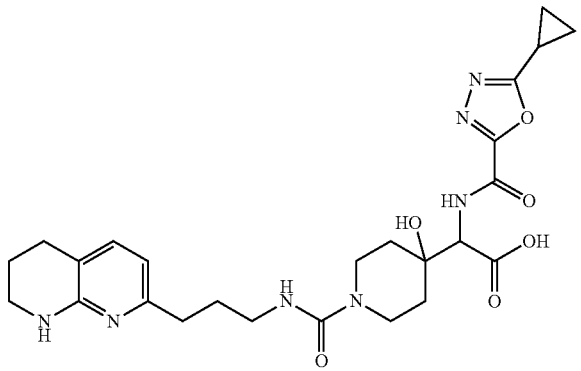 [SMILES: O=C(NC(C(=O)O)C1(O)CCN(C(=O)NCCCc2ccc3c(n2)NCCC3)CC1)c1nnc(C2CC2)o1]

Compound 48 LC/MS A: 100% purity, UV=214 nm, Rt=1.42 min, ESI 528 (M+H)⁺. ¹H NMR (500 MHz, MeOD) δ 7.52 (d, J=7.5 Hz, 1H), 6.59 (d, J=7.4 Hz, 1H), 4.60 (brs, 1H), 4.44 (s, 1H), 3.87 (m, 1H), 3.79 (m, 1H), 3.54-3.41 (m, 2H), 3.28-3.05 (m, 3H), 2.81 (t, J=6.0 Hz, 1H), 2.70 (m, 2H), 2.46-2.35 (m, 1H), 2.35-2.25 (m, 1H), 1.99-1.91 (m, 2H), 1.91-1.76 (m, 3H), 1.68-1.52 (m, 2H), 1.41-1.16 (m, 6H).

2-(4-hydroxy-1-((3-(5,6,7,8-tetrahydro-1,8-naphthyridin-2-yl)propyl) carbamoyl)piperidin-4-yl)-2-(3-(5-methyl-1H-pyrazol-1-yl)propanamido)acetic Acid (Compound 49)

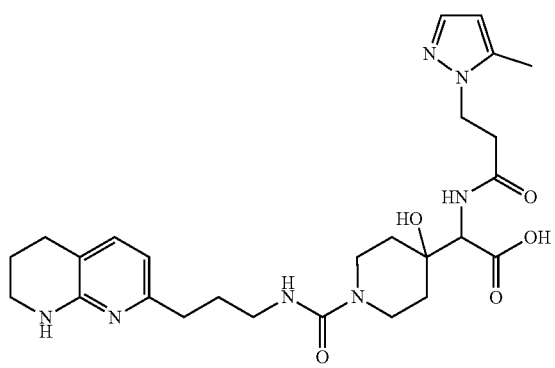 [SMILES: Cc1ccnn1CCC(=O)NC(C(=O)O)C1(O)CCN(C(=O)NCCCc2ccc3c(n2)NCCC3)CC1]

Compound 49 LC/MS A: 100% purity, UV=254 nm, Rt=1.41 min, ESI 528 (M+H)⁺. ¹H NMR (500 MHz, MeOD) δ 7.27 (d, J=7.3 Hz, 1H), 7.22 (d, J=1.6 Hz, 1H), 6.40 (d, J=7.3 Hz, 1H), 5.90 (s, 1H), 4.28 (ddd, J=14.6, 8.2, 6.7 Hz, 1H), 4.22-4.14 (m, 2H), 3.63 (d, J=12.6 Hz, 2H), 3.36-3.29 (m, 2H), 3.15 (dd, J=13.4, 6.7 Hz, 1H), 3.09 (dd, J=13.4, 6.6 Hz, 1H), 3.04-2.94 (m, 2H), 2.82-2.74 (m, 1H), 2.68-2.61 (m, 3H), 2.57-2.48 (m, 2H), 2.21 (s, 3H), 1.83-1.77 (m, 2H), 1.76-1.62 (m, 3H), 1.39 (dt, J=21.5, 10.3 Hz, 2H), 1.28 (d, J=13.4 Hz, 1H).

2-(4-hydroxy-1-((3-(5,6,7,8-tetrahydro-1,8-naphthyridin-2-yl)propyl)carbamoyl) piperidin-4-yl)-2-(2-(methylsulfonamido)acetamido)acetic Acid (Compound 50)

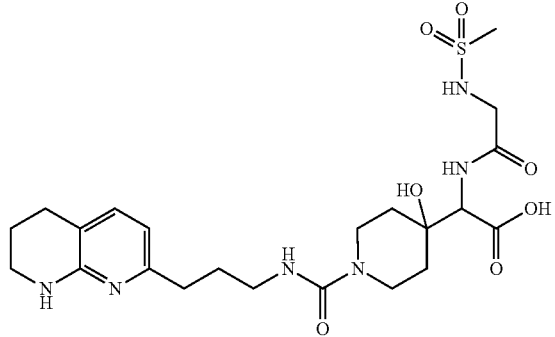 [SMILES: CS(=O)(=O)NCC(=O)NC(C(=O)O)C1(O)CCN(C(=O)NCCCc2ccc3c(n2)NCCC3)CC1]

Compound 50 LC/MS A: 100% purity, UV=254 nm, Rt=1.36 min, ESI 527 (M+H)⁺. ¹H NMR (500 MHz, MeOD) δ 7.03 (d, J=7.3 Hz, 1H), 6.28 (d, J=7.3 Hz, 1H), 4.22 (s, 1H), 3.69 (t, J=14.2 Hz, 4H), 3.30-3.24 (m, 2H), 3.06 (ddd, J=29.3, 16.5, 8.1 Hz, 4H), 2.88 (s, 3H), 2.59 (t, J=6.4 Hz, 2H), 2.45-2.38 (m, 2H), 1.80-1.74 (m, 2H), 1.73-1.67 (m, 2H), 1.52 (dd, J=21.3, 8.4 Hz, 3H), 1.39 (d, J=11.0 Hz, 1H).

2-(3-acetamido-3-methylbutanamido)-2-(4-hydroxy-1-((3-(5,6,7,8-tetrahydro-1,8-naphthyridin-2-yl)propyl)carbamoyl)piperidin-4-yl)acetic Acid (Compound 51)

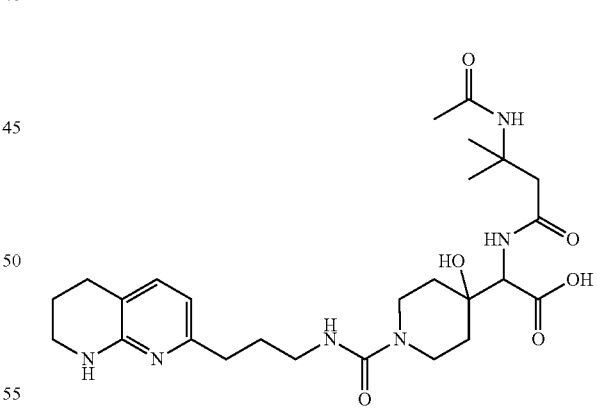

Compound 51 LC/MS A: 100% purity, UV=214 nm, Rt=1.53 min, ESI 533.3 (M+H)⁺. 1H NMR (500 MHz, MeOD) δ 7.49 (d, J=7.4 Hz, 1H), 6.57 (d, J=7.3 Hz, 1H), 4.32 (s, 1H), 3.95-3.71 (m, 2H), 3.53-3.40 (m, 2H), 3.19 (m, 4H), 2.87-2.48 (m, 6H), 2.18-1.88 (m, 6H), 1.80 (m, 3H), 1.55 (m, 2H), 1.42 (d, J=8.5 Hz, 6H).

101

2-(6-ethylpicolinamido)-2-(4-hydroxy-1-((3-(5,6,7,8-tetrahydro-1,8-naphthyridin-2-yl)propyl)carbamoyl)piperidin-4-yl)acetic Acid (Compound 52)

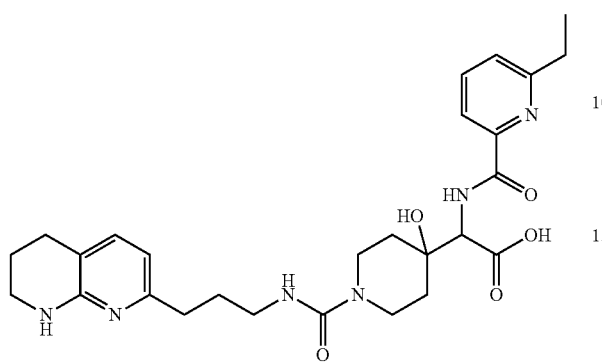

Compound 52 LC/MS B: 100% purity, UV=214 nm, Rt=1.21 min, ESI 525.2 (M+H)$^+$. $^1$H NMR (500 MHz, MeOD) δ 7.93 (d, J=7.6 Hz, 1H), 7.87 (t, J=7.7 Hz, 1H), 7.49 (d, J=7.2 Hz, 1H), 7.45 (d, J=7.6 Hz, 1H), 6.55 (d, J=7.3 Hz, 1H), 4.49 (s, 1H), 3.83 (t, J=14.7 Hz, 2H), 3.47 (t, J=5.5 Hz, 2H), 3.23 (tdd, J=24.2, 15.8, 9.2 Hz, 4H), 2.89 (q, J=7.6 Hz, 2H), 2.79 (t, J=5.9 Hz, 2H), 2.72-2.63 (m, 2H), 2.05 (t, J=10.7 Hz, 1H), 1.96-1.81 (m, 5H), 1.72 (d, J=13.5 Hz, 1H), 1.61 (d, J=12.4 Hz, 1H), 1.34 (q, J=7.9 Hz, 4H).

2-(4-hydroxy-1-((3-(5,6,7,8-tetrahydro-1,8-naphthyridin-2-yl)propyl)carbamoyl) piperidin-4-yl)-2-(3-(N-methylacetamido)propanamido)acetic Acid (Compound 53)

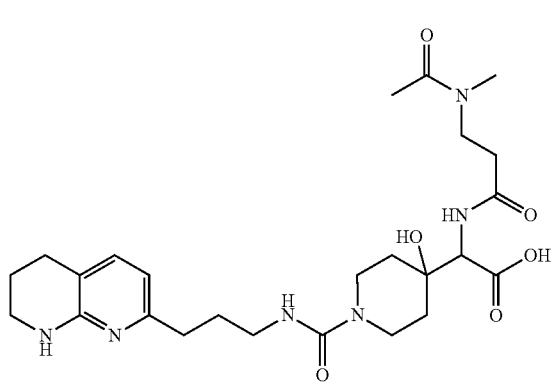 [SMILES: CC(=O)N(C)CCC(=O)NC(C(=O)O)C1(O)CCN(C(=O)NCCCc2ccc3c(n2)NCCC3)CC1]

Compound 53 LC/MS A: 100% purity, UV=214 nm, Rt=1.35 min, ESI 519 (M+H)$^+$. $^1$H NMR (500 MHz, MeOD) δ 7.25 (d, J=7.1 Hz, 1H), 6.45 (d, J=7.3 Hz, 1H), 4.36 (d, J=9.3 Hz, 1H), 3.68 (m, 4H), 3.44-3.38 (m, 2H), 3.29-3.09 (m, 4H), 2.90 (m, 3H), 2.73 (t, J=6.2 Hz, 2H), 2.68-2.48 (m, 3H), 2.11 (m, 1H), 1.96-1.86 (m, 3H), 1.86-1.78 (m, 2H), 1.74-1.56 (m, 2H), 1.52 (t, J=18.6 Hz, 4H).

102

2-(4-hydroxy-1-((3-(5,6,7,8-tetrahydro-1,8-naphthyridin-2-yl)propyl)carbamoyl) piperidin-4-yl)-2-(4-oxo-4-(propylamino)butanamido)acetic Acid (Compound 54)

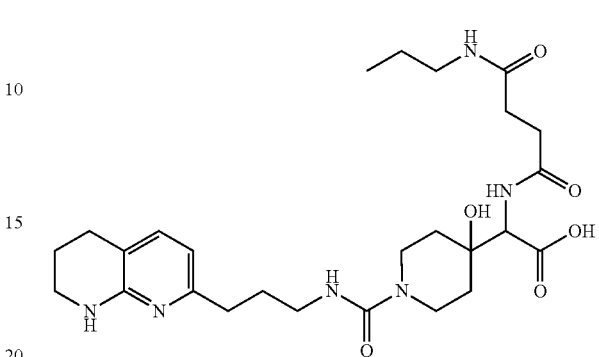

Compound 54 LC/MS A: 100% purity, UV=214 nm, Rt=1.40 min, ESI 533.3 (M+H)$^+$. $^1$H NMR (500 MHz, MeOD) δ 7.47 (d, J=7.4 Hz, 1H), 6.56 (d, J=7.4 Hz, 1H), 4.36 (s, 1H), 3.80 (t, J=15.2 Hz, 2H), 3.50-3.44 (m, 2H), 3.32-3.27 (m, 1H), 3.23-3.09 (m, 5H), 2.79 (t, J=6.1 Hz, 2H), 2.74-2.45 (m, 6H), 2.07 (t, J=11.5 Hz, 1H), 1.99-1.71 (m, 5H), 1.63-1.47 (m, 4H), 0.93 (t, J=7.4 Hz, 3H).

2-(2-(cyclopropanecarboxamido)acetamido)-2-(4-hydroxy-1-((3-(5,6,7,8-tetrahydro-1,8-naphthyridin-2-1)propyl)carbamoyl)piperidin-4-yl)acetic Acid (Compound 55)

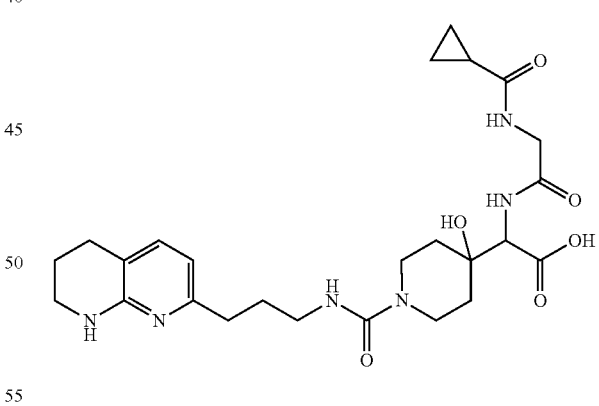

Compound 55 LC/MS B: 100% purity, UV=214 nm, Rt=1.08 min, ESI 517.2 (M+H)$^+$. $^1$H NMR (500 MHz, MeOD) δ 7.47 (d, J=7.3 Hz, 1H), 6.56 (d, J=7.4 Hz, 1H), 4.34 (s, 1H), 3.95 (s, 2H), 3.80 (t, J=12.7 Hz, 2H), 3.50-3.42 (m, 2H), 3.29 (t, J=6.3 Hz, 1H), 3.24-3.08 (m, 3H), 2.79 (t, J=6.1 Hz, 2H), 2.77-2.58 (m, 2H), 2.08-1.63 (m, 7H), 1.54 (dd, J=27.8, 12.7 Hz, 2H), 0.93-0.85 (m, 2H), 0.81 (td, J=7.2, 3.2 Hz, 2H).

2-(4-hydroxy-1-((3-(5,6,7,8-tetrahydro-1,8-naphthyridin-2-yl)propyl)carbamoyl) piperidin-4-yl)-2-(3-(5-methyl-1H-tetrazol-1-yl)propanamido)acetic Acid (Compound 56)

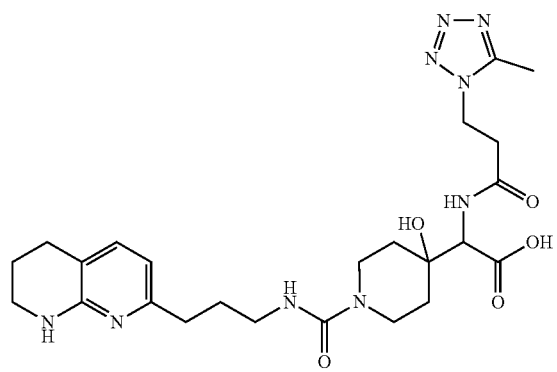 [SMILES: Cc1nnnn1CCC(=O)NC(C(=O)O)C1(O)CCN(C(=O)NCCCc2ccc3c(n2)NCCC3)CC1]

Compound 56 LC/MS A: 100% purity, UV=214 nm, Rt=1.47 min, ESI 530.2 (M+H)$^+$. $^1$H NMR (500 MHz, MeOD) δ 7.50 (d, J=7.0 Hz, 1H), 6.57 (d, J=7.3 Hz, 1H), 4.70-4.55 (m, 2H), 4.32 (s, 1H), 3.77 (d, J=13.0 Hz, 2H), 3.51-3.45 (m, 2H), 3.30-2.95 (m, 6H), 2.80 (t, J=6.1 Hz, 2H), 2.70 (tt, J=15.1, 7.5 Hz, 2H), 2.62 (s, 3H), 2.04-1.91 (m, 3H), 1.85 (dt, J=13.1, 9.7 Hz, 2H), 1.57 (t, J=15.6 Hz, 1H), 1.44 (dd, J=29.2, 13.4 Hz, 2H).

Example 12: Fluorescence Polarization Assays of Compounds for αvβ6 Binding

Fluorescence Polarization (FP) assays were used to measure compound activity through binding competition with the fluorescein-labeled peptide GRGDLGRL. In the assay, 10 nM of integrin αvβ6 was incubated with the test compound in 2 mM manganese chloride, 0.1 mM calcium chloride, 20 mM HEPES buffer at pH 7.3, 150 mM sodium chloride, 0.01% Triton X-100, 2% DMSO, and 3 nM of the fluorescein-labeled peptide. The assays were run in 384-well plates. For both assay versions, the integrin protein was pre-incubated with the test compounds for 15 minutes at 22° C. before the fluorescein-labeled peptide was added. After the fluorescein-labeled peptide was added, the assay was incubated at 22° C. for 1 hour and fluorescence polarization was measured. IC$_{50}$ values were determined by nonlinear regression, 4-parameter curve fitting (FIG. 1).

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound represented by formula (I):

A-B-C         (I)

wherein:

A is

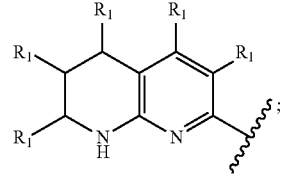

B is -alkylene-N(R)C(O)—, -alkylene-(heterocyclyl)-C(O)—, -aryl-alkylene-N(R)C(O)—, -aryl-N(R)C(O)—, -heterocyclyl-alkylene-N(R)C(O)—, or -heterocyclyl-C(O)—;

C is

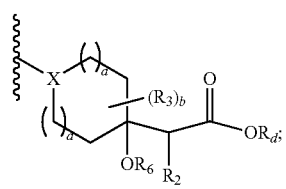

R is independently H, alkyl, or aryl;

$R_1$ is independently H, alkyl, halide, alkoxy, $CF_3$, OH, $NO_2$, —N(H)R, or $NH_2$;

$R_2$ is H, alkyl, substituted or unsubstituted aryl, substituted or unsubstituted heteroaryl, cycloalkyl, -alkylene-alkoxy, alkoxy, OH, -alkylene-aryl, heterocycloalkyl, —N(R)C(O)$R_4$, —N(R)SO$_2$R$_4$-, —N(R)-aryl, or —N(R)-heteroaryl;

$R_3$ is independently alkyl, halide, alkoxy, $CF_3$, OH, $NO_2$, or $NH_2$;

$R_4$ is alkyl, cycloalkyl, heterocycloalkyl, aryl, heteroaryl, -alkylene-heterocyclyl, -alkylene-N(R)C(O)R$_5$, or -alkylene-N(R)—SO$_2$Me;

$R_5$ is alkyl, or cycloalkyl;

$R_6$ is H, or alkyl;

X is N;

$R_d$ is H, or ($C_1$-$C_6$)alkyl;

a is independently 0, or 1; and b is 0, 1, 2, 3, or 4;

or a pharmaceutically acceptable salt thereof.

2. The compound of claim 1, wherein R is H or Me.

3. The compound of claim 1, wherein at least one instance of $R_1$ is alkyl, halide, alkoxy, $CF_3$, OH, —N(H)R, or $NH_2$.

4. The compound of claim 3, wherein $R_1$ is alkyl, or halide.

5. The compound of claim 1, wherein all instances of $R_1$ are H.

6. The compound of claim 1, wherein B is —($C_1$-$C_6$) alkylene-N(R)—C(O)—.

7. The compound of claim 6, wherein B is

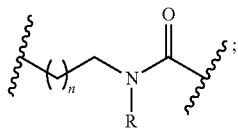

R is H, Me or Ph; and n is 1, 2, or 3.

8. The compound of claim 1, wherein at least one instance of a is 0.

9. The compound of claim 1, wherein at least one instance of a is 1.

10. The compound of claim 1, wherein b is 0.

11. The compound of claim 1, wherein b is 1, or 2.

12. The compound of claim 1, wherein $R_3$ is independently alkyl, halide, alkoxy, or $NH_2$.

13. The compound of claim 1, wherein $R_6$ is H.

14. The compound of claim 1, wherein $R_6$ is Me.

15. The compound of claim 1, wherein C is selected from the group consisting of:

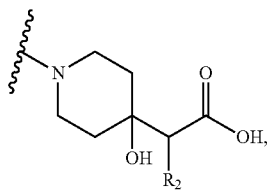

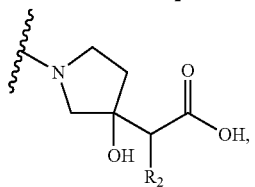

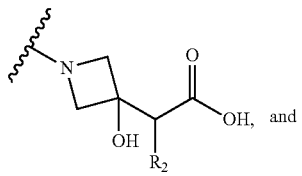

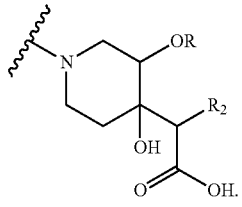

16. The compound of claim 1, wherein $R_2$ is H, alkyl, aryl, heteroaryl, hydroxyl, or alkoxy.

17. The compound of claim 16, wherein $R_2$ is substituted or unsubstituted phenyl.

18. The compound of claim 1, wherein $R_2$ is $N(H)C(O)R_4$, $-N(R)SO_2R_4-$, $-N(H)$-aryl, or $-N(H)$-heteroaryl.

19. The compound of claim 18, wherein $R_2$ is $-N(H)$-2-pyridinyl, or $-N(H)$-2,4-pyrimidinyl.

20. The compound of claim 18, wherein $R_2$ is $-N(H)C(O)Me$.

21. The compound of claim 18, wherein $R_4$ is Me,

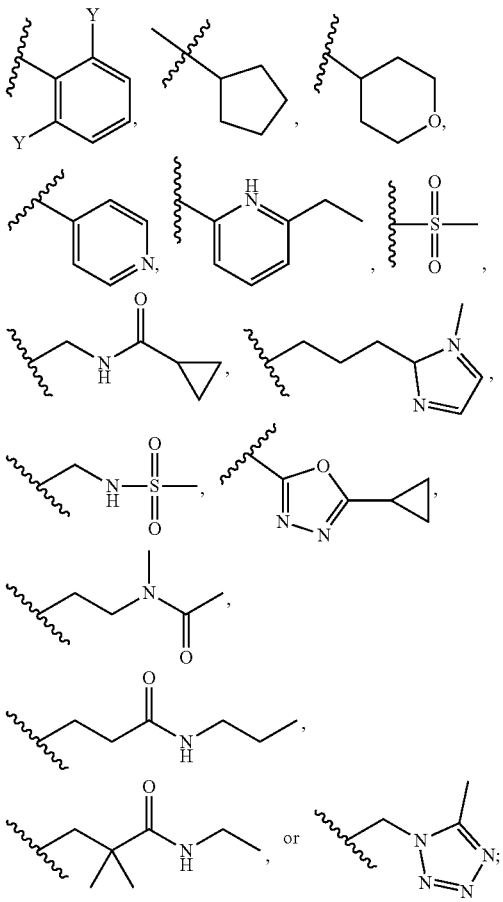

and

Y is H, F, or Cl.

22. A pharmaceutical composition, comprising a compound of claim 1; and a pharmaceutically acceptable excipient.

23. The compound of claim 1, wherein the compound is selected from the group consisting of:

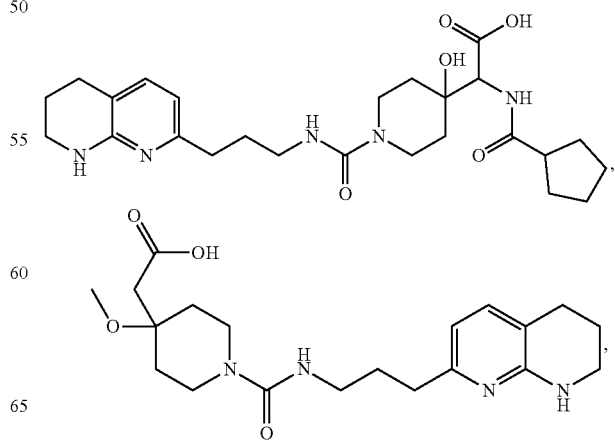

107
-continued
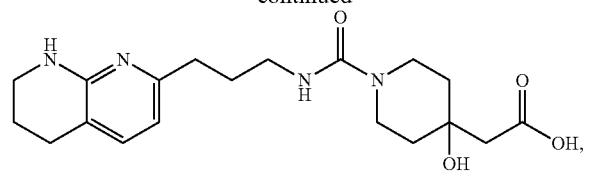
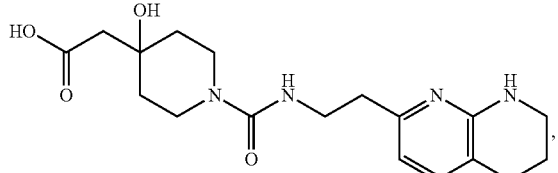
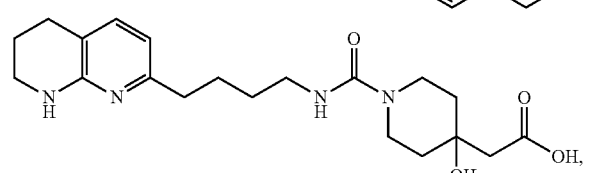
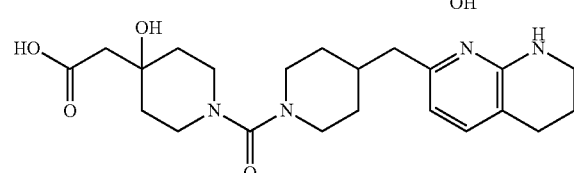
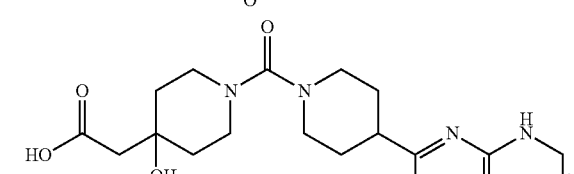
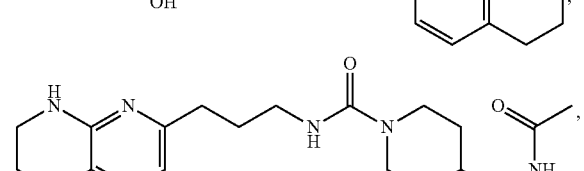
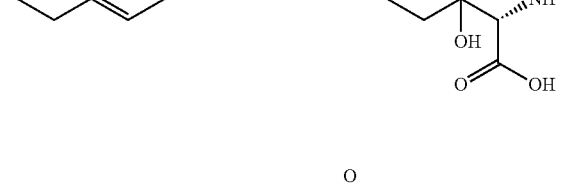
108
-continued
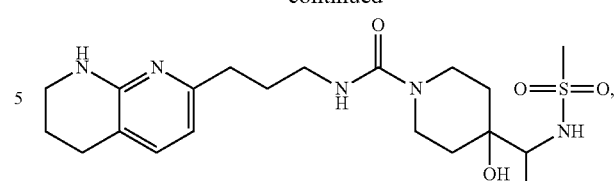
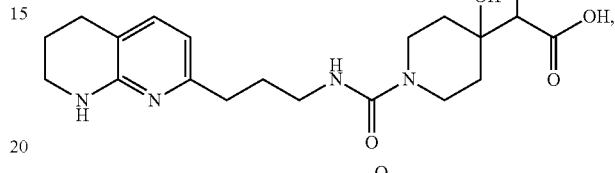
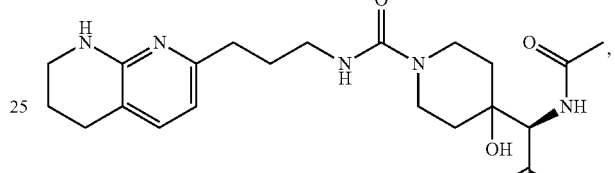
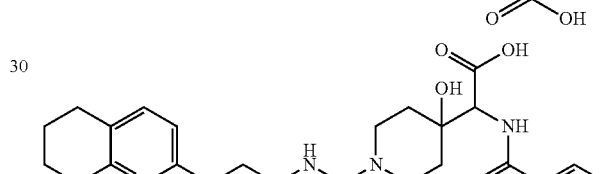
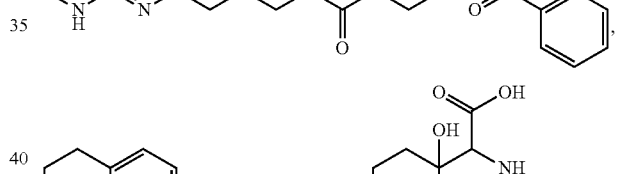
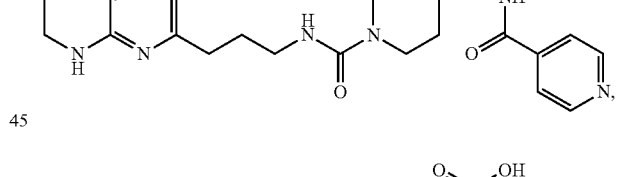
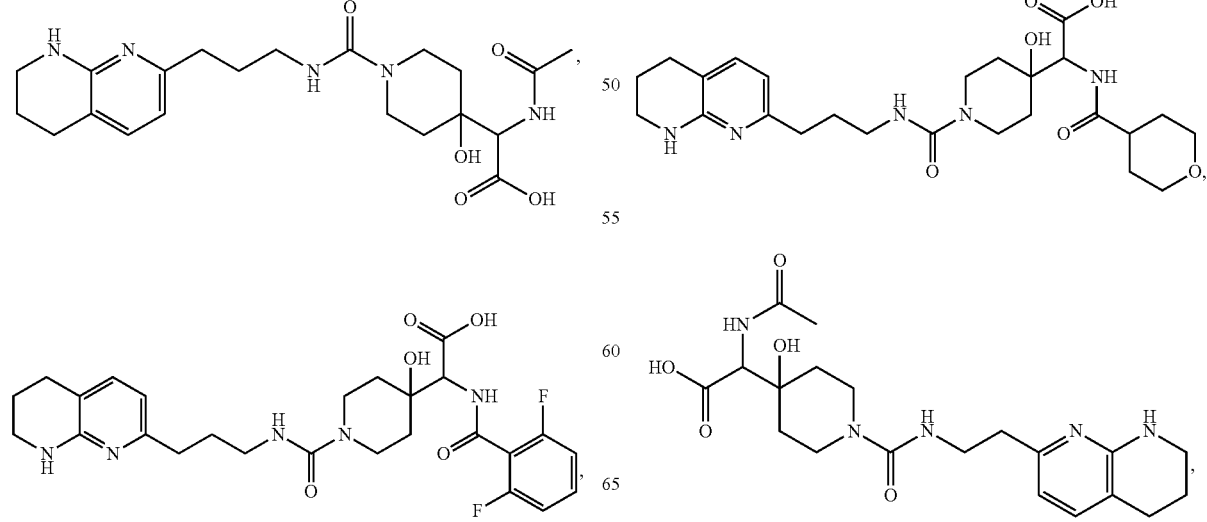

109
-continued
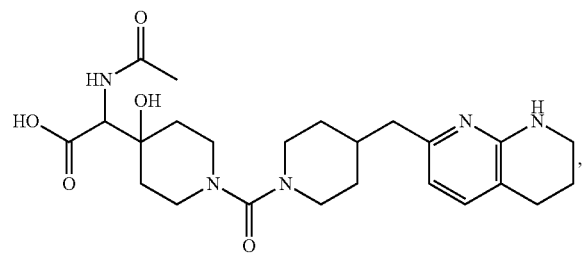
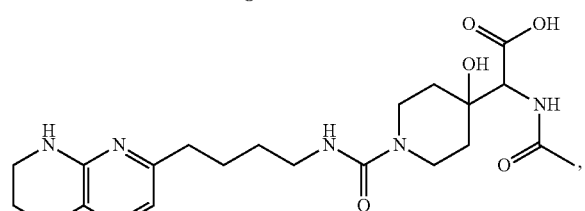
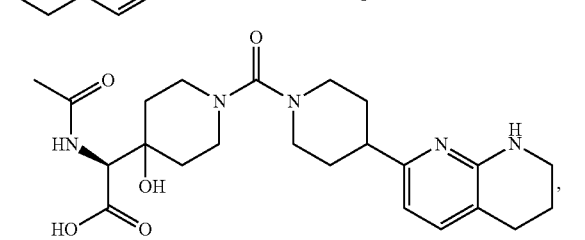
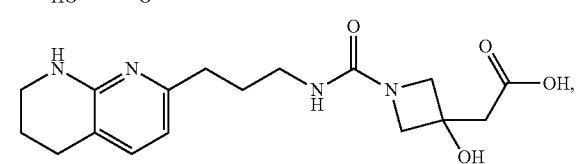
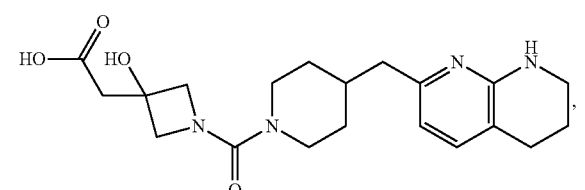
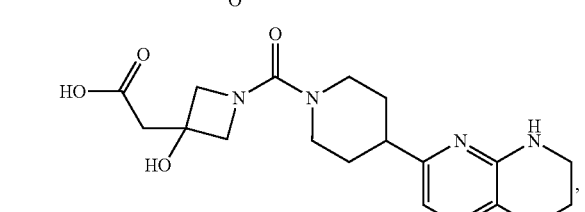
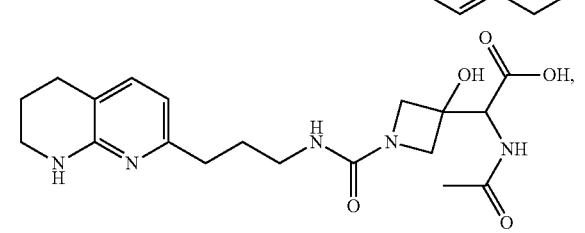
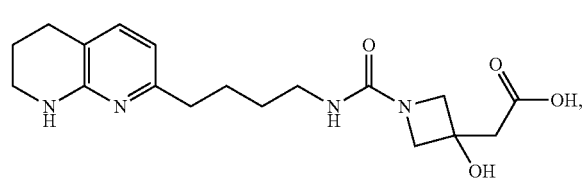
110
-continued
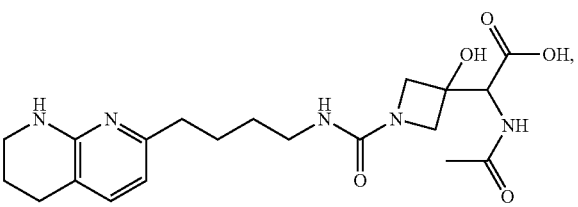
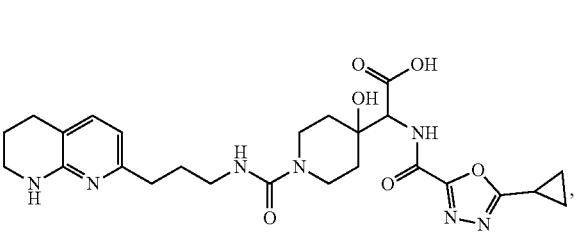
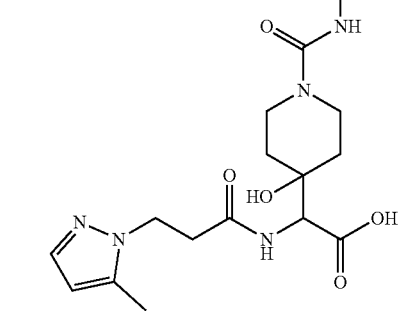
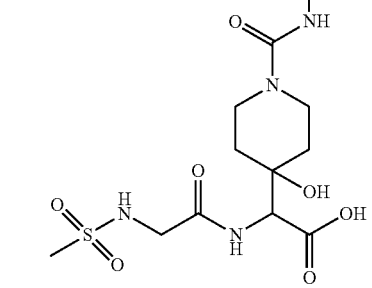

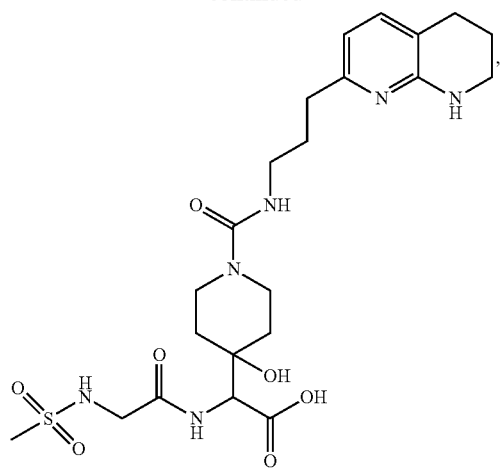
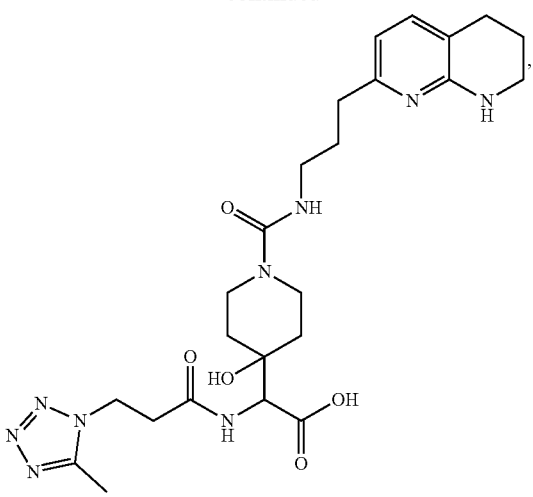
24. The compound of claim 1, wherein the compound is selected from the group consisting of:
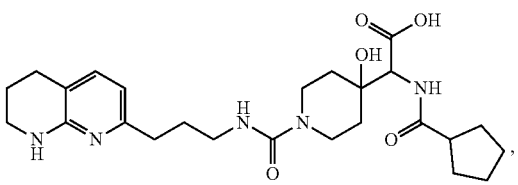

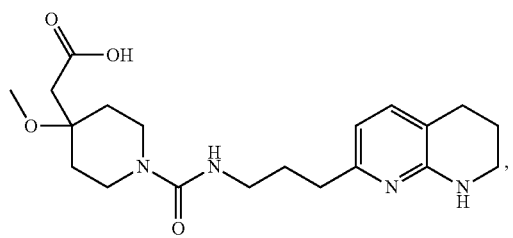
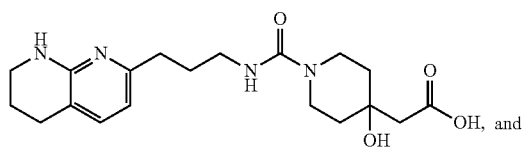
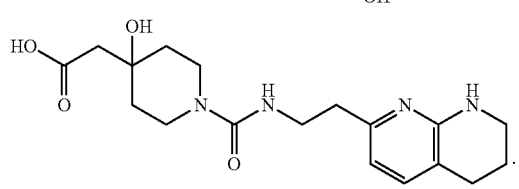
25. The compound of claim 1, wherein the compound is selected from the group consisting of:
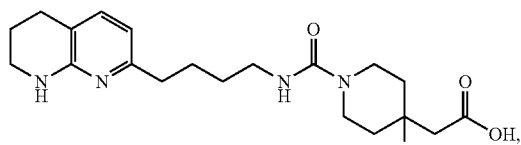
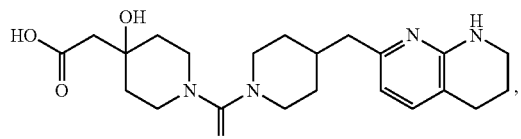
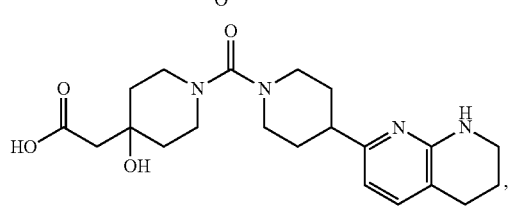
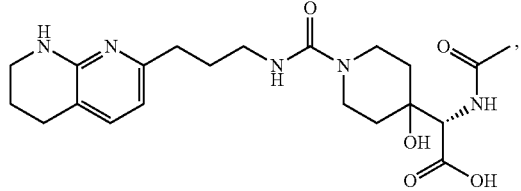
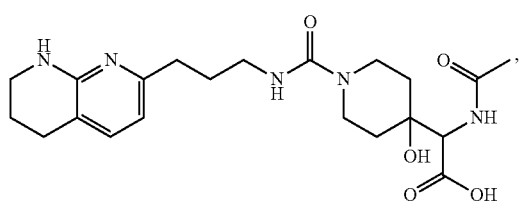
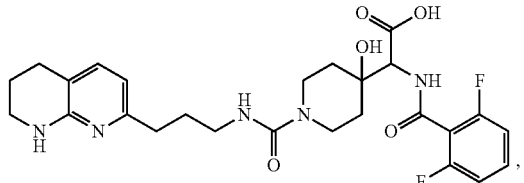
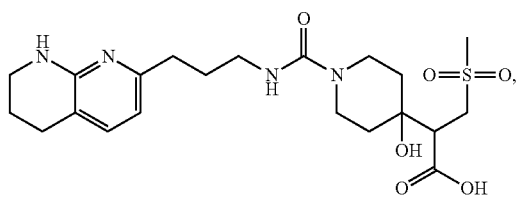
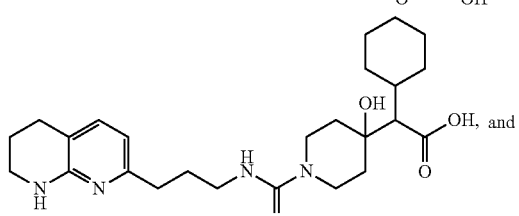
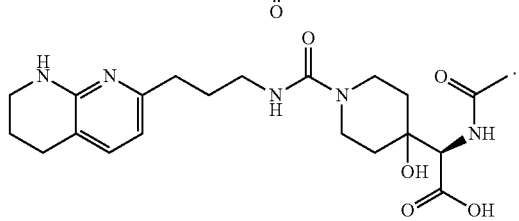
26. The compound of claim 1, wherein the compound is selected from the group consisting of:
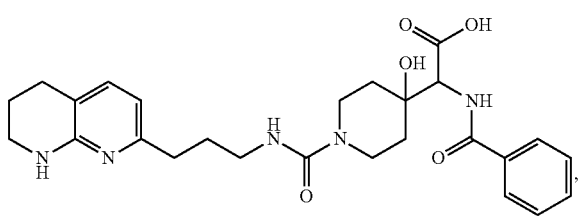
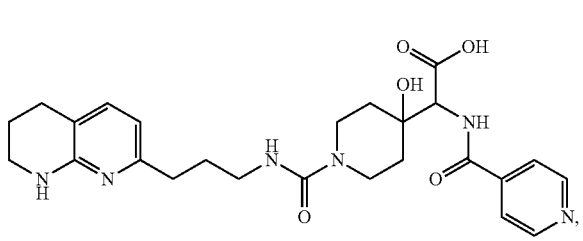
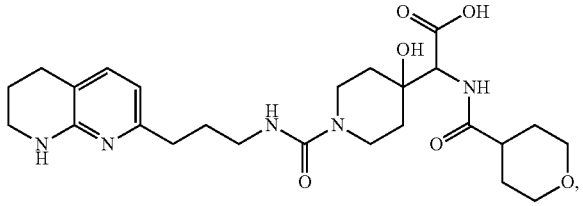

-continued
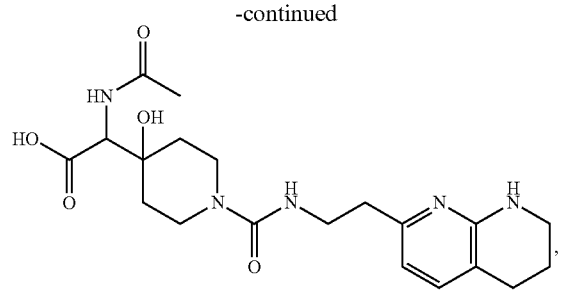
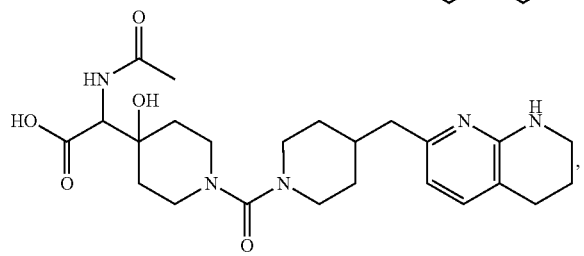
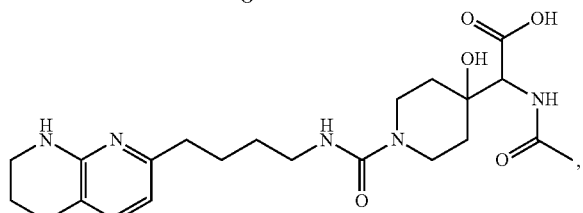
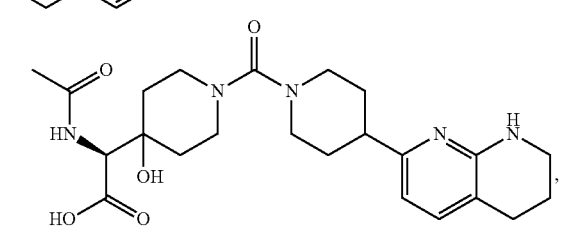
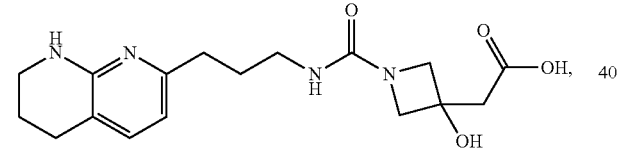
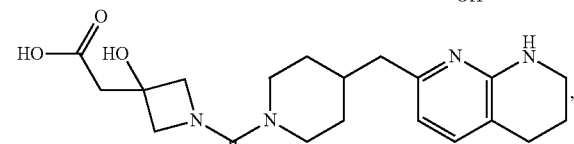
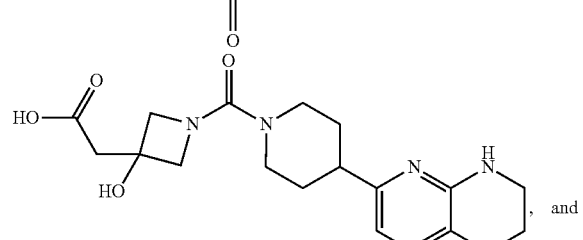
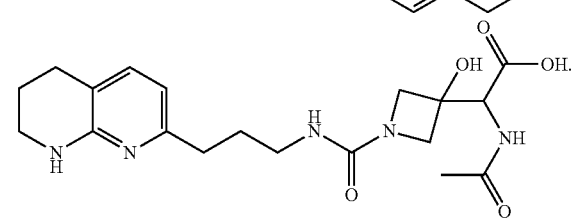
27. The compound of claim 1, wherein the compound is selected from the group consisting of:
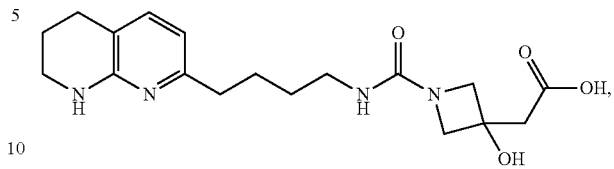
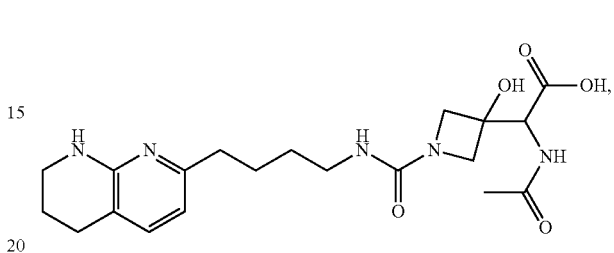
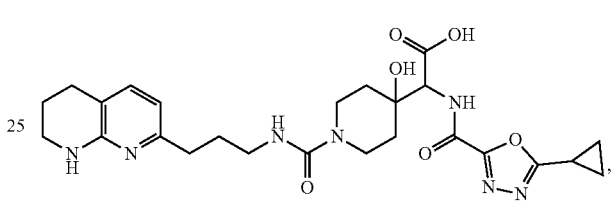
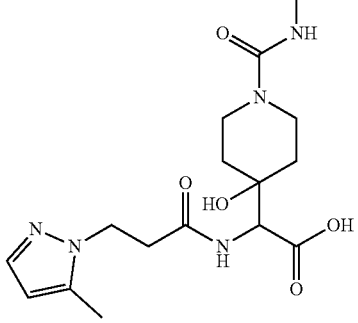
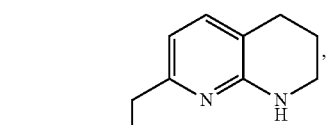
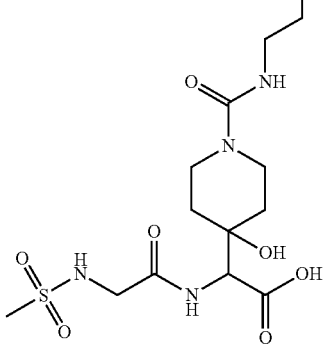

117
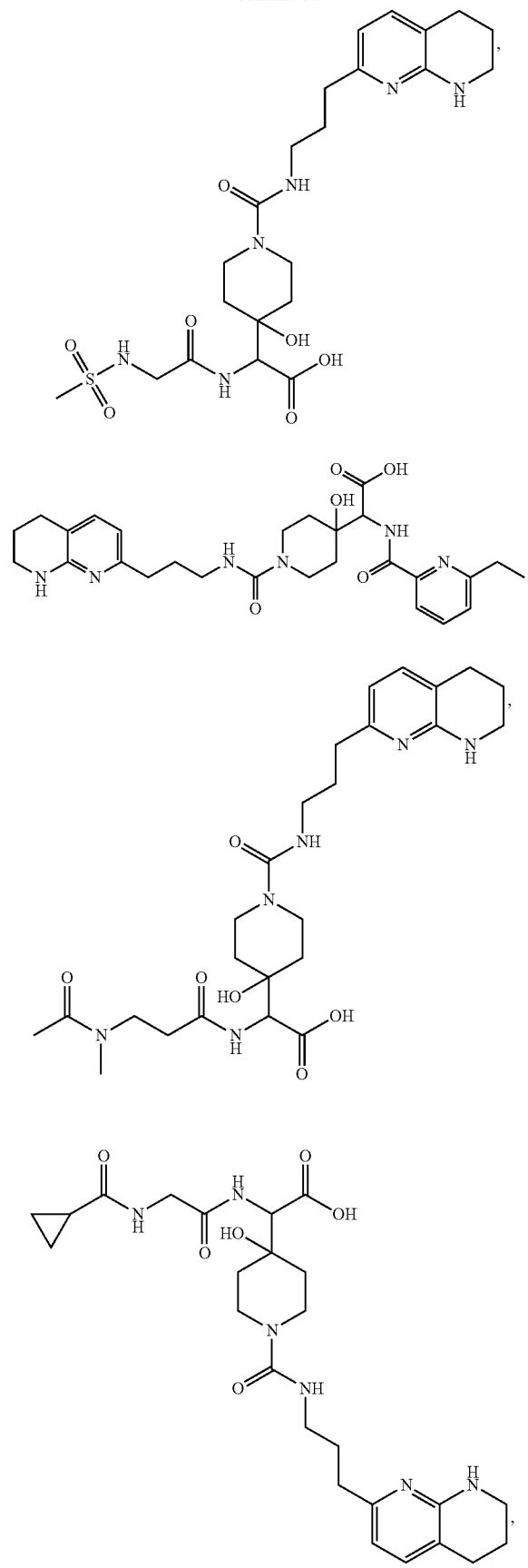
118
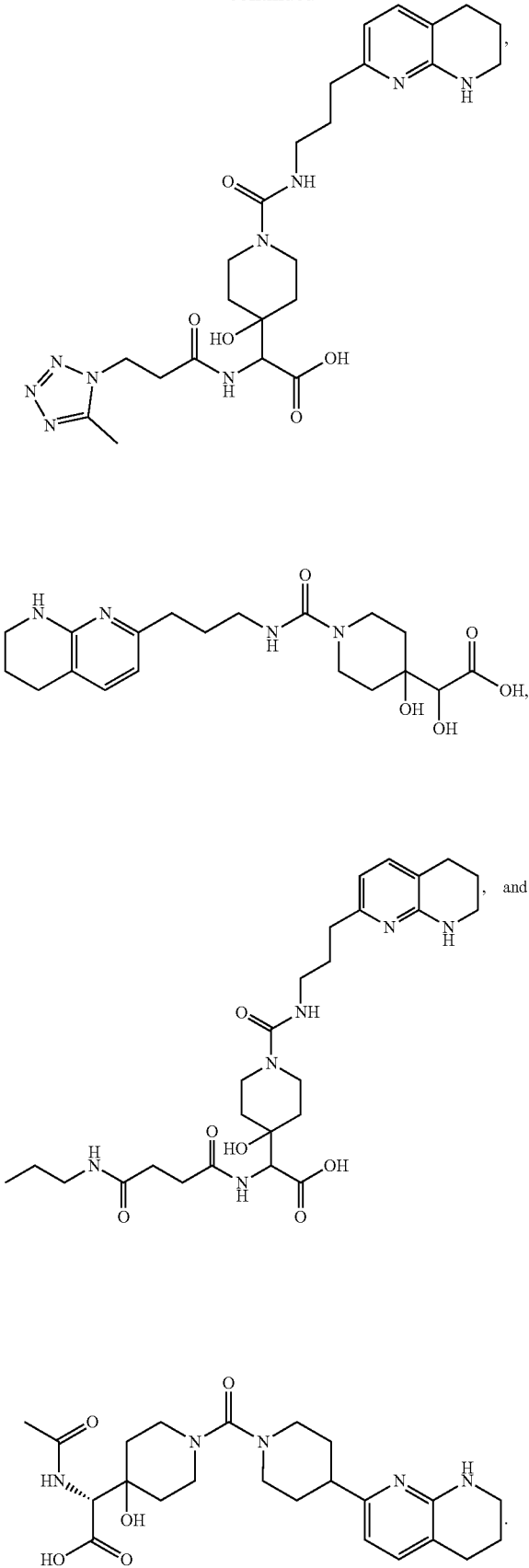

28. The compound of claim 1, wherein the compound is selected from the group consisting of:
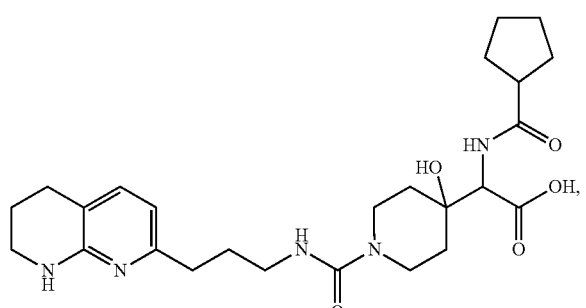
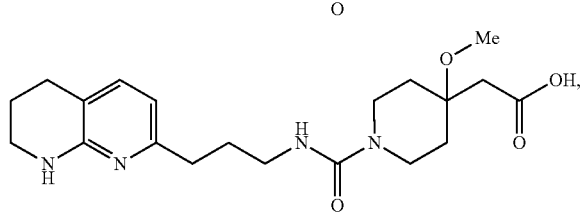
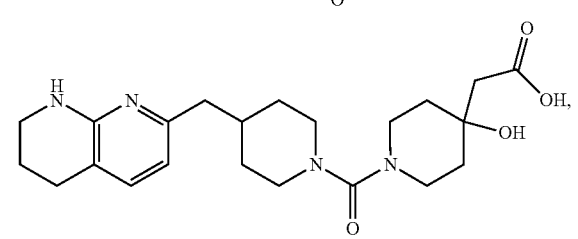
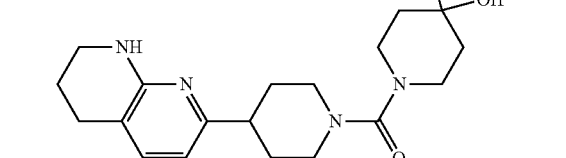
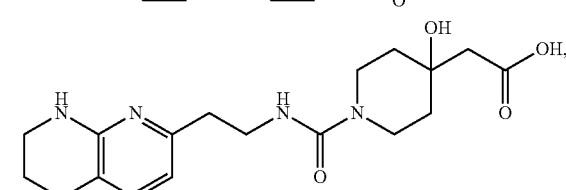
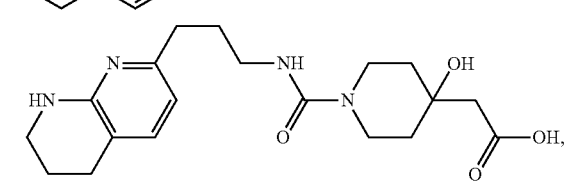
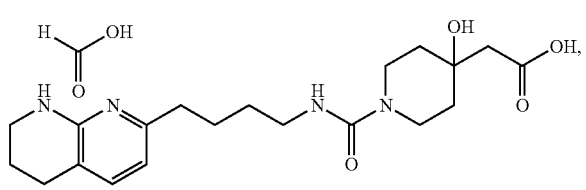
-continued
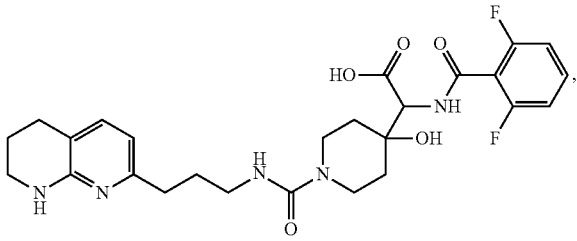
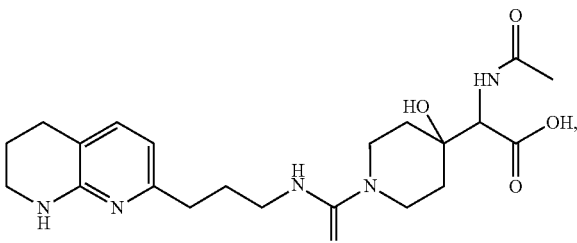
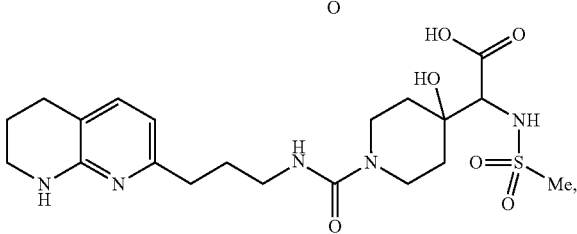
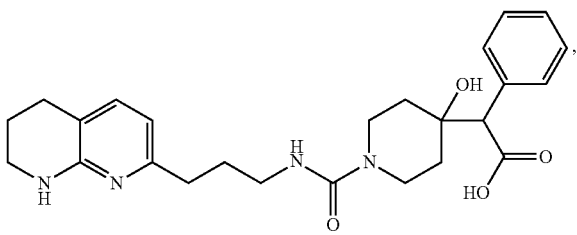
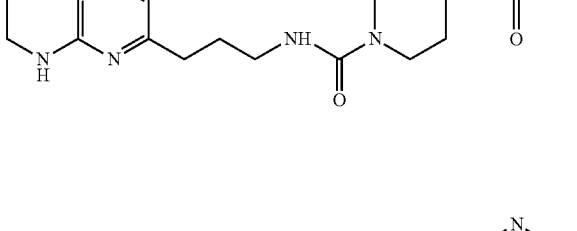
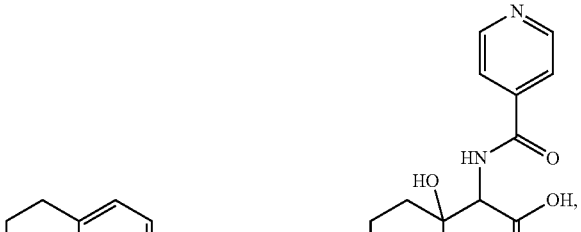
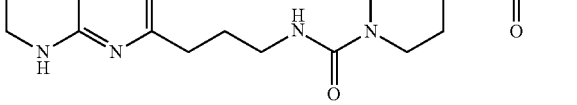

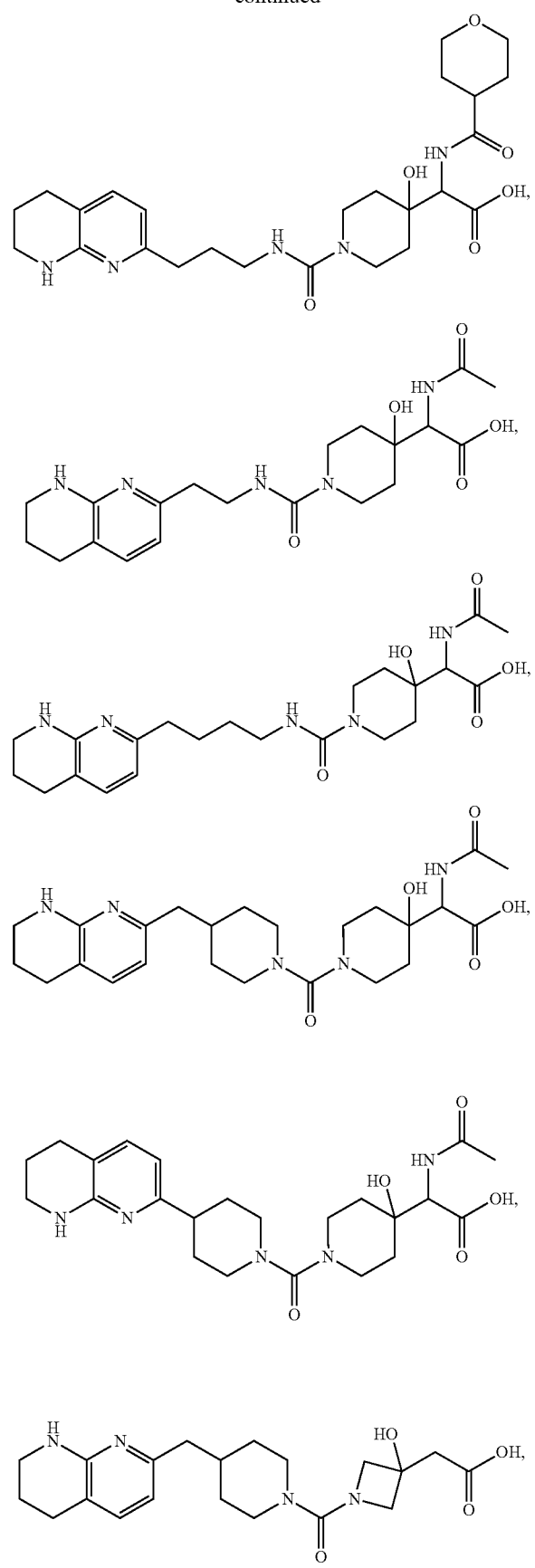
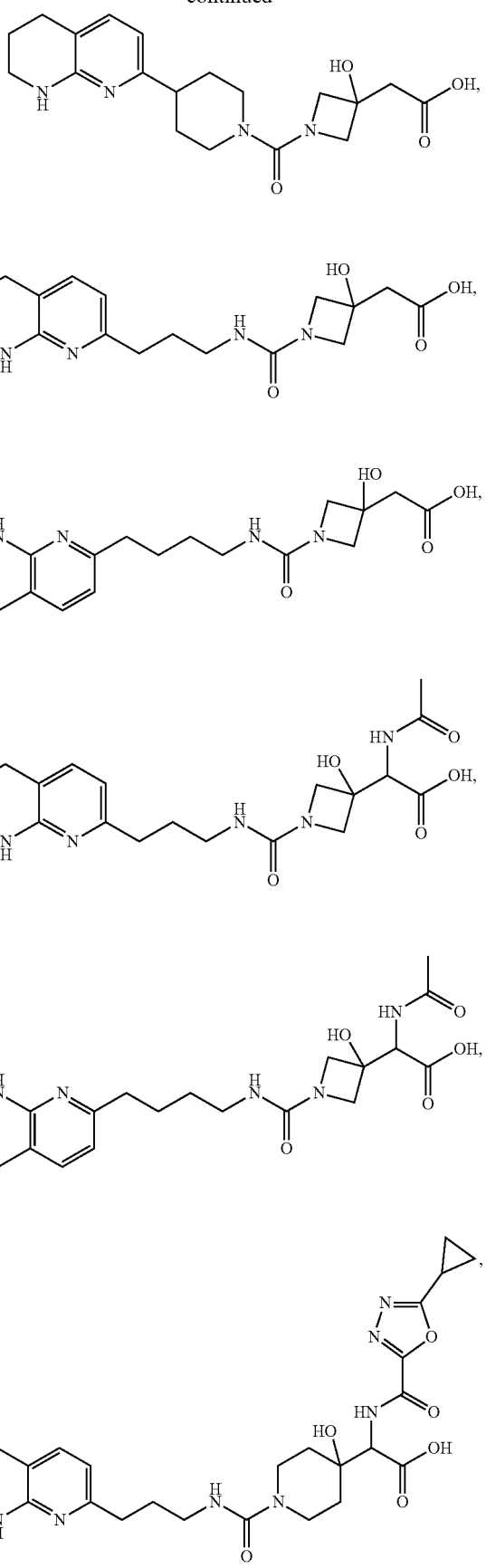

123
-continued
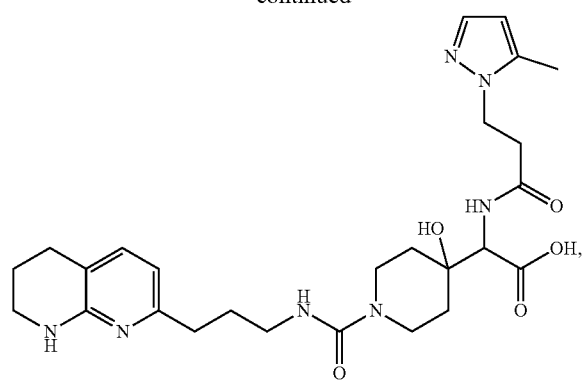
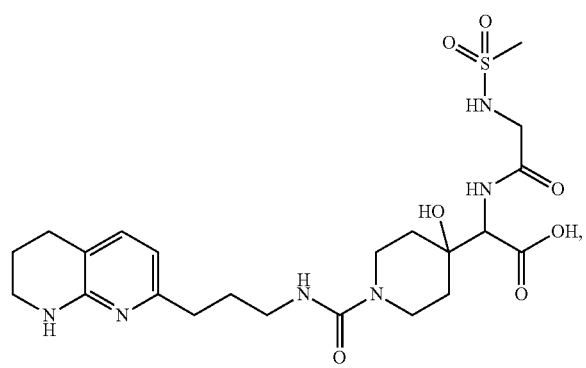
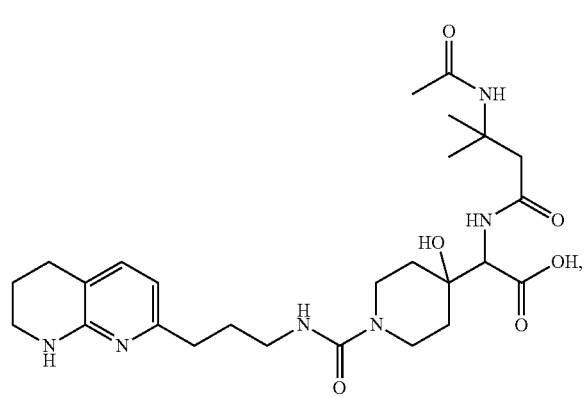
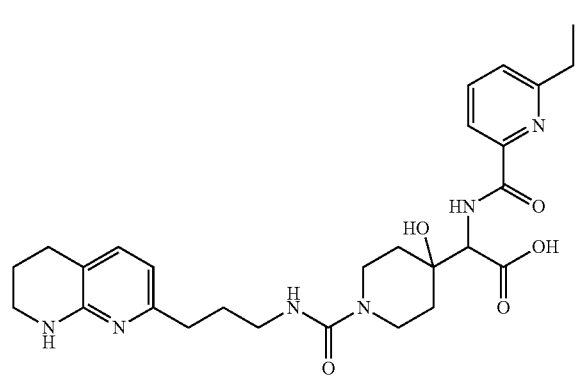
124
-continued
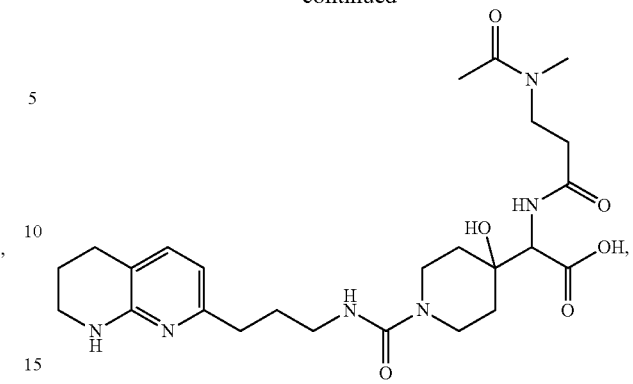
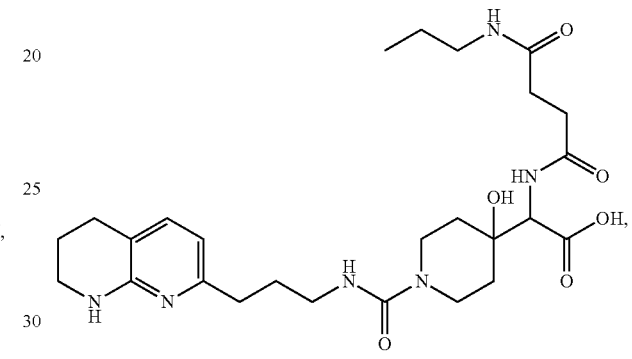
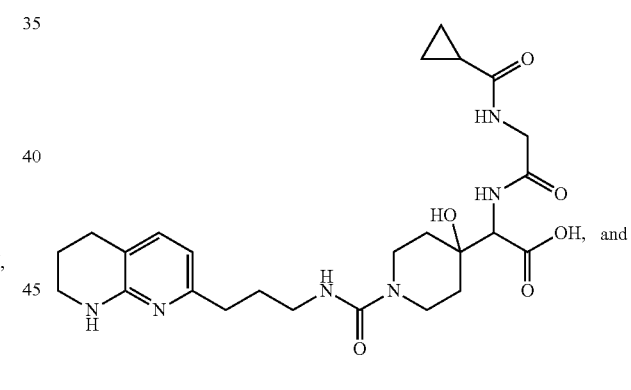, and
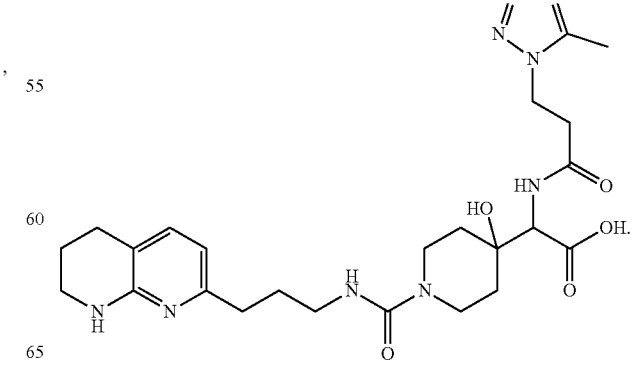

29. The compound of claim 1, wherein the compound is:

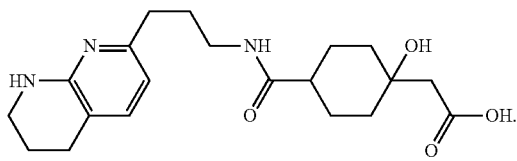 [SMILES: O=C(O)CC1(O)CCC(C(=O)NCCCc2ccc3c(n2)NCCC3)CC1]

30. The compound of claim 10, wherein $R_d$ is H.
31. The compound of claim 30, wherein $R_6$ is H.
32. The compound of claim 31, wherein all instances of $R_1$ are H.
33. The compound of claim 32, wherein R is H or Me.
34. The compound of claim 33, wherein B is

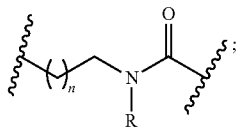

and n is 1, 2 or 3.

35. The compound of claim 34, wherein R is H.

36. The compound of claim 35, wherein $R_2$ is H, alkyl, substituted or unsubstituted aryl, substituted or unsubstituted heteroaryl, cycloalkyl, -alkylene-alkoxy, alkoxy, OH, -alkylene-aryl, heterocycloalkyl, —N(R)C(O)$R_4$, —N(R)SO$_2$R$_4$-, —N(R)-aryl, or —N(R)— heteroaryl.

37. The compound of claim 36, wherein $R_2$ is H.

38. The compound of claim 1, wherein R is H; each $R_1$ is H; $R_6$ is H; $R_d$ is H; and b is 0.

39. The compound of claim 38, wherein B is -alkylene-N(R)C(O)—.

40. The compound of claim 38, wherein B is -alkylene-(heterocyclyl)-C(O)—.

41. The compound of claim 38, wherein B is -heterocyclyl-alkylene-N(R)C(O)—.

42. The compound of claim 38, wherein B is -heterocyclyl-C(O)—.

* * * * *